US008262874B2

(12) United States Patent
Forrow et al.

(10) Patent No.: US 8,262,874 B2
(45) Date of Patent: Sep. 11, 2012

(54) BIOSENSOR COATING COMPOSITION AND METHODS THEREOF

(75) Inventors: Nigel John Forrow, Abingdon (GB); Shridhara Alva Karinka, Pleasanton, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1092 days.

(21) Appl. No.: 12/102,374

(22) Filed: Apr. 14, 2008

(65) Prior Publication Data

US 2009/0255811 A1    Oct. 15, 2009

(51) Int. Cl.
*G01N 27/26* (2006.01)
*C12Q 1/25* (2006.01)
*C12Q 1/32* (2006.01)

(52) U.S. Cl. ......... 204/403.11; 204/403.01; 204/403.04; 204/403.14; 204/403.1; 435/287.3; 435/287.1; 435/287.9; 436/518; 436/501

(58) Field of Classification Search ..... 204/400–403.15; 205/777.5, 778, 792; 436/501–518; 600/309–367; 435/287.1–287.9
See application file for complete search history.

(56) References Cited

U.S. PATENT DOCUMENTS

| | | | |
|---|---|---|---|
| 4,849,330 A * | 7/1989 | Humphries et al. | ....... 205/777.5 |
| 5,262,035 A | 11/1993 | Gregg et al. | |
| 5,304,468 A | 4/1994 | Phillips et al. | |
| 5,320,725 A | 6/1994 | Gregg et al. | |
| 5,365,786 A | 11/1994 | Douglas | |
| 5,393,903 A | 2/1995 | Grätzel et al. | |
| 5,589,326 A | 12/1996 | Deng et al. | |
| 5,593,852 A | 1/1997 | Heller et al. | |
| 5,665,222 A | 9/1997 | Heller et al. | |
| 5,972,199 A | 10/1999 | Heller et al. | |
| 6,077,660 A | 6/2000 | Wong et al. | |
| 6,134,161 A | 10/2000 | Taniguchi et al. | |
| 6,139,798 A | 10/2000 | Klimant et al. | |
| 6,143,164 A | 11/2000 | Heller et al. | |
| 6,175,752 B1 | 1/2001 | Say et al. | |
| 6,338,790 B1 | 1/2002 | Feldman et al. | |
| 6,605,200 B1 | 8/2003 | Mao et al. | |
| 6,605,201 B1 | 8/2003 | Mao et al. | |
| 6,616,819 B1 | 9/2003 | Liamos et al. | |

(Continued)

FOREIGN PATENT DOCUMENTS

WO    0020626    4/2000

(Continued)

OTHER PUBLICATIONS

Evonik Industries, Oct. 2007 "Specifications and test methods for EUDRAGIT® FS 30 D."

(Continued)

*Primary Examiner* — Jeffrey T Barton
*Assistant Examiner* — Jennifer Dieterle
(74) *Attorney, Agent, or Firm* — Edward J. Baba; Khin K. Chin; Bozicevic, Field & Francis LLP

(57) ABSTRACT

The disclosure provides for reagent compositions for biosensors comprising release polymers, methods of making such biosensors and films of reagent compositions comprising release polymers. The reagent compositions comprise a release polymer and an effective analyte detecting amount of an enzyme an enzyme cofactor and a redox compound capable of acting in a biosensor as (i) a redox mediator associated with a working electrode (ii) a redox couple associated with a reference electrode or (iii) the redox mediator associated with the working electrode and the redox couple for the reference electrode.

42 Claims, 21 Drawing Sheets

U.S. PATENT DOCUMENTS

| | | | |
|---|---|---|---|
| 6,676,816 B2 | 1/2004 | Mao et al. | |
| 6,863,800 B2 | 3/2005 | Karinka et al. | |
| 7,312,042 B1 | 12/2007 | Petyt et al. | |
| 2005/0186245 A1* | 8/2005 | Hunter et al. | 424/423 |
| 2006/0113187 A1 | 6/2006 | Deng et al. | |
| 2006/0201805 A1* | 9/2006 | Forrow et al. | 204/403.1 |
| 2007/0279467 A1* | 12/2007 | Regan et al. | 347/100 |

FOREIGN PATENT DOCUMENTS

| | | | |
|---|---|---|---|
| WO | WO 01/36430 | | 5/2001 |
| WO | 2006057722 | | 6/2006 |
| WO | WO2006065900 | * | 6/2006 |
| WO | 2009049093 | | 4/2009 |

OTHER PUBLICATIONS

Evonik Industries, Oct. 2007 "Specifications and test methods for EUDRAGIT® L 100 and EUDRAGIT® S 100."

Evonik Industries, Nov. 2007 "Specifications and test methods for EUDRAGIT® NE 40 D."

Evonik Industries, Nov. 2007 "Specifications and test methods for EUDRAGIT® RL 100 and EUDRAGIT® RL PO, EUDRAGIT® RS 100 and EUDRAGIT® RS PO."

Evonik Industries, Nov. 2007 "Specifications and test methods for EUDRAGIT® RL 30 D and EUDRAGIT® RS 30 D."

Evonik Industries, Sep. 2007 "Specifications and test methods for EUDRAGIT® E 100, EUDRAGIT® E PO and EUDRAGIT® E 12,5."

Kollicoat® IR, Oct. 2001 "Development Product: Polyvinyl alcohol-polyethylene glycol graft copolymer for instant-release coatings and quick-dissolving formulations."

Kollicoat® Protect, Jul. 2007 "Protective coating providing a moisture barrier and taste masking."

Kollicoat® IR White, Jan. 2008 "Ready-to-use coating for instant-release dosage forms."

Kollicoat® SR 30 D, Feb. 2008 "Polyvinyl acetate dispersion for sustained-release pharmaceutical formulations."

Kollicoat® MAE grades, Apr. 2006 "Methacrylic acid/ethyl acrylate copolymers for enteric coatings."

Extended European Search Report for European Application No. 09732946.0, dated Oct. 13, 2011.

* cited by examiner

BIOSENSOR COATING COMPOSITION AND METHODS THEREOF

FIELD

The disclosure relates to reagent films, analytical sensors for the detection of bioanalytes, and methods of making and using the reagent films.

BACKGROUND

Analytical sensors are useful in chemistry and medicine to determine the presence and concentration of a bioanalyte. Such sensors are needed, for example, to monitor glucose in diabetic patients, cholesterol in hypercholesterolemic patients and lactate during critical care events.

Patients, laboratory technicians and physicians rely upon accuracy and consistency of test results from analytical sensors to guide diagnosis and to take informed, appropriate medical action. It would be useful and helpful to produce analytical sensors that consistently give reproducible test results.

Additionally, it would be useful to have an economical method of manufacturing analytical sensors that provide consistent and accurate analyte testing results.

SUMMARY

Embodiments of the claimed subject matter include a reagent composition comprising a release polymer and an effective analyte detecting amount of an enzyme; an enzyme cofactor; and a redox compound capable of acting in a biosensor as (i) a redox mediator associated with a working electrode; (ii) a redox couple associated with a reference electrode; or (iii) the redox mediator associated with the working electrode and the redox couple for the reference electrode.

Other embodiments include reagent compositions wherein the reagent composition covers at least a portion of the working electrode, at least a portion of the reference electrode or both at least a portion of the working electrode and at least a portion of the reference electrode.

In yet other embodiments the reagent composition has a rheology that is substantially Newtonian and is in the range from about 0.5 mPa s to about 25 mPa s.

Other embodiments of the reagent composition include the release polymer that has dispersed within it an effective amount of an enzyme; an enzyme cofactor; and a redox compound capable of acting in a biosensor as (i) a redox mediator for a working electrode; (ii) a redox couple for a reference electrode; or (iii) a redox mediator for a working electrode and the redox couple for a reference electrode.

In further embodiments the reagent composition comprises a trigger electrode.

Other embodiments include a reagent composition that covers at least a portion of the trigger electrode.

In some embodiments the release polymer of the reagent composition is a fast release polymer.

In other embodiments the fast release polymer is polyvinyl alcohol-polyethylene glycol graft copolymer.

In yet other embodiments of the reagent composition the number average molecular weight ($M_n$) of the fast release polyvinyl alcohol-polyethylene glycol graft copolymer is from about 30,000 to about 60,000.

In some embodiments of the reagent composition the release polymer is a sustained release polymer.

In yet other embodiments of the reagent composition the release polymer is the sustained release polymer polyvinyl acetate.

In other embodiments of the reagent composition the sustained release polymer is polyvinyl acetate and is in aqueous media.

Other embodiments include the number average molecular weight ($M_n$) of the polyvinyl acetate ranging from about 10,000 to about 2,000,000.

In some embodiments of the reagent composition the release polymer is an acrylic polymer.

In yet other embodiments of the reagent composition the number average molecular weight ($M_n$) of the acrylic polymer is from about 50,000 to about 1,500,000.

In further embodiments of the reagent composition the release polymer comprises polyvinyl alcohol-polyethylene glycol graft copolymer, polyvinyl acetate, acrylic polymer or mixtures thereof.

In other embodiments of the present disclosure the reagent composition has the redox compound of the formula $[M(PQ)_3]X_2$ wherein M is Ni, Mn, Fe, Co, Os, or Ru and PQ is:

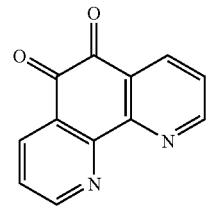

and X is a counter anion.

In yet another embodiment of the reagent composition the sustained release polymer is poly(vinyl acetate); the enzyme is dehydrogenase; and the enzyme cofactor comprises NAD sodium salt, NAD(P), NAD, FAD or PQQ.

In some embodiments of the reagent composition the dehydrogenase enzyme is glucose GDH dependent, cholesterol dependent or ketone dependent.

In yet other embodiments of the reagent composition the sustained release polymer is poly(vinyl acetate); the enzyme is cholesterol dehydrogenase; and the enzyme cofactor comprises NAD sodium salt, FAD or PQQ.

Other embodiments of the present disclosure of the reagent composition include reagent compositions wherein the sustained release polymer is poly(vinyl acetate); the enzyme is 3-hydroxybutyrate dehydrogenase; and the enzyme cofactor comprises NAD sodium salt, FAD or PQQ.

Other embodiments include reagent compositions wherein the sustained release polymer is poly(vinyl acetate); the enzyme is a NAD(P)-dependent dehydrogenase; the enzyme cofactor is NAD sodium salt; and the redox compound is $[Ni(PQ)_3]Cl_2$, $[Ni(PQ)_3]Br_2$ or mixtures thereof wherein PQ is:

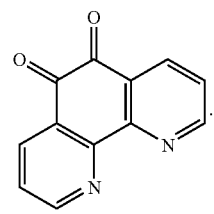

Other embodiments include a reagent composition wherein the redox compound is [M(PQ)₃]X₂ wherein M is Fe or Ru; PQ is represented by the structure

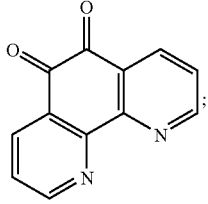

and X is a counter anion.

Further embodiments include reagent compositions wherein the redox compound is [Os(PQ)₃]X₂ where PQ is:

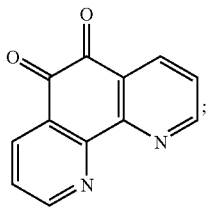

and X is a counter anion.

In yet other embodiments of the reagent composition the redox compound is independently chosen from [Fe(CN)₆]³⁻ (ferricyanide), Ru(NH₃)₆]³⁺ (hexaammine ruthenium(III)), 2,6-dichlorophenol indophenol (DCIP), [Os(dmo)₂(1-vinyl imidazole)X]X, [Os(dmo)₂(1-vinyl imidazole)X]X₂, [Os(dmo)₂(imidazole)X]X, [Os(dmo)₂(imidazole)X]X₂, [Os(dmo)₂(1-methylimidazole)X]X₂, [Os(dmo)₂(methylimidazole)X]X₂,

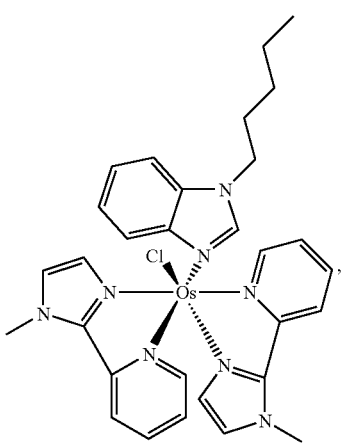

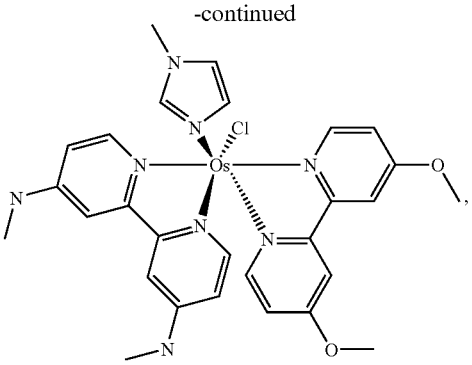

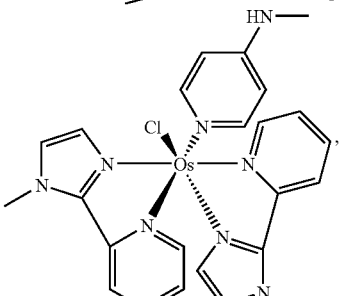

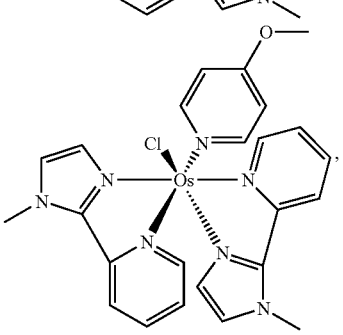

or mixtures thereof, wherein dmo is 4,4'-dimethoxy-2,2'-bipyridine, and X is halogen.

Some embodiments of the claimed subject matter include a method of coating a biosensor comprising coating a reagent composition comprising a release polymer and an effective analyte detecting amount of an enzyme; an enzyme cofactor; and a redox compound capable of acting in a biosensor on at least one electrode on the biosensor substrate providing a coated biosensor; and drying the coated biosensor to produce an analyte detecting composition film.

Some further embodiments include a method of coating a biosensor wherein the drying step is selected from using air, O₂, CO₂, convection, vacuum, infra-red or combinations thereof.

Other embodiments include a method of coating a biosensor wherein the reagent composition is coated using a slot-die coating method.

Yet other embodiments use a method of coating a biosensor wherein the reagent composition is coated using ink jet coating methods, drop coating methods, hand coating methods, squeegee coating methods, spray coating methods, rod coating methods, roll coating methods, dip coating methods, meter rod coating methods, spin coating methods, curtain coating methods, slide coating methods or combination thereof.

Other embodiments use a method of coating a biosensor wherein the reagent composition has a viscosity of from about 0.4 mPa s to about 10 mPa s.

In yet other embodiments a method of coating a biosensor is used wherein the reagent composition has a viscosity of from about 1.0 mPa s to about 5 mPa s.

Other embodiments use a method of coating a biosensor wherein the analyte detecting composition film has an average thickness of from about 2 μm to about 7 μm.

Yet in other embodiments a method of coating a biosensor is used wherein the analyte detecting composition film has an average thickness of from about 3 μm to about 6 μm.

In a further embodiment a method of coating a biosensor is used wherein the analyte detecting composition film produced has a substantially uniform thickness.

In some embodiments the method of coating a biosensor uses a composition wherein the rheology of the reagent composition is substantially Newtonian.

A further embodiment of the claimed subject matter is a biosensor comprising at least one electrode; and a reagent composition associated with the at least one electrode, the reagent composition comprising a release polymer and an effective analyte detecting amount of an enzyme; an enzyme cofactor; and a redox compound capable of acting in a biosensor as (i) a redox mediator for a working electrode; (ii) a redox couple for a reference electrode; or (iii) a redox mediator for a working electrode and the redox couple for a reference electrode.

In yet another embodiment, the release polymer of the biosensor has dispersed within it an effective amount of an enzyme; an enzyme cofactor; and a redox compound capable of acting in a biosensor as (i) a redox mediator for a working electrode; (ii) a redox couple for a reference electrode; or (iii) a redox mediator for a working electrode and the redox couple for a reference electrode.

In some embodiments the release polymer of the biosensor is a polymer that is soluble in water.

In yet other embodiments the release polymer of the biosensor is a polymer that is substantially insoluble in water.

In some embodiments the biosensor comprises redox compounds of the formula $[M(PQ)_3]X_2$ wherein M is Ni, Mn, Fe, Co, Os, or Ru; PQ is:

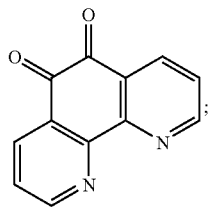

and X is a counter anion.

In yet other embodiments the biosensor comprises a reagent composition wherein the sustained release polymer is poly(vinyl acetate); the enzyme is a NAD(P)-dependent dehydrogenase; the enzyme cofactor is NAD sodium salt; and the redox compound is $[Ni(PQ)_3]Cl_2$, $[Ni(PQ)_3]Br_2$ or mixtures thereof wherein PQ is:

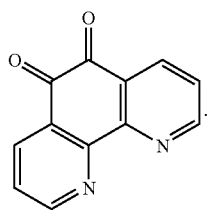

In yet other embodiments the biosensor comprises the redox compound $[M(PQ)_3]X_2$ wherein M is Fe or Ru and PQ is:

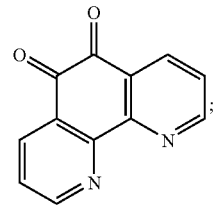

and X is a counter anion.

In further embodiments of the biosensor the redox compound is $[Os(PQ)_3]X_2$ wherein PQ is

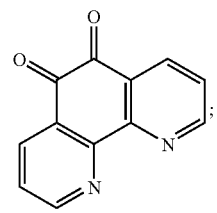

and X is a counter anion.

In some embodiments the biosensor has the sustained release polymer poly(vinyl acetate); the enzyme is dehydrogenase; and the enzyme cofactor comprises NAD sodium salt, FAD or PQQ.

In some embodiments of the biosensor the release polymer is poly(vinyl acetate); the enzyme is NAD(P)-dependent dehydrogenase; the enzyme cofactor is NAD sodium salt; and the redox mediator is $[Ni(PQ)_3]Cl_2$, $[Ni(PQ)_3]Br_2$ or mixtures thereof wherein PQ is

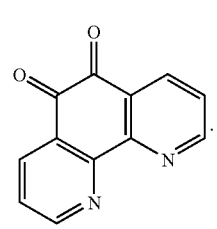

Other embodiments of the claimed subject matter include a biosensor film comprising a release polymer and an effective analyte detecting amount of an enzyme; an enzyme cofactor; and a redox compound capable of acting in a biosensor as (i) a redox mediator for a working electrode; (ii) a redox couple for a reference electrode; or (iii) a redox mediator for a working electrode and the redox couple for a reference electrode.

Further embodiments of the biosensor film comprise a release polymer that has dispersed within it an effective amount of: an enzyme; an enzyme cofactor; and a redox compound capable of acting in a biosensor as (i) a redox mediator for a working electrode; (ii) a redox couple for a reference electrode; or (iii) a redox mediator for a working electrode and the redox couple for a reference electrode.

In yet other embodiments the biosensor film has a fast release polymer.

Some embodiments of the biosensor film the fast release polymer is polyvinyl alcohol-polyethylene glycol graft copolymer.

Yet other embodiments the biosensor film has the number average molecular weight ($M_n$) of the fast release polyvinyl alcohol-polyethylene glycol graft copolymer ranging from about 30,000 to about 60,000.

In yet other embodiments the biosensor film has a release polymer that is a sustained release polymer.

Further embodiments of the biosensor film have a sustained release polymer that is polyvinyl acetate.

Yet other embodiments have a biosensor film with the number average molecular weight ($M_n$) of the polyvinyl acetate ranging from about 10,000 to about 2,000,000.

In yet other embodiments of the biosensor film the release polymer is an acrylic polymer.

Other embodiments of the biosensor film can have an number average molecular weight ($M_n$) of the acrylic polymer ranging from about 50,000 to about 1,500,000.

In yet other embodiments the biosensor film has a release polymer comprising polyvinyl alcohol-polyethylene glycol graft copolymer, polyvinyl acetate, acrylic polymer or mixtures thereof.

Further embodiments of the biosensor film have comprise redox compounds of the formula: $[M(PQ)_3]X_2$ wherein M is Ni, Mn, Fe, Co, Os, or Ru; PQ is

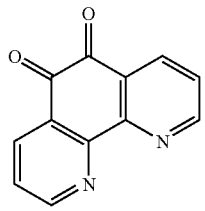

and X is a counter anion.

Some embodiments of the biosensor film have the sustained release polymer poly(vinyl acetate); the enzyme dehydrogenase; and the enzyme cofactor NAD sodium salt, FAD or PQQ.

Further embodiments of the biosensor film have the sustained release polymer poly(vinyl acetate); the enzyme NAD (P)-dependent dehydrogenase; the enzyme cofactor NAD sodium salt; and the redox compound $[Ni(PQ)_3]Cl_2$, $[Ni(PQ)_3]Br_2$ or mixtures thereof wherein PQ is

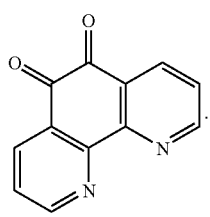

In yet other embodiments the biosensor film has the redox compound $[M(PQ)_3]X_2$ wherein M is Fe or Ru; PQ is

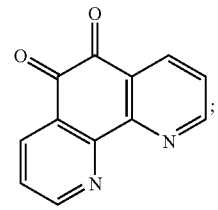

and X is a counter anion.

Other embodiments of the biosensor film have the redox compound $[Os(PQ)_3]X_2$ wherein PQ is

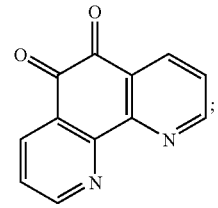

and X is a counter anion.

Some embodiments of the biosensor film further comprise a colorant.

In yet other embodiments of the biosensor film the colorant is a flavin mononucleotide (FMN) of the structure:

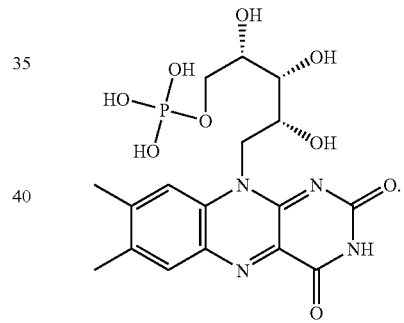

In yet other embodiments the biosensor film is associated with an optical sensor, comprising a release polymer and an effective analyte detecting amount of an enzyme; an enzyme cofactor; and a redox compound capable of acting in a biosensor as (i) a redox mediator (ii) a redox couple; or (iii) a redox mediator and a redox couple.

In Some embodiments the optical sensor comprises the redox compound of the formula: $[M(PQ)_3]X_2$ wherein M is Ni, Mn, Fe, Co, Os, or Ru; PQ is

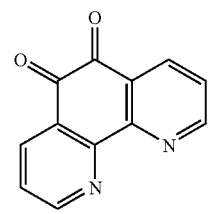

and X is a counter anion.

In yet other embodiments the optical sensor has the sustained release polymer poly(vinyl acetate); the enzyme dehydrogenase; and the enzyme cofactor NAD sodium salt, FAD or PQQ.

Other embodiments of the optical sensor include the sustained release polymer poly(vinyl acetate); the enzyme is a NAD(P)-dependent dehydrogenase; the enzyme cofactor is NAD sodium salt; and the redox compound is $[Ni(PQ)_3]Cl_2$, $[Ni(PQ)_3]Br_2$ or mixtures thereof wherein PQ is

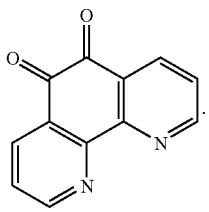

In yet other embodiments the optical sensor comprises the redox compound $[M(PQ)_3]X_2$ wherein M is Fe or Ru; PQ is

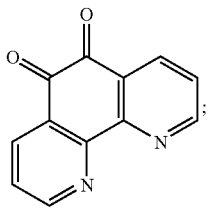

and X is a counter anion.

Some embodiments of the optical sensor include the redox compound $[Os(PQ)_3]X_2$ wherein PQ is

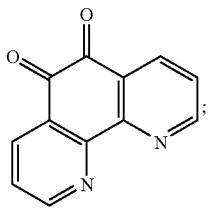

and X is a counter anion.

Other embodiments of the optical sensor further comprise a colorant.

BRIEF DESCRIPTION OF THE DRAWINGS

Referring now to the drawings, wherein like reference numerals and letters indicate corresponding structure throughout the several views.

DETAILED DESCRIPTION OF THE EMBODIMENTS

Figure 1:
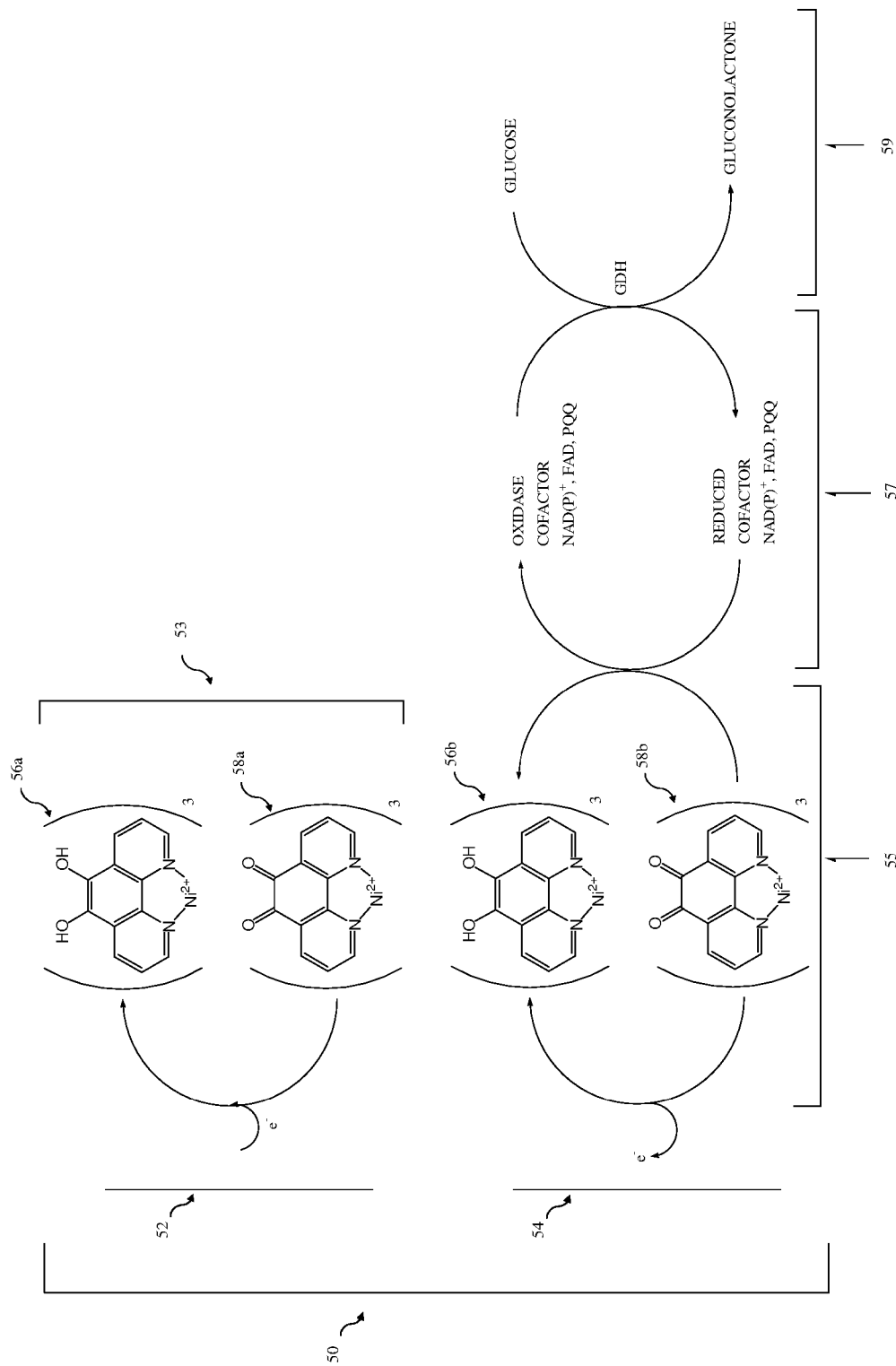
FIG. 1 is an illustrative redox cycle diagram in accordance to the embodiments.

As used herein, the following definitions define the stated term:

An "acrylic polymer" as used herein means a substantially water insoluble polymer, copolymer or polymer blend comprising the following monomers: acrylic acid, methacrylic acid, acrylate and methacrylate esters particularly the methyl, ethyl, propyl, and butyl esters, and derivatives thereof, and water insoluble derivatives of acrylic and methacrylic acid. Also included are water insoluble hydroxylated acrylic and methacrylic esters.

The term "alkyl" includes linear or branched, saturated aliphatic hydrocarbons. Examples of alkyl groups include methyl, ethyl, n-propyl, isopropyl, n-butyl, tert-butyl and the like. Unless otherwise noted, the term "alkyl" includes both alkyl and cycloalkyl groups.

The term "alkoxy" describes an alkyl group joined to the remainder of the structure by an oxygen atom. Examples of alkoxy groups include methoxy, ethoxy, n-propoxy, isopropoxy, butoxy, tert-butoxy, and the like. In addition, unless otherwise noted, the term 'alkoxy' includes both alkoxy and cycloalkoxy groups.

The term "alkenyl" describes an unsaturated, linear or branched aliphatic hydrocarbon having at least one carbon-carbon double bond. Examples of alkenyl groups include ethenyl, 1-propenyl, 2-propenyl, 1-butenyl, 2-methyl-1-propenyl, and the like.

A "reactive group" is a functional group of a molecule that is capable of reacting with another compound to couple at least a portion of that other compound to the molecule. Reactive groups include carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. Activated esters, as understood in the art, generally include esters of succinimidyl, benzotriazolyl, or aryl substituted by electron-withdrawing groups such as sulfo, nitro, cyano, or halo groups; or carboxylic acids activated by carbodiimides.

A "substituted" functional group (e.g., substituted alkyl, alkenyl, or alkoxy group) includes at least one substituent selected from the following: halogen, alkoxy, mercapto, aryl, alkoxycarbonyl, alkylaminocarbonyl, dialkylaminocarbonyl, —OH, —NH$_2$, alkylamino, dialkylamino, trialkylammonium, alkanoylamino, arylcarboxamido, hydrazino, alkylthio, alkenyl, and reactive groups.

A "biological fluid" is any body fluid, typically human, in which the analyte can be measured, for example, blood (which includes whole blood and its cell-free components, such as, plasma and serum), interstitial fluid, dermal fluid, sweat, tears, urine and saliva.

An "electrochemical sensor" is a device configured to detect the presence of or measure the concentration or amount of an analyte in a sample via electrochemical oxidation or reduction reactions. These reactions typically can be transduced to an electrical signal that can be correlated to an amount or concentration of analyte.

"Electrolysis" is the electrooxidation or electroreduction of a compound either directly at an electrode or via one or more electron transfer agents (e.g., redox mediators or enzymes).

"Ketone bodies" refer to water-soluble compounds that are produced as by-products when fatty acids are broken down for energy in the liver and kidney. Ketone bodies may be used as a source of energy in the heart and brain. Examples of ketone bodies include acetone, acetoacetic acid, and beta-hydroxybutyric acid, with beta-hydroxybutyric acid also being a carboxylic acid.

A "Newtonian" reagent composition is a fluid wherein the viscosity of the reagent composition is sufficiently independent of shear strain rate, such that a uniform coating of reagent composition film can be achieved using the coating methods described herein.

A "redox couple" is an electron transfer agent which can be interconverted between two oxidation states and which is employed in a reference electrode to provide a known electrode potential.

A "redox mediator" is an electron transfer agent for carrying electrons between an analyte or an analyte-reduced or analyte-oxidized enzyme and an electrode, either directly, or via one or more additional electron transfer agents, such as an enzyme/cofactor. Redox mediators that include a polymeric backbone may also be referred to as "redox polymers". An example of a redox mediator of the invention is a coordination complex comprising osmium.

A "reference electrode" is an electrode that contains a redox couple that provides a known electrode potential and, unless otherwise noted, also used as a counter electrode.

A "uniform coating" describes, in some embodiments, a layer of reagent composition film 20a that covers a portion of the working electrode (FIG. 2) that comes in contact with the biological fluid to be analyzed. In some embodiments the reagent composition film 20a can also cover a portion of the reference electrode that comes in contact with the biological fluid to be analyzed. In other embodiments the reagent composition film 20a can also cover a portion of the counter electrode that comes in contact with the biological fluid to be analyzed. In yet other embodiments, the reagent composition film 242 (FIG. 32) and 342 of (FIG. 33) can be used in optical sensors. The layer of reagent composition film 20a on the working electrode, reference electrode, counter electrode or optical sensor can have a minimum thickness of at least about 3 μm of dried reagent composition film. The layer of reagent composition film on the working electrode, reference electrode or counter electrode can have a maximum thickness of at most about 12 μm.

"Wash-through" occurs when soluble reagents in a reagent composition film are dissolved in the biological fluid and as a result are removed from the measurement area resulting in a lower or errant electrode response.

Throughout the specification and the appended claims, a given chemical formula or name shall encompass all stereo and optical isomers and racemates thereof as well as mixtures in different proportions of the separate enantiomers, where such isomers and enantiomers exist, as well as pharmaceutically acceptable salts thereof. Isomers may be separated using conventional techniques, e.g. chromatography or fractional crystallisation. The enantiomers may be isolated by separation of racemate for example by fractional crystallisation, resolution or HPLC. The diastereomers may be isolated by separation of isomer mixtures for instance by fractional crystallisation, HPLC or flash chromatography. Alternatively the stereoisomers may be made by chiral synthesis from chiral starting materials under conditions which will not cause racemisation or epimerisation, or by derivatisation, with a chiral reagent. All stereoisomers are included within the scope of the invention.

Here and throughout the description and claims, the symbols ↗ and ↗ are used to show a particular three-dimensional conformation. Those skilled in the art will understand that each ↗ can be ↗ and each ↗ can be ↗ so that the structures shown cover all possible isomers unless specifically indicated as being limited to a particular configuration.

Certain compounds of the present invention may exist as tautomers. It is to be understood that the present invention encompasses all such tautomers.

Embodiments of the disclosure recite reagent compositions, reagent composition films and methods of uniformly coating said compositions and films. Reagent compositions can be used to deposit reagent composition films at the measurement site of an optical or an electrochemical biosensor. Reagent composition coatings on biosensors require precise and uniform coating for several reasons. First, the reagent solutions can be expensive and coating an excessive amount of reagent can waste reagent solution. The reagent compositions can be used more effectively and efficiently, because the reagent composition film can be localized with coating methods described herein to a particular relevant area within a biosensor, for example the working electrode area 20 in FIG. 2, where the biological fluid comes in contact with the biosensor. Second, biosensors require delivering consistent results for the analyte thus enabling appropriate and accurate medical responses from the user or physician. To achieve consistent results active components, for example enzymes, coenzymes and redox compounds, and the likes, in the reagent composition coating must be homogeneously distributed throughout the reagent composition. Third, there is a need to prevent wash-through of the soluble reagents in the biosensor to achieve accurate and reproducible measurement of the bioanalyte in question.

Additional needs for coating of reagent compositions include the need to have a dried film of reagent composition that will adhere to the substrate being coated, for example polyethylene terephthalate (PET) or conductive electrodes such as, but not limited to, gold or platinum electrodes. Consistent and intimate contact of the reagent composition film with the electrodes assures accurate and reproducible measurement of the bioanalyte. In addition, some embodiments of the dried reagent composition films in accordance to the embodiments have sufficient strength and durability for processing, packaging, and shelf life without physical failure. The dried films of reagent compositions in accordance to the embodiments are sufficiently flexible and non-tacky so as to be able to withstand processing, for example such as rolling expanses of coated electrodes upon themselves into a reel, without cracking the film, peeling the film, transferring the film from the electrode, or otherwise breaking the film.

The reagent composition can include starches that have been modified by crosslinking, chemically modified for improved stability or optimized performance, or physically modified for improved solubility properties or optimized performance. Chemically modified starches have typically been treated with chemicals so that some hydroxyl groups have been replaced by either ester or ether groups. Very low levels of chemical modification can significantly change the rheological, physical, and chemical properties of starch. Crosslinking, in which two hydroxyl groups on neighboring starch molecules are linked chemically is also a form of chemical modification. As used herein, "pre-gelatinized starches" or "instantized starches" refers to physically modified starches that have been pre-wetted, then dried to enhance their cold-water solubility. Acid-hydrolyzed starch is a term used for a starch suspension treated with dilute acid at a temperature below the gelatinization point. The granular form of the starch is maintained and the reaction is ended by neutralization, filtration and drying once the desired degree of conversion is reached. This results in a reduction in the average molecular size of the starch polymers. Acid-hydrolyzed starches tend to have a lower hot viscosity than native starch and a strong tendency to gel when cooled. Suitable modified starches are commercially available from several suppliers such as, for example, A.E. Staley Manufacturing Company, and National Starch & Chemical Company.

Another suitable modified starch group includes the hydroxypropylated starches. These are starches in which some of the hydroxyl groups have been etherified with hydroxypropyl groups, usually by treatment with propylene oxide. These starches are characterized by having excellent refrigeration and freeze/thaw stability. Hydroxypropyl food starches are generally crosslinked in addition to the etherification. Hydroxypropyl distarch phosphate is a starch used widely in the food industry in which both monofunctional hydroxypropyl groups have been added in combination with phosphate crosslinking. One example of a suitable hydroxypropyl starch is commercially available from Grain Processing Company under the tradename, "PURE-COTE B790".

Suitable acid hydrolyzed starches include that commercially available from Grain Processing Corporation under the tradename, "PURE-SET B950", and hydroxypropyl distarch phosphates such as that commercially available from Grain Processing Corporation under the tradename, "PURE-GEL B990".

Release Polymers

Reagent compositions in accordance to the embodiments contain at least one release polymer. Release polymers in accordance to the embodiments are polymers used to deliver actives, such as redox compounds, enzymes and enzyme cofactors, at a specific time or over a specific time at a characteristic and consistent release rate. Release polymers can be designed such that substantially all the active is released from the polymer within seconds. These are herein designated as fast release polymers. Release polymers can be designed such that the active is more slowly released, for example over minutes or hours. These are herein designated as sustained release polymers.

The system in which the polymer is to be used can dictate whether the release polymer will act as a fast release polymer or sustained release polymer. For example, a polymer can be largely insoluble at one pH, and act as a sustained release polymer. On the other hand, when the pH of the same system is altered to another value, the polymer can become soluble or swellable, thus acting as a fast release polymer.

Release polymers in accordance to the embodiments comprise from about 0.05% to about 15% by weight of the reagent composition. In yet other embodiments the release polymers in accordance to the embodiments comprise from about 0.1% to about 14%, from about 0.1% to about 12%, from about 0.1% to about 10%, from about 0.05% to about 8%, from about 0.1% to about 8%, from about 0.05% to about 7%, from about 0.05% to about 6%, from about 0.1% to about 6%, from about 0.05% to about 5%, from about 0.1% to about 5%, from about 0.05% to about 4%, from about 0.1% to about 4%, from about 0.05% to about 4%, from about 0.05% to about 3%, from about 0.1% to about 3%, from about 1.0% to about 5%, from about 2% to about 5%, from about 3% to about 4% and from about 0.3% to about 3.5% by weight of the reagent composition.

In other embodiments, the release polymers in accordance to the embodiments comprise from about 0.1% to about 60% by weight of the reagent composition film. In yet other embodiments the release polymers in accordance to the embodiments comprise from about 0.1% to about 55%, from about 0.1% to about 50%, from about 0.1% to about 45%, from about 0.1% to about 40%, from about 0.1% to about 35%, from about 0.1% to about 30%, from about 0.1% to about 25%, from about 0.1% to about 20%, from about 0.1% to about 15%, from about 0.1% to about 10%, from about 0.1% to about 8%, from about 0.1% to about 6%, from about 0.1% to about 4%, from about 0.1% to about 3%, from about 0.1% to about 2%, from about 0.1% to about 1%, from about 0.1% to about 0.5%, from about 0.1% to about 0.4% and from about 0.1% to about 0.2% by weight of the reagent composition film. In yet other embodiments the release polymers in accordance to the embodiments comprise from about 0.2% to about 60%, from about 1.0% to about 60%, from about 5.0% to about 60%, from about 10% to about 60%, from about 15% to about 60%, from about 17% to about 60%, from about 20% to about 60%, from about 25% to about 60%, from about 30% to about 60%, from about 35% to about 60%, from about 40% to about 60%, from about 45% to about 60%, from about 50% to about 60%, from about 55% to about 60%, from about 56% to about 60%, from about 57% to about 60%, from about 58% to about 60% and from about 59% to about 60% by weight of the reagent composition film.

In some embodiments of the disclosure, the release polymers are chosen such that the rheological character of the solution of the reagent composition to be applied is Newtonian. The rheological Newtonian character of the reagent composition can be important in some embodiments when applying the reagent composition according to the coating methods described herein. Furthermore, the rheological Newtonian character of the reagent composition in other embodiments are important when the coating methods described herein are applied at varied line speeds, for example but not limited to, slot die coating.

Additionally, in other examples in accordance to the embodiments the release polymers are chosen such that viscosity of the reagent composition is below 25 mPa s. In other embodiments the viscosity of the reagent composition is less than 24 mPa s, 23 mPa s, 22 mPa s, 21 mPa s, 20 mPa s, 19 mPa s, 18 mPa s, 17 mPa s, 16 mPa s, 15 mPa s, 14 mPa s, 13 mPa s, 12 mPa s, 11 mPa s, 10 mPa s, 9 mPa s, 8 mPa s, 7 mPa s, 6 mPa s, 5 mPa s, 4 mPa s, 3 mPa s, 2 mPa s, 1 mPa s, or even less than 0.6 mPa s. Exemplary low viscosity reagent compositions such as these can contribute to uniform coating of the reagent composition film.

The reagent compositions in accordance to the embodiments can comprise release polymers of any elastic, plastic material (i.e., stock film forming material) which will not interfere with the detection of the analyte being measured, cause the rheology to be non-Newtonian or increase the viscosity such that the solution is not conducive to be coated by the methods described herein.

Fast Release Polymers

Polymers that are soluble in the system to be analyzed are generally fast release polymers. For example, if a polymer is water-soluble, it can quickly release actives in an aqueous biosystem such as blood, saliva, urine or the likes. Fast release polymers can include polymers such as polyethylene glycol, hydroxypropyl cellulose, carboxy methyl cellulose, and mixtures thereof, copolymers, block copolymers, graft copolymers of the above homopolymers, and other known water-soluble polymers and gums.

Examples of suitable polymers include, but are not limited to, cellulosics such as methylcellulose, hydroxypropylcellulose (HPC), hydroxyethylmethylcellulose (HEMC), hydroxypropylmethylcellulose (HPMC), hydroxybutylmethylcellulose (HBMC), hydroxyethylethylcellulose (HEEC), and hydroxyethylhydroxypropylmethyl cellulose (HEMPMC); modified starches such as cross-linked starches, chemically modified starches including hydroxypropyl starch, hydroxyethyl starch, methylethyl starch, carboxymethyl starch; and physically modified starches including pre-gelatinized starches; proteins such as gelatin, whey protein, egg albumin, casein and casein isolates, soy protein and soy protein isolates; and other film-forming polymers such as, methacrylic acid and methacrylate ester copolymers, polyvinyl alcohol and polyethylene glycol copolymers, and derivatives and mixtures thereof. Also, sodium alginate, polyethylene glycol, xanthan gum, tragacantha, guar gum, acacia gum, arabic gum, carrageenan, polyacrylic acid, methylmethacrylate copolymer, carboxyvinyl copolymers, and various mixtures of the above and other known water-soluble polymers, cellulose derivatives, and/or gums, among others.

Suitable xanthan gums include those available from C.P. Kelco Company under the tradename, "KELTROL 1000," "XANTROL 180," or "K9B310." For example, hydroxypropyl cellulose (e.g., Klucel, grade JF, Hercules Inc., Aqualon Division) and hydroxylpropyl methylcellulose (e.g., Methocel, grades E5, E50, E4M, and SG A16M by Dow Chemical) can be suitable water-soluble cellulose derivatives. One suitable hydroxypropylmethylcellulose compound is "HPMC 2910", which is a cellulose ether having a degree of substitution of about 1.9 and a hydroxypropyl molar substitution of 0.23, and containing, based upon the total weight of the compound, from about 29% to about 30% methoxyl and from about 7% to about 12% hydroxylpropyl groups. HPMC 2910 is commercially available from the Dow Chemical Company under the tradename, "METHOCEL E." "METHOCEL E5," which is one grade of HPMC-2910 suitable for use in some examples in accordance to the embodiments, has a viscosity of about 4 to 6 cps (4 to 6 millipascal-seconds) at 20° C. in a 2% aqueous solution as determined by a Ubbelohde viscometer. Similarly, "METHOCEL E6," which is another grade of HPMC-2910 suitable for use in some examples in accordance to the embodiments, has a viscosity of about 5 to 7 cps (i.e., 5 to 7 millipascal-seconds) at 20° C. in a 2% aqueous solution as determined by a Ubbelohde viscometer. "METHOCEL E 15," which is another grade of HPMC-2910 suitable for use in some examples in accordance to the embodiments, has a viscosity of about 15000 cps (15 millipascal-seconds) at 20° C. in a 2% aqueous solution as determined by a Ubbelohde viscometer. As used herein, "degree of substitution" shall mean the average number of substituent groups attached to an anhydroglucose ring, and "hydroxypropyl molar substitution" shall mean the number of moles of hydroxypropyl per mole anhydroglucose.

In one embodiment in accordance to the embodiments, reagent compositions comprising graft copolymers of polyvinyl alcohol-polyethylene glycol can produce useful reagent compositions for use in bioanalytical sensors. Reagent compositions comprising water-soluble graft copolymers of polyvinyl alcohol-polyethylene glycol can be fast release polymers.

Representative polymers comprising graft copolymers of polyvinyl alcohol-polyethylene glycol such as KOLLICOAT IR®, KOLLICOAT PROTECT® and KOLLICOAT IR WHITE® are commercially available from BASF, Florham Park, N.J. These polymers have a number average molecular weight ($M_n$) from about 30,000 to about 60,000.

Water-soluble film modifiers can also be used. Water-soluble film modifiers are film-forming agent which modifies the water-swellable characteristics of the film-forming neutral or cationic copolymeric esters useful in reagent compositions in accordance to the embodiments. A typically suitable water-soluble film-modifying agent is a low viscosity (less than or equal to 20 cps) cellulose such as low viscosity hydroxypropyl methyl cellulose, low viscosity hydroxylethyl methyl cellulose; low viscosity sodium carboxymethyl cellulose or a polyethylene glycol selected from polyethylene glycol 200 to polyethylene glycol 8000.

Sustained Release Polymers

Polymers that are insoluble or partially soluble in the system to be analyzed can generally be designated as sustained release polymers. If a polymer is insoluble in water the polymer can slowly release actives in aqueous biosystems such as, for example, blood, saliva and urine. Examples of sustained release polymers include, but are not limited to, acrylates, methylmethacrylates, vinylacetates, vinylesters and copolymers, graft polymers, block copolymers, and mixtures thereof.

In certain embodiments of the disclosure, the hydrophobic acrylic polymer is comprised of copolymerizates of acrylic and methacrylic acid esters having a solubility unaffected by the pH conditions of the reagent composition and sample. These copolymerizates can further include a low content of quaternary ammonium groups, which occur as salts.

The sustained release polymers in accordance to the embodiments comprise aqueous dispersions of hydrophobic (water-insoluble) acrylic polymers. In some embodiments, the hydrophobic acrylic polymer coatings in accordance to the embodiments have a solubility independent of the pH of the fluid present in the sample to be tested for the analyte. Hydrophobic acrylic polymers which can be used in the formulations in accordance to the embodiments are derived from acrylic acid or derivatives thereof. Acrylic acid derivatives include, for example, the esters of acrylic acid and methacrylic acid, and the alkyl esters of acrylic acid and methacrylic acid. In certain preferred embodiments, the alkyl esters of acrylic acid and methacrylic acid have from about 1 to about 8 carbon atoms in the alkyl group. Generally, monomers forming hydrophobic water-insoluble polymers are nonionic.

In some embodiments of the disclosure, the sustained release polymer is derived from a mixture of two acrylic polymers used in the form of aqueous dispersions, commercially available from Evonik under the Tradename EUDRAGIT® RL 30 D and EUDRAGIT® RS 30 D, respectively. EUDRAGIT® RL 30 D and EUDRAGIT® RS 30 D are copolymers of acrylic and methacrylic esters with a low content of quaternary ammonium groups, the molar ratio of ammonium groups to the remaining neutral (meth)acrylic esters being 1:20 in EUDRAGIT® RL 30 D and 1:40 in EUDRAGIT® RS 30 D. The mean molecular weight is about 150,000. The code designations refer to the permeability properties of these agents, RL for high permeability and RS for low permeability. EUDRAGIT® RL/RS mixtures are insoluble in water. However, reagent compositions formed from EUDRAGIT® RL/RS mixtures are swellable and permeable in aqueous solutions.

The EUDRAGIT® RL/RS mixtures of use in accordance to the embodiments can be mixed together in any desired ratio in order to ultimately obtain a sustained release polymer composition having a desirable release profile. Desirable controlled release formulations can be obtained, for instance, from a polymer composition containing from 100% EUDRAGIT® RL, 50% EUDRAGIT® RL and 50% EUDRAGIT® RS, and 10% EUDRAGIT® RL: EUDRAGIT® 90% RS, and 100% EUDRAGIT® RS.

The hydrophobic acrylic polymer coatings in accordance to the embodiments can also include hydrophilic monomers having a solubility, which is not dependent on pH. Examples are acrylamide and methacrylamide, hydroxy alkyl esters of acrylic acid and methacrylic acid, and vinyl pyrrolidone. Such materials, if used, can be included in small amounts up to 20 percent by weight of the copolymer. Also, small amounts of ionic monomers, such as acrylic acid or methacrylic acid or amino monomers on which the quaternized monomers are based, can also be included.

In one embodiment of the disclosure, reagent compositions comprising acrylic polymers, copolymers of poly(methyl methacylate), poly(methylacrylic acid), acrylate and methacrylate can produce useful reagent compositions for use in analytical sensors. These polymers can have a number average molecular weight range ($M_n$) from about 50,000 to about 1,500,000.

Representative sustained release polymers include, but are not limited to, KOLLICOAT MAE30DP, EUDRAGIT FS30D®, EUDRAGIT NE30D®, EUDRAGIT NE40D®, EUDRAGIT S100®, EUDRAGIT RL30D®, EUDRAGIT RLPO®, EUDRAGIT RS30D®, EUDRAGIT RSPO®, EUDRAGIT EPO® (available from Evonik Industries, Germany) and mixtures thereof.

In other embodiments of the disclosure, the hydrophobic acrylic sustained release polymer composition further comprises a polymer whose permeability is pH dependent, such as anionic polymers synthesized from methacrylic acid and methacrylic acid methyl ester. Such polymers are commercially available, e.g., from Evonik under the tradename EUDRAGIT® L and EUDRAGIT® S. The ratio of free carboxyl groups to the esters is about 1:1 in EUDRAGIT® L and about 1:2 in EUDRAGIT® S. EUDRAGIT® L is insoluble in acids and pure water, but becomes increasingly soluble above pH 5.0. EUDRAGIT® S is similar, except that it becomes increasingly soluble above pH 7. The hydrophobic acrylic polymer coatings can also include a polymer, which is cationic in character based on dimethylaminoethyl methacrylate and neutral methacrylic acid esters (such as EUDRAGIT® E, commercially available from Evonik). The hydrophobic acrylic polymer coatings in accordance to the embodiments can further include a neutral copolymer based on poly(meth) acrylates, such as EUDRAGIT® NE, commercially available from Evonik. EUDRAGIT® NE 30D polymers are insoluble in water and digestive fluids, but permeable and swellable.

In other examples in accordance to the embodiments polyvinyl acetate can be included in the reagent composition as a sustained release polymer. One example of a polyvinyl acetate dispersion is KOLLICOAT SR30D®, available from BASF, Florham Park, N.J.

The dissolution profile of some reagent composition films in accordance to the embodiments can by altered by changing the relative amounts of different acrylic polymers included in the reagent composition. Also, by changing the molar ratio of polymerizable permeability-enhancing agent (e.g., the quaternary ammonium compounds) to the neutral (meth)acrylic esters, the permeability properties (and thus the dissolution profile) of the resultant reagent composition can be modified.

In some embodiments the release rate of reagents, such as for example enzymes, coenzymes, redox compounds and the likes, in the release polymer can be modified by the application of reagent compositions with release polymers that comprise both a fast release polymer and a sustained release polymer. The fast release polymer and sustained release polymer can be applied together, or separately, in discrete areas of the working area to achieve the desired rate of release of reagents.

The character of the release polymer can be further influenced, that is adjusted to a desired rate, by the addition of one or more pore formers which can be inorganic or organic, and include materials that can be dissolved, extracted or leached from the coating when in contact with the biological fluid to be tested for an analyte. Upon exposure to the biological fluid to be tested, the pore-formers are dissolved and channels and pores are formed that fill with the biological fluid.

The pore formers of the release polymer comprise one or more water-soluble hydrophilic polymers in order to modify the release characteristics of the formulation. Examples of suitable hydrophilic polymers include hydroxypropylmethylcellulose, cellulose ethers and protein-derived materials. Of these polymers, the cellulose ethers, especially hydroxyalkylcelluloses and carboxyalkylcelluloses, are preferred. Also, synthetic water-soluble polymers can be used, such as polyvinylpyrrolidone, cross-linked polyvinylpyrrolidone, polyethylene oxide, etc., water-soluble polydextrose, saccharides and polysaccharides, such as pullulan, dextran, sucrose, glucose, fructose, mannitol, lactose, mannose, galactose, sorbitol, trehalose and the like In certain preferred embodiments of the disclosure, the hydrophilic polymer comprises hydroxypropylmethylcellulose.

Other pore formers which can be useful in the formulations in accordance to the embodiments include starch, modified starch, and starch derivatives, gums, including but not limited to xanthan gum, alginic acid, other alginates, bentonite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambdacarrageenan, gum karaya and biosynthetic gum. Other pore-formers include materials useful for making microporous lamina in the environment of use, such as polycarbonates comprised of linear polyesters of carbonic acid in which carbonate groups reoccur in the polymer chain, microporous materials such as bisphenol, a microporous poly(vinylchloride), microporous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly(vinylpyrrolidone).

In general, the amount of pore former included in the reagent compositions in accordance to the embodiments can be from about 0.1% to about 80%, by weight, relative to the combined weight of release polymers. In some embodiments the amount of pore former included in the reagent composition in accordance to the embodiments can be from about 0.1% to about 70%, from about 0.1% to about 60%, from about 0.1% to about 50%, from about 0.1% to about 40%, from about 0.1% to about 30%, from about 0.1% to about 25%, from about 0.1% to about 20%, from about 0.1% to about 15%, from about 0.1% to about 10%, from about 0.3% to about 10%, from about 0.5% to about 10%, from about 0.5% to about 8%, from about 0.5% to about 6%, from about 0.5% to about 4%, from about 1% to about 3% or from about 1% to about 2%.

Optionally, the reagent composition can further include a starch component, a plasticizer, humectant, adjuvant or mixtures thereof, and other excipients in suitable amounts, and which can be determined by one of skill in the art.

Redox Compounds

The reagent composition of some examples in accordance to the embodiments can include a redox compound such as an electron transfer agent. Certain embodiments use a redox compound that is a transition metal compound or transition metal complex. Examples of suitable transition metal compounds or transition metal complexes include osmium, ruthenium, iron, nickel and cobalt compounds or complexes. In these complexes, the transition metal is coordinatively bound to one or more ligands, which are typically mono-, di-, tri-, or tetradentate. The redox compound can be a polymeric redox compound, or, a redox polymer (i.e., a polymer having one or more redox species). Examples of suitable redox compounds and redox polymers are disclosed in U.S. Pat. Nos. 6,338,790 (Feldman, et al.), 6,605,200 (Mao, et al.) and 6,605,201 (Mao, et al.) and U.S Patent Publication 2006/0201805 (Forrow, et al.), all of which are incorporated by reference in their entirety. In case of conflict, the present application will control.

The metal ions suitable for use in accordance to the embodiments include, but are not limited to, nickel, manganese, zinc, iron, ruthenium, cobalt, osmium, nickel, copper, rhenium, rhodium, iridium, chromium and technetium.

In some embodiments of the disclosure the redox compounds include, but are not limited to, salts of the hexacyanometallates such as $[Fe(CN)_6]^{3-}$ (ferricyanide), $[Mo(CN)_6]^{3-}$ (hexacyanomolybdate), $[W(CN)_6]^{3-}$ (hexacyanotungstate) and $[Ru(CN)_6]^{3-}$ (hexacyanoruthenate). Other cyano coordination complexes that are derivatives of ferricyanide such as nitroprusside $[Fe(NO)(CN)_5]^{2-}$ and $[Fe(NH_3)(CN)_5]^{2-}$, $[Fe(H_2O)(CN)_5]^{2-}$, $[Fe(bpy)(CN)_4]^-$, $[Fe(bpy)_2(CN)_2]^+$, $[Fe(phen)(CN)_4]^-$, $[Fe(phen)_2(CN)_2]^+$, wherein:

phen is 1,10-phenanthroline:

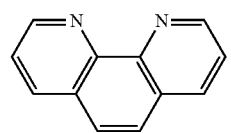

and bpy is 2,2'-bipyridine:

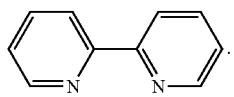

Other embodiments of the disclosure include, but are not limited to, redox compounds such as [Ru(NH$_3$)$_6$]Cl$_3$ (hexaammine ruthenium(III)), [Ru(NH$_3$)$_5$(pyridine)]Cl$_3$, [Ru(NH$_3$)$_4$(bpy)]Cl$_3$, [Ru(NH$_3$)$_4$(phen)]Cl$_3$ and transition metal complexes comprising charged ligands, such as [Ru(NH$_3$)$_4$(L)]Cl$_3$ wherein L is N-methyl-4,4'-bipyridinium.

In some embodiments the redox compound includes, but is not limited to, salts such as [Ni(PQ)$_3$]Cl$_2$, [Ni(PQ)$_3$]Br$_2$, [Ni(PQ)$_3$]SO$_4$ and [Ni(PQ)$_3$](NO$_3$)$_2$ where PQ is:

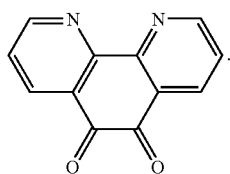

In other embodiments of the disclosure the redox compound can comprise transition metal salt complexes of Os with nitrogen containing ligands such as 2,2'-bipyridine, phenanthroline, biimidazole and pyridine, as those disclosed in U.S. Pat. Nos. 5,393,903, (Grätzel, et al.), 5,589,326 (Deng, et al.), 6,338,790 (Feldman, et al.) and 6,676,816 (Mao, et al.) which are incorporated by reference herein in their entirety. In case of conflict, the present application will control.

At least some Os-containing metal complexes include, but are not limited to, one or more pyridine or imidazole ligands. The imidazole ligand can also include other substituents and can be, for example, vinyl imidazole, e.g., 1-vinyl imidazole, or methylimidazole, e.g., 1-methylimidazole. Examples of suitable diffusible mediators can include [Os(dmo)$_2$(1-vinyl imidazole)X]X, [Os(dmo)$_2$(1-vinyl imidazole)X]X$_2$, [Os(dmo)$_2$(imidazole)X]X, [Os(dmo)$_2$(imidazole)X]X$_2$, [Os(dmo)$_2$(1-methylimidazole)X]X$_2$, and [Os(dmo)$_2$(methylimidazole)X]X$_2$, wherein dmo is 4,4'-dimethoxy-2,2'-bipyridine, and X is halogen.

Other osmium-containing redox compounds include, but are not limited to,

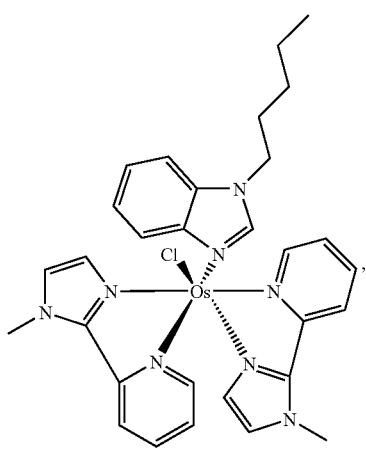

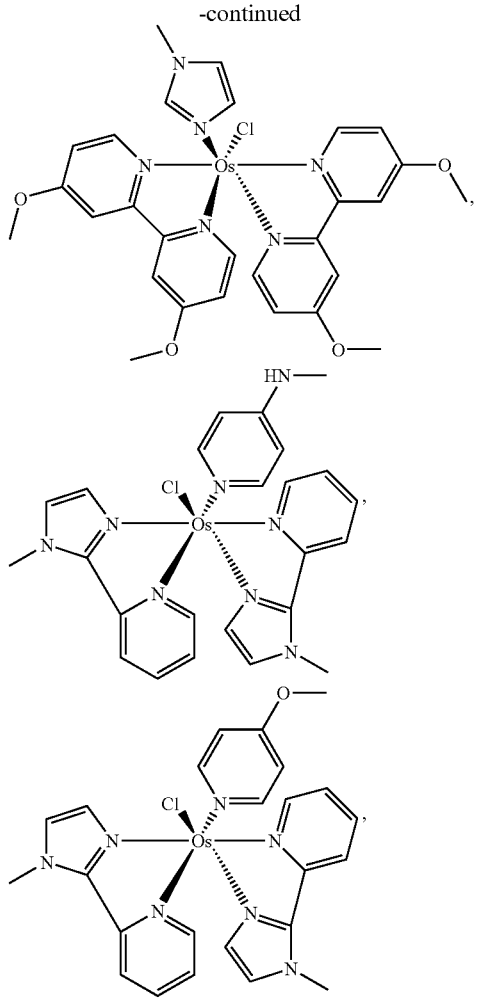

[Os((4,7-dimethoxy-1,10-phenanthroline)$_2$(N-methylimidazole)X]$^{+/2+}$; [Os((acetamido)$_2$bipyridine)$_2$(L)X]$^{+/2+}$, where L is a monodentate nitrogen-containing compound (including an imidazole derivative) chosen to refine the potential; and Os(terpyridine)(L)$_2$Cl, where L is an aminopyridine, such as a dialkylaminopyridine; an N-substituted imidazole, such as N-methyl imidazole; an oxazole; a thiazole; or an alkoxypyridine, such as methoxypyridine and X is halogen.

In other embodiments the redox compound comprises organic redox compounds such as 1,10-phenanthroline-5,6-dione (PQ) described above or 4,7-phenanthroline-5,6-dione:

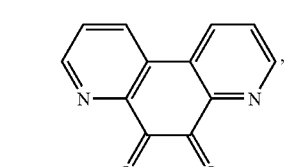

1,7-phenanthrolinequinone-5,6-dione:

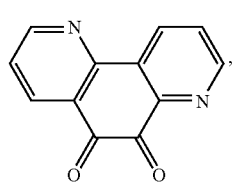

benzoquinone:

1,2-naphthoquinone:

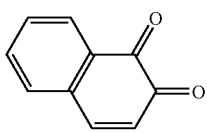

and derivatives and mixtures thereof.

In yet other embodiments, the redox compound comprises organic redox compounds such as phenazine methosulfate (PMS),

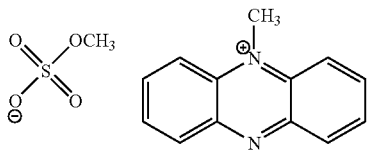

and derivatives thereof such as 1-methoxy phenazine methosulfate (MeO-PMS). Other embodiments include 2,6-dichlorophenol indophenol (DCIP):

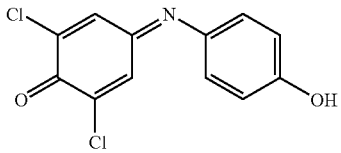

and other derivatives of indophenol.

The redox mediator, whether it is diffusible or not, mediates a current between working electrode and the analyte and enables the electrochemical analysis of molecules which may not be suited for direct electrochemical reaction on an electrode. The mediator functions as an agent to transfer electrons between the electrode and the analyte.

In some embodiments of the disclosure a redox compound can perform two roles in the biosensor. In the first role the redox compound can act as a redox mediator for a working electrode. Upon contact of biological fluid, for example blood, with the reagent layer, the redox mediator can be reduced by an enzyme cofactor, for example NAD(P)H, FADH$_2$ or PQQH$_2$, formed as a consequence of the reaction of the enzyme, for example GDH, with glucose. The reduced redox mediator that can be generated by the interaction with enzyme cofactor can then be oxidized at the working electrode. An appropriate potential is applied to the working electrode versus a reference electrode. Electrical neutrality is maintained by an opposite reaction of the redox compound at the reference/counter electrodes compared to the working electrode.

In the second role the redox compound can act as a redox couple for the reference/counter electrodes. The redox couple can simultaneously be reduced at the reference/counter electrodes. This interaction can balance the oxidation of the redox compound at the working electrode. In some embodiments the working, reference and counter electrodes are separated in a three-electrode system for example in U.S. Pat. No. 6,863,800 (Karinka, et al.) which is incorporated herein by reference. Typically, the amount of redox compound being oxidized at the working electrode can be monitored and the resulting current is related to the amount of glucose in the test sample to yield a test reading.

These reactions are further exemplified in FIG. 1. A biosensor with an overall complex redox mechanism 50 includes a $[Ni(PQ)_3]^{2+}$ redox compound and a GDH enzyme in conjunction with a $NAD(P)^+$, FAD or PQQ cofactor to test for the analyte glucose as illustrated. A biological fluid containing glucose is subjected to GDH enzyme cycle 59 in conjunction with the cofactors $NAD(P)^+$, FAD or PQQ. This causes cofactor cycle 57 $NAD(P)^+$, FAD or PQQ cofactors to produce reduced cofactors NAD(P)H, FADH$_2$ or PQQH$_2$. Reduced cofactors NAD(P)H, FADH$_2$ or PQQH$_2$ further react with the oxidized redox mediator 58b in mediator cycle 55 to produce reduced redox mediator 56b. Reduced redox mediator 56b interacts with working electrode 54 to produce oxidized redox mediator 58b and a current proportional to the amount of glucose in the biological fluid.

Concurrently with the reaction at the working electrode, the reference/counter electrode cycle 53 can take place. Oxidized redox couple 58a interacts with reference/counter electrode 52 to produce reduced redox couple 56a.

Enzymes and Coenzymes

NAD- and NADP-dependent enzymes are of great interest insofar as many have substrates of clinical value, such as glucose, D-3-hydroxybutyrate, lactate, ethanol, and cholesterol. Amperometric electrodes for detection of these substrates and other analytes can be designed by incorporating this class of enzymes and establishing electrical communication with the electrode via the mediated oxidation of the reduced cofactors NADH and NADPH.

NAD- and NADP-dependent enzymes are generally intracellular oxidoreductases (EC 1.x.x.x). The oxidoreductases are further classified according to the identity of the donor group of a substrate upon which they act. For example, oxidoreductases acting on a CH—OH group within a substrate are classified as EC 1.1.x.x whereas those acting on an aldehyde or keto-group of a substrate are classified as EC 1.2.x.x. Some important analytes (e.g., glucose, D-3-hydroxybutyrate, lactate, ethanol, and cholesterol) are substrates of the EC 1.1.x.x enzymes.

TABLE 1

| Classification | Enzyme |
| --- | --- |
| 1.1.1.1 | alcohol dehydrogenase |
| 1.1.1.27 | lactate dehydrogenase |
| 1.1.1.31 | 3-hydroxybutyrate dehydrogenase |
| 1.1.1.49 | glucose-6-phosphate dehydrogenase |
| 1.1.1.47 | glucose dehydrogenase |
| 1.2.1.46 | formaldehyde dehydrogenase |
| 1.1.1.37 | malate dehydrogenase |
| 1.1.1.209 | 3-hydroxysteroid dehydrogenase |

The category of oxidoreductases is also broken down according to the type of acceptor utilized by the enzyme. The enzymes of relevance in accordance to the embodiments have $NAD^+$ or $NADP^+$ as acceptors, and are classified as EC 1.x.1.x.

Colorants

In accordance with other embodiments, the reagent composition can include a colorant. The colorant can be added to the reagent composition in such amounts that the visibility of the reagent composition film formed is enhanced compared with the reagent composition film without a colorant. Enhanced visibility of the reagent film can be useful in conducting quality control measurement in manufacturing. For example, enhanced visibility of the reagent film can be used for automated in-line monitoring of coating weights. Enhanced visibility of the reagent composition can also be used for automated in-line monitoring of down-web and cross-web coating uniformity, for example, to detect coating defects such as pinholes or foreign objects. In yet other embodiments the inclusion of colorants in the reagent composition can also be used for automated in-line monitoring of the placement of the reagent composition, for example, to assure proper location of the reagent composition with respect to the electrodes to be coated with the reagent composition.

Colorants used in accordance with the embodiments can be compatible with other elements in the reagent composition. For example, the colorant can be chosen to be compatible with the functionality and chemistry of the mediator compound so as not to lead to erroneous or inconsistent test results of the analyte in the biological fluid to be tested.

Examples of colorants in accordance with the embodiments that can be included in the reagent composition include, but are not limited to, flavin mononucleotide (FMN), flavin adenine dinucleotide (FAD), erioglaucine (disodium and diamonium salts), D&C Red No. 22, D&C Yellow No. 10, FD&C Yellow No. 5, D&C Green No. 8, D&C Red No. 28, FD&C Red No. 3, meldola blue, $Fe(phen)_3Cl_2$, $Fe(bpy)_3Cl_2$, Nile blue A, methylene blue, FD&C Green No. 3, carminic acid, Naphthol Yellow S, Orange II, Allura Red AC, D&C Yellow No. 8, D&C Green No. 5 and mixtures thereof.

Biosensor Electrodes

Commercially available electrochemical biosensor strips for determining the concentration of glucose can employ two electrodes. In a two-electrode system, there are (1) a working electrode and (2) a dual-purpose reference/counter electrode. The second electrode is called a dual-purpose reference/counter electrode because this electrode acts as a reference electrode as well as a counter electrode. No current passes through an ideal reference electrode, and such an electrode maintains a steady potential; current does pass through a dual-purpose reference/counter electrode, and thus, the dual-purpose reference/counter electrode does not maintain a steady potential during the measurement. At low currents and/or at short durations of time for measurement, the shift in potential is small enough such that the response at the working electrode is not significantly affected, and hence the dual-purpose reference/counter electrode is designated a dual-purpose reference/counter electrode.

The dual-purpose reference/counter electrode continues to carry out the function of a counter electrode; however, in this case, the potential that is applied between the dual-purpose reference/counter electrode and the working electrode cannot be altered to compensate for changes in potential at the working electrode. In other words, while conventional electrochemical measurements require three electrodes, in all commercially available biosensor strips, there are only two electrodes, wherein one of the electrodes performs two functions—the reference function and the counter function.

As indicated previously, a reference electrode provides a reference for the voltage applied at the working electrode. The voltage applied must be sufficient to oxidize or reduce the species (molecule or ion) of interest at the surface of the working electrode. The voltage required is determined by the ease of removing or adding an electron to the species of interest. Because this voltage is applied externally (by means of a potentiostat or battery), the reference point is maintained at a constant value. If the value of the reference point changes with time, the external voltage applied should be varied accordingly.

Commercially available biosensor strips are very sensitive to the quality of the electrode that performs two functions (the reference function and the counter function). If that electrode is of poor quality, the voltage applied at the working electrode (by means of a battery or potentiostat) will not be maintained at a constant value, resulting in variation in the response of the biosensor strip from sample to sample. This variation depends on the hematocrit (which affects solution resistance) and concentration of the analyte (which affects current). In most electrochemical measurements, the current is measured at a constant applied voltage.

In a biosensor strip, the electrodes are separated from each other. The space between the electrodes results in the loss of voltage control at the working electrode. The voltage experienced at the working electrode therefore is lower than that applied. The difference between the voltage applied and the voltage experienced at the working electrode is a product of the current passing between the dual-purpose reference/counter electrode and the working electrode and the resistance of the solution. Also, on account of the current passing through the circuit, the dual-purpose reference/counter electrode becomes polarized. In other words, the flow of current through the dual-purpose reference/counter electrode brings about a reduction reaction at the electrode, thereby changing the chemical composition of the dual-purpose reference/counter electrode. This change in chemical composition brings about a change in the potential at the dual-purpose reference/counter electrode, and hence a change in the voltage applied.

Biosensors in accordance to the embodiments can have three electrodes: (1) a working electrode, (2) a reference electrode, and (3) a counter electrode. The reaction that takes place at the working electrode is the reaction that is required to be monitored and controlled. The functions of the reference and counter electrodes are to ensure that the working electrode actually experiences the correct potential intended to be applied. The function of the reference electrode is to measure the potential at the interface of the working electrode and the sample as accurately as possible. In an ideal situation, no current passes through the reference electrode. The function of the counter electrode is to ensure that the correct potential difference between the reference electrode and the working electrode is being applied. The potential difference between the working electrode and the reference electrode is assumed to be the same as the desired potential at the working electrode. If the potential measured at the working electrode is not the potential desired at the working electrode, the potential that is applied between the counter electrode and working electrode is either increased or decreased. The reaction at the counter electrode is also equal and opposite to the charge transfer reaction occurring at the working electrode. For example, if an oxidation reaction is occurring at the working electrode then a reduction reaction will take place at the counter electrode, thereby allowing the sample to remain electrically neutral.

In another embodiment of the disclosure, a biosensor comprises a trigger electrode. A trigger electrode is an electrode that assures that the assay is initiated only when the sample cell of the biosensor is in contact with biological fluid, for example blood. The trigger electrode can be positioned at a point distal to the sample entry point and downstream from the reference electrode, thus assuring that the assay is not initiated prior to the sample cell being in contact with biological fluid. Trigger electrodes improve accuracy and reproducibility of testing outcomes. U.S. Pat. No. 7,312,042 (Petyt, et al.) and U.S. Patent Publication No. 2006/0201805 (Forrow, et al.) describe trigger electrodes and are incorporated herein by reference in their entirety.

Figure 2:
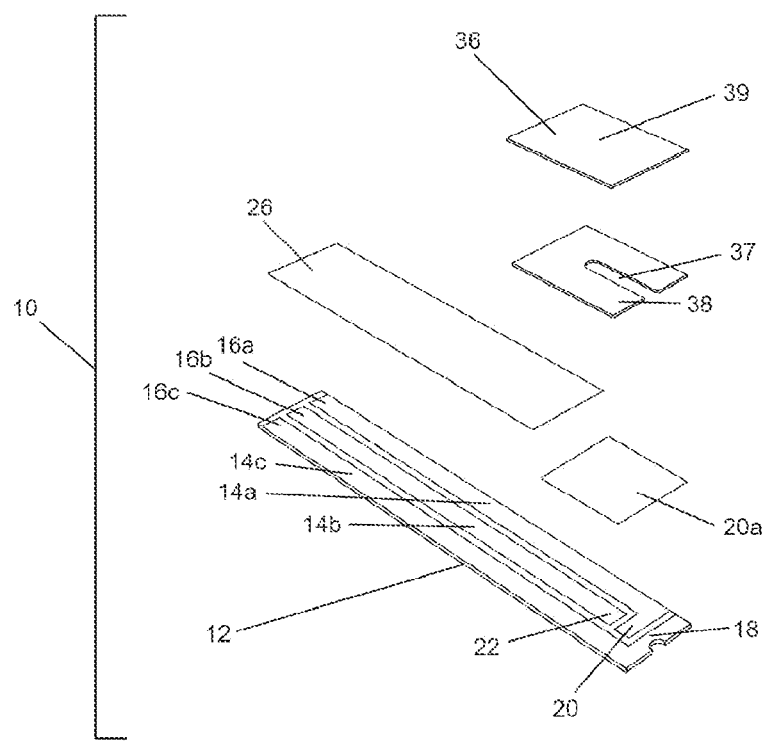
FIG. 2 is a perspective exploded view of one embodiment of a biosensor having a working electrode and a reference electrode and a counter electrode, in accordance to the embodiments.
Figure 3:
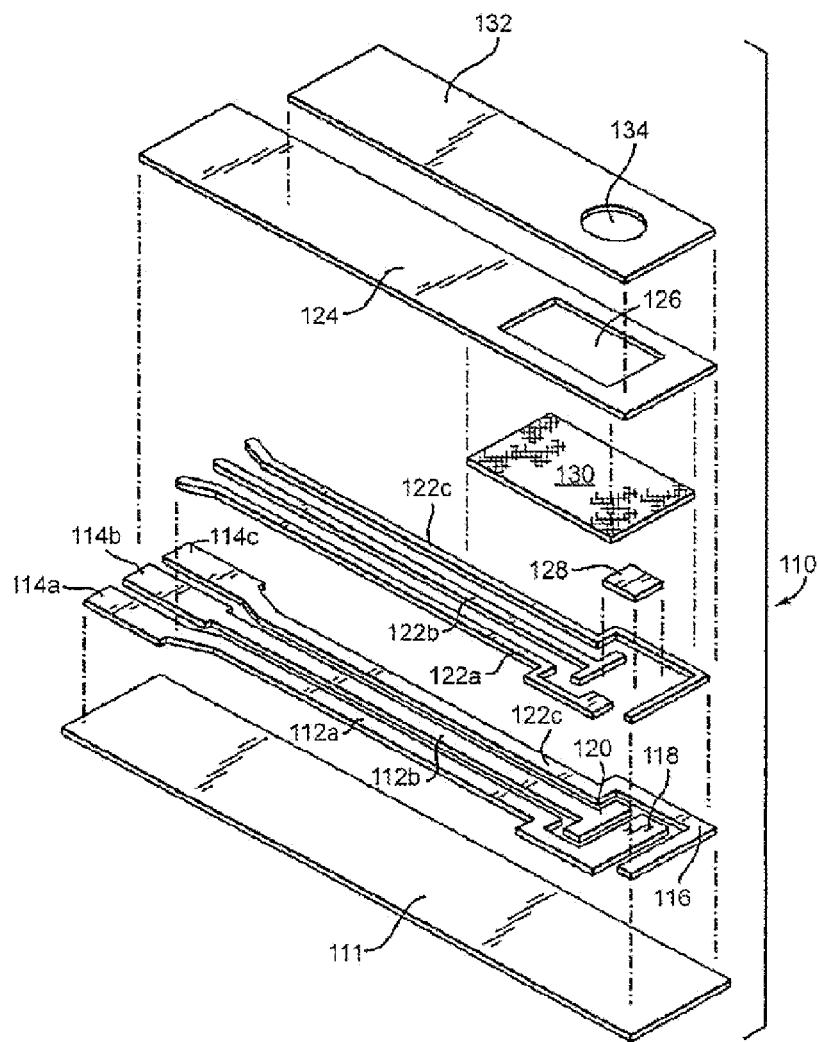
FIG. 3 is a perspective exploded view of one embodiment of a biosensor having a working electrode, a reference electrode and a counter electrode, in accordance to the embodiments.

Biosensor strips suitable in accordance to the embodiments are illustrated in FIGS. 2 and 3. Referring to FIG. 2, a biosensor strip 10 comprises an electrode support 12, e.g., an elongated strip of polymeric material (e.g., polyvinyl chloride, polycarbonate, polyester, or the like) supports three tracks 14a, 14b, and 14c of electrically conductive material, e.g., including gold. These tracks 14a, 14b, and 14c determine the positions of electrical contacts 16a, 16b, and 16c, a reference electrode 18, a working electrode 20, and a counter electrode 22. The electrical contacts 16a, 16b, and 16c can be inserted into an appropriate measurement device (not shown) for measurement of current.

The working electrode 20, reference electrode 18, and a counter electrode 22 include a layer of conductive material overlaid with a reagent composition film 20a. The reagent composition film 20a can be formed from a reagent composition, which is deposited, for example, by coating methods described herein, on the layer of conductive material of the working electrode 20, reference electrode 18, and a counter electrode 22. The reagent composition can include a mixture of a release polymer, a redox compound, an enzyme, and an enzyme cofactor.

A layer of a hydrophobic electrically insulating material 26 further overlies the tracks 14a, 14b, and 14c. The function of the hydrophobic electrically insulating material 26 is to prevent damage to and electrical short-circuiting (by any conducting fluid such as the sample to be analyzed) of the tracks 14a, 14b and 14c. A preformed capillary cell is constructed from a spacer layer 38 with a die-cut slot 37 surmounted by cover layer 36 and overlies the reagent composition film 20a. The cover layer 36 can optionally be made of a transparent or translucent material to aid the user in seeing that the biological fluid has fully entered the slot 37 which defines the sample chamber for receipt of the biological fluid to be analyzed. Additionally, the cover layer 36 has a pinhole 39. The positions of the reference electrode 18, the working electrode 20, the counter electrode 22, and the electrical contacts 16a, 16b, and 16c are not covered by the layer of hydrophobic electrically insulating material 26. In some embodiments of the biosensor strip 10 of FIG. 2, the identity of the electrodes 18 and 22 can be interchanged, that is, electrode 18 functions as the counter electrode and electrode 22 functions as the reference electrode. In other embodiments of the biosensor strip 10 of FIG. 2, the electrode 22 can serve as a trigger electrode in conjunction with its use as either a counter or reference electrode. The functions of the electrodes 18, 20 and 22 are determined by the electronic meter into which the contacts 16a, 16b and 16c of the biosensor strip 10 are inserted.

A biosensor strip 110 suitable for this invention is illustrated in FIG. 3. Referring to FIG. 3, an electrode support 111, such as an elongated strip of polymeric material (e.g., polyvinyl chloride, polycarbonate, polyester, or the like) supports three tracks 112a, 112b, and 112c of electrically conductive ink, such as carbon. These tracks 112a, 112b, and 112c determine the positions of electrical contacts 114a, 114b, and 114c, a reference electrode 116, a working electrode 118, and a counter electrode 120. The electrical contacts 114a, 114b, and 114c are insertable into an appropriate measurement device (not shown) for measurement of current.

Each of the elongated portions of the conductive tracks 112a, 112b, and 112c can optionally be overlaid with a track 122a, 122b, and 122c of conductive material, for example made of a mixture including silver particles and silver chloride particles. The enlarged exposed area of track 122c overlies the reference electrode 116. A layer of a hydrophobic electrically insulating material 124 further overlies the tracks 112a, 112b, and 112c. The positions of the reference electrode 116, the working electrode 118, the counter electrode 120, and the electrical contacts 114a, 114b, and 114c are not covered by the layer of hydrophobic electrically insulating material 124. An exemplary insulating material 124 is "POLYPLAST" or "SERICARD" (both available from Sericol Ltd., Broadstairs, Kent, UK). This hydrophobic electrically insulating material 124 serves to prevent short circuits. The layer of hydrophobic electrically insulating material 124 has an opening 126 formed therein. This opening 126 provides the boundary for the reaction zone of the biosensor strip 110. Because this insulating material is hydrophobic, it can cause the sample to be restricted to the portions of the electrodes in the reaction zone. The working electrode 118 comprises a layer of a non-reactive electrically conductive material on which is deposited a layer 128 containing a reagent composition for carrying out an oxidation-reduction reaction. At least one layer of mesh 130 overlies the electrodes. This layer of mesh 130 protects the printed components from physical damage. The layer of mesh 130 also helps the sample to wet the electrodes by reducing the surface tension of the sample, thereby allowing it to spread evenly over the electrodes. A cover 132 encloses the surfaces of the electrodes that are not in contact with the electrode support 111. This cover 132 is a liquid impermeable membrane. The cover 132 includes a small aperture 134 to allow access of the applied sample to the underlying layer of mesh 130.

The reagent composition 128 is deposited on that portion of the electrically conductive material of the working electrode 118 where the oxidation-reduction reaction is to take place when a sample is introduced to the biosensor strip 110. In such embodiments, the reagent composition 128 can be applied to the working electrode 118 as a discrete area having a fixed length. Typical analytes of interest include, for example, glucose, cholesterol and ketone bodies. Typical non-reactive electrically conductive materials include, for example, carbon, platinum, palladium, iridium, and gold. A semiconducting material such as indium doped tin oxide can be used as the non-reactive electrically conductive material. In certain embodiments, the reagent composition comprises a mixture of a release polymer, a mediator compound and an enzyme. Alternatively, instead of an enzyme, the reagent composition can contain a substrate that is catalytically reactive with an enzyme to be assayed. In the biosensor strips of this invention, the reagent(s) are applied in the form of a composition containing particulate material and having binder(s), and, accordingly, does not dissolve rapidly when subjected to the sample. In view of this feature, the oxidation-reduction reaction will occur at the interface of working electrode 118 and the sample. The glucose molecules diffuse to the surface of the working electrode 118 and react with the enzyme/mediator compound mixture.

In other embodiments, in addition to being applied to the working electrode 118, a layer of the reagent composition can be applied to any of the other electrodes, such as the reference electrode when desired, as a discrete area having a fixed length.

In yet other embodiments the biosensor can include an optical sensor. An optical sensor can have a multiple-layer element formed by the reagent composition film, a base layer and an optical measurement window. The reagent composition film may contain an enzyme, for example, such as an oxidase or a dehydrogenase and a dye that changes color as a result of the ensuing reaction of the enzyme with the analyte. Examples of the enzymes and the dyes that can be used for this application are described in U.S. Pat. No. 5,304,468 (Phillips et al.) which is included herein by reference in its entirety. The multi-layer assembly can further contain an opening and a flow channel leading to the optical measurement window. The sample will flow to the measurement window and react with reagents resulting in a change in color. The change in color is measured using a photometric measurement device, the details of which are further described in U.S. Pat. No. 6,077,660 (Wong et al.), which is included herein by reference in its entirety.

Figure 32:
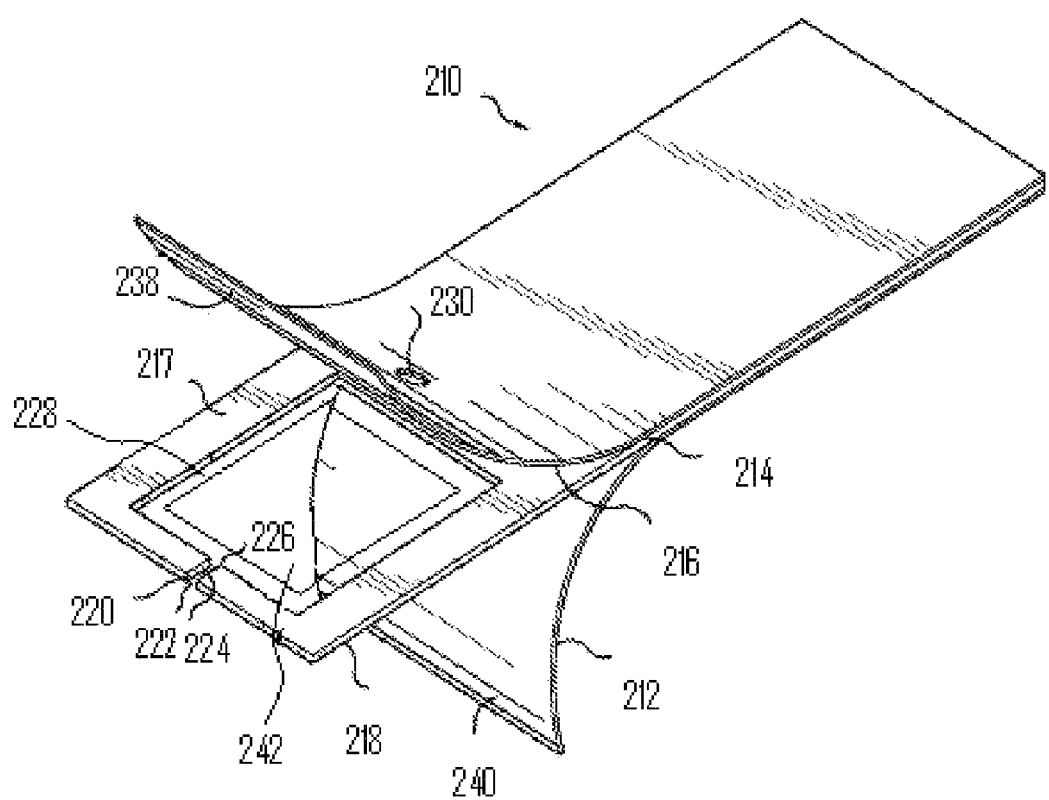
FIG. 32 is a perspective view of an optical sensor in accordance to the embodiments, with layers shown peeled-apart.

Referring now to FIG. 32, the optical sensor article 210 comprises a base layer 212, overlying the base layer 212a core layer 214, and overlying the core layer 214a cover layer 216. The core layer 214 has a first major surface 217 and a second major surface 218. The core layer 214 comprises an application site 220 communicating with a first end 222 of a flow channel 224. The flow channel 224 has a second end 226, which communicates with an optical reading chamber 228 containing a reagent composition film 242. The cover layer 216 has an opening 230, which serves as a vent. This embodiment has a base layer 212 below the core layer 214, because the optical reading chamber 228 extends all the way through the core layer 214. A first major surface 238 of the cover layer 216 is in face-to-face contact with major surface 217 of the core layer 214. A first major surface 240 of the base layer 212 is in face-to-face contact with major surface 218 of the core layer 214.

Figure 33:
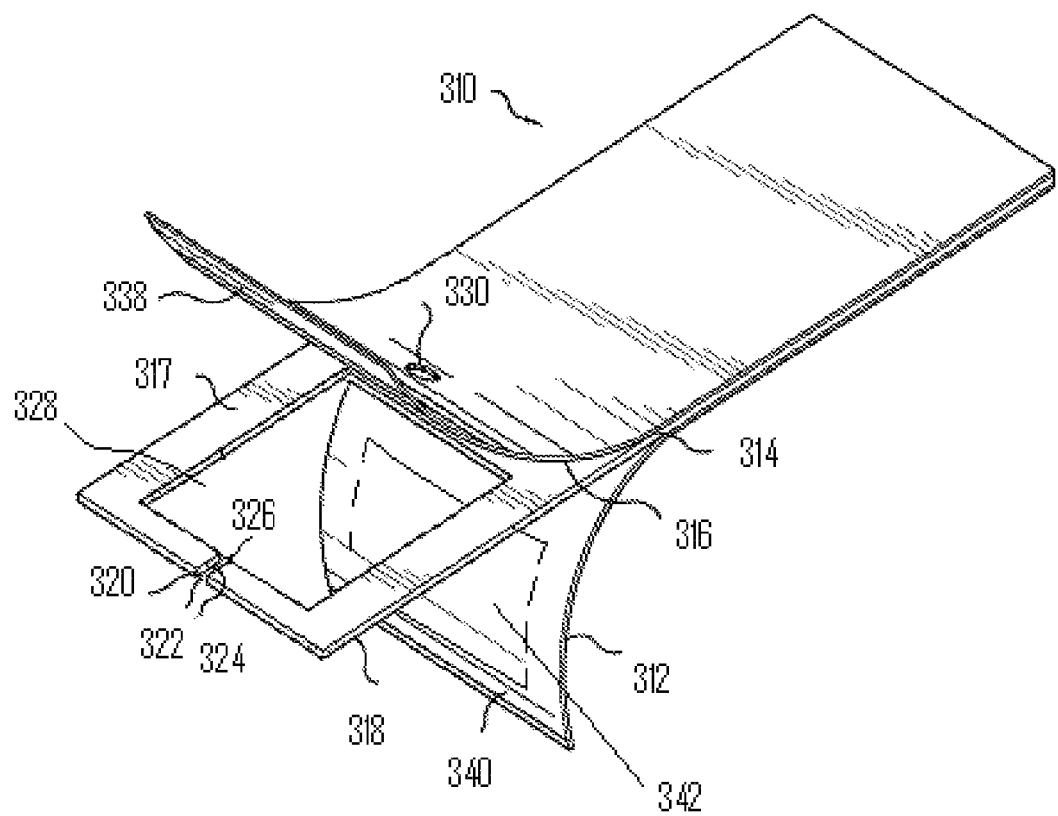
FIG. 33 is a perspective view of an optical sensor in accordance to the embodiments, with layers shown peeled-apart.

Referring now to FIG. 33, the optical sensor article 310 comprises a base layer 312, partially overlying the base layer 312 a reagent composition film 342 and a core layer 314, and overlying the core layer 314 a cover layer 316. The core layer 314 has a first major surface 217 and a second major surface 318. The core layer 314 comprises an application site 320 communicating with a first end 322 of a flow channel 324. The flow channel 324 has a second end 326, which communicates with an optical reading chamber 328. The cover layer 316 has an opening 330, which serves as a vent. This embodiment has a base layer 312 below the core layer 314, because the optical reading chamber 328 extends all the way through the core layer 314. A first major surface 338 of the cover layer 316 is in face-to-face contact with major surface 317 of the core layer 314. A first major surface 340 of the base layer 312 is in face-to-face contact with major surface 318 of the core layer 314.

Coating

The reagent composition in accordance to the embodiments can be coated using methods known to those skilled in the art appropriate for coating low viscosity, Newtonian solutions as described herein. Some examples of coating methods useful in making biosensors in accordance to the embodiments, but not limiting, are ink jet coating methods, slot die coating methods, drop coating methods, hand coating methods, squeegee coating methods, spray coating methods, rod coating methods, roll coating methods, dip coating methods, meter rod coating methods, spin coating methods, curtain coating methods, slide coating methods or combination thereof.

After coating the reagent composition onto a substrate, the sample can be dried by $O_2$, $CO_2$, air, convection, radiant heat, for example infra-red, vacuum or combinations thereof.

In some examples in accordance to the embodiments the reagent composition films can be uniformly coated. A uniform coating can be any coating produced by the methods described herein whereby the reagent composition film produced can function in the operating environment of the biosensor in accordance to the embodiments.

Some embodiments of the reagent composition films in accordance to the embodiments will have a thickness in the range of from about 3 μm to about 12 μm, and others can be in the range of from about 3 μm to about 10 μm, from about 3 μm to about 8 μm, from about 3 μm to about 7 μm, from about 3 μm to about 6 μm, from about 3 μm to about 5 μm, from about 4 μm to about 6 μm, and in others from about 5 μm to about 6 μm. Various other thickness ranges can be suitable as desired for particular applications in combination with a variety of release polymers.

Transition Metal Complexes

The transition metal complexes of the present invention are effectively employed as redox mediators in electrochemical sensors, given their very fast kinetics. More particularly, when a transition metal complex of this invention is so employed, rapid electron exchange between the transition metal complex and the enzyme and/or the working electrode in the sensor device occurs. This electron exchange is sufficiently rapid to facilitate the transfer of electrons to the working electrode that might otherwise be transferred to another electron scavenger in the system. The fast kinetics of the mediator is generally enhanced when $L_2$ of a mediator of the formula provided above is a negatively charged ligand.

The transition metal complexes of the present invention are also quite stable. For example, when such a complex is used as a mediator in an electrochemical sensor, the chemical stability is generally such that the predominant reactions in which the mediator participates are the electron-transfer reaction between the mediator and the enzyme and the electrochemical redox reaction at the working electrode. The chemical stability may be enhanced when a mediator of the formula provided above, wherein $L_1$ is a negatively charged ligand, has a "bulky" chemical ligand, $L_1$, that shields the redox center, M, and thereby reduces undesirable chemical reactivity beyond the desired electrochemical activity.

The electrochemical stability of the transition metal complexes of the present invention is also quite desirable. For example, when such a complex is used as a mediator in an electrochemical sensor, the mediator is able to operate in a range of redox potentials at which electrochemical activity of common interfering species is minimized and good kinetic activity of the mediator is maintained.

Thus, the claimed subject matter provides enzyme-based electrochemical sensors comprising transition metal complexes with pyridyl-imidazole ligands, which show improved response times in the detection and quantification of fluid analytes. The claimed subject matter is also directed to the use of the complexes as redox mediators. The advantageous properties and characteristics of said transition metal complexes make them ideal candidates for use in the electrochemical sensing of glucose, an application of particular importance in the treatment of diabetes in human populations.

Generally, the present invention relates to enzyme-based electrochemical sensors comprising transition metal complexes of iron, cobalt, ruthenium, osmium, and vanadium. The invention also relates to the preparation of the transition metal complexes and to the use of the transition metal complexes as redox mediators. In at least some instances, the transition metal complexes have one or more of the following characteristics: redox potentials in a particular range, the ability to exchange electrons rapidly with electrodes, the ability to rapidly transfer electrons to or rapidly accept electrons from an enzyme to accelerate the kinetics of electrooxidation or electroreduction of an analyte in the presence of an enzyme or another analyte-specific redox catalyst. In some cases, the transition metal complex may be described as a coordination complex comprising osmium.

For example, a redox mediator may accelerate the electrooxidation of glucose in the presence of glucose oxidase, FAD-glucose dehydrogenase or PQQ-glucose dehydrogenase, a process that can be useful for the selective assay of glucose in the presence of other electrochemically oxidizable species. Some embodiments of the invention may be easier or more cost-effective to make synthetically, or more cost-effective reagents in synthesis than other transition metal redox mediators.

Compounds having Formula 1, set forth below, are examples of transition metal complexes of the present invention.

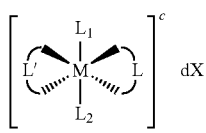

Formula 1

M is a transition metal and is typically iron, cobalt, ruthenium, osmium, or vanadium. Ruthenium and osmium are particularly suitable for redox mediators.

L and L' are each bidentate, substituted or unsubstituted 2-(2-pyridyl)imidazole ligands having the Structure 2 set forth below.

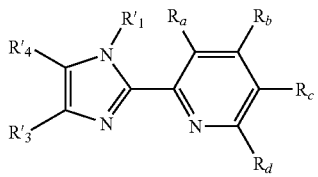

Formula 2

In Formula 2, $R'_1$ is a substituted or an unsubstituted aryl, alkenyl, or alkyl. Generally, $R'_1$ is a substituted or an unsubstituted C1-C12 alkyl or alkenyl, or an aryl, such as phenyl, optionally substituted with a substituent selected from a group consisting of —Cl, —F, —CN, amino, carboxy, C1-C6 alkyl, C1-C6 alkylthio, C1-C6 alkylamino, C1-C6 dialkylamino, C1-C6 alkylaminocarbonyl, C1-C6 alkoxy, C1-C6 alkoxycarbonyl, and C1-C6 alkylcarboxamido. $R'_1$ is typically methyl or a C1-C12 alkyl that is optionally substituted with a reactive group, or an aryl optionally substituted with C1-C2 alkyl, C1-C2 alkoxy, —Cl, or —F.

Generally, $R'_3$, $R'_4$, $R_a$, $R_b$, $R_c$, and $R_d$ are independently —H, —F, —Cl, —Br, —I, —NO$_2$, —CN, —CO$_2$H, —SO$_3$H, —NHNH$_2$, —SH, —OH, —NH$_2$, substituted or unsubstituted alkoxylcarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl. Alternatively, $R_c$ and $R_d$ in combination and/or $R'_3$ and $R'_4$ in combination can form a saturated or unsaturated 5- or 6-membered ring. Typically, the alkyl and alkoxy portions are C1 to C12. The alkyl or aryl portions of any of the substituents are optionally substituted by —F, —Cl, —Br, —I, alkylamino, cnalkylamino, trialkylammonium (except on aryl portions), alkoxy, alkylthio, aryl, or a reactive group. Generally, $R'_3$, $R'_4$, $R_a$, $R_b$, $R_c$ and $R_d$ are independently —H or unsubstituted alkyl groups. Typically, $R_a$ and $R_c$ are —H and $R'_3$, $R'_4$, $R_b$, and $R_d$ are —H or methyl.

Preferably, the L and L' ligands are the same. Herein, references to L and L' may be used interchangeably.

In Formula 1, c is an integer indicating the charge of the complex. Generally, c is an integer selected from—+1 to +5 indicating a positive charge. For a number of osmium complexes, c is +1, +2, or +3.

X represents counter ion(s). Examples of suitable counter ions include anions, such as halide (e.g., fluoride, chloride, bromide or iodide), sulfate, phosphate, hexafluorophosphate, and tetrafluoroborate, and cations (preferably, monovalent cations), such as lithium, sodium, potassium, tetralkylammonium, and ammonium. Preferably, X is a halide, such as chloride. The counter ions represented by X are not necessarily all the same.

Generally, d represents the number of counter ions and is typically from 1 to 5.

$L_1$ and $L_2$ are ligands attached to the transition metal via a coordinative bond. $L_1$ and $L_2$ are monodentate ligands, at least one of which is a negatively charged monodentate ligand. While $L_1$ and $L_2$ may be used interchangeably, $L_2$ is generally referred to as a negatively charged ligand merely by way of convenience. Herein, the term "negatively charged ligand" is defined as a ligand in which the coordinating atom itself is negatively charged so that on coordination to a positively charged metal, the negative charge is neutralized. For example, a halide such as chloride or fluoride meets the present definition while a pyridine ligand bearing a negatively charged sulfonate group does not because the sulfonate group does not participate in coordination. Examples of negatively charged ligands include, but are not limited to, —F, —Cl, —Br, —I, —CN, —SCN, —OH, alkoxy, alkylthio, and phenoxide. Typically, the negatively charged monodentate ligand is a halide.

Examples of other suitable monodentate ligands include, but are not limited to, H$_2$O, NH$_3$, alkylamine, dialkylamine, trialkylamine, or heterocyclic compounds. The alkyl or aryl portions of any of the ligands are optionally substituted by —F, —Cl, —Br, —I, alkylamino, dialkylamino, trialkylammonium (except on aryl portions), alkoxy, alkylthio, aryl, or a reactive group. Any alkyl portions of the monodentate ligands generally contain 1 to 12 carbons. More typically, the alkyl portions contain 1 to 6 carbons. In other embodiments, the monodentate ligands are heterocyclic compounds containing at least one nitrogen, oxygen, or sulfur atom. Examples of suitable heterocyclic monodentate ligands include imidazole, pyrazole, oxazole, thiazole, triazole, pyridine, pyrazine and derivatives thereof. Suitable heterocyclic monodentate ligands include substituted and unsubstituted imidazole and substituted and unsubstituted pyridine having the general Formulas 3 and 4, respectively, as set forth below.

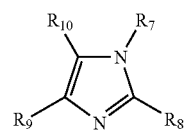

Formula 3

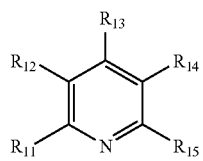

Formula 4

With regard to Formula 3, $R_7$ is generally a substituted or unsubstituted alkyl, alkenyl, or aryl group. Generally, $R_7$ is a substituted or unsubstituted C1 to C12 alkyl or alkenyl, or an aryl, such as phenyl, optionally substituted with a substituent selected from a group consisting of —Cl, —F, —CN, amino, carboxy, C1-C6 alkyl, C1-C6 alkylthio, C1-C6 alkylamino, C1-C6 dialkylamino, C1-C6 alkylaminocarbonyl, C1-C6 alkoxy, C1-C6 alkoxycarbonyl, and C1-C6 alkylcarboxamido. $R_7$ is typically methyl or a C1-C12 alkyl that is optionally substituted with a reactive group, or an aryl optionally substituted with C1-C2 alkyl, C1-C2 alkoxy, —Cl, or —F.

Generally, $R_8$, $R_9$ and $R_{10}$ are independently —H, —F, —Cl, —Br, —I, —NO2, —CN, —CO$_2$H, —SO$_3$H, —NHNH$_2$, —SH, —OH, —NH$_2$, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl. Alternatively, $R_9$ and $R_{10}$, in combination, form a fused 5- or 6-membered ring that is saturated or unsaturated. The alkyl portions of the substituents generally contain 1 to 12 carbons and typically contain 1 to 6 carbon atoms. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. In some embodiments, $R_8$, $R_9$ and $R_{10}$ are —H or substituted or unsubstituted alkyl. Preferably, $R_8$, $R_9$ and $R_{10}$ are —H.

With regard to Formula 4, $R_{11}$, $R_{12}$, $R_{13}$, $R_{14}$ and $R_{15}$ are independently —H, —F, —Cl, —Br, —I, —NO$_2$, —CN, —CO$_2$H, —OH, —NH$_2$, alkoxycarbonyl, alkylaminocarbonyl, dialkylaminocarbonyl, alkoxy, alkylamino, dialkylamino, alkanoylamino, arylcarboxamido, hydrazino, alkylhydrazino, hydroxylamino, alkoxyamino, alkylthio, alkenyl, aryl, or alkyl. The alkyl or aryl portions of any of the substituents are optionally substituted by —F, —Cl, —Br, —I, alkylamino, dialkylamino, trialkylammonium (except for aryl portions), alkoxy, alkylthio, aryl, or a reactive group. Generally, $R_{11}$, $R_{12}$, $R_{13}$, $R_{14}$ and $R_{15}$ are —H, methyl, C1-C2 alkoxy, C1-C2 alkylamino, C2-C4 dialkylamino, or a C1-C6 lower alkyl substituted with a reactive group.

One example includes $R_{11}$ and $R_{15}$ as —H, $R_{12}$ and $R_{14}$ as the same and —H or methyl, and $R_{13}$ as —H, C1 to C12 alkoxy, —NH$_2$, C1 to C12 alkylamino, C2 to C24 dialkylamino, hydrazino, C1 to C12 alkylhydrazino, hydroxylamino, C1 to C12 alkoxyamino, C1 to C12 alkylthio, or C1 to C12 alkyl. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group.

Examples of suitable transition metal complexes include bis[2-(1-methylimidazol-2-yl-$\kappa N^3$)pyridine-$\kappa N$]chloro(1-methylimidazolo-$\kappa N^3$)osmium(2+) dichloride (also written as [Os(Py-MIM)$_2$(MIM)Cl]$^{2+}$2Cl$^-$) where $L_1$ is

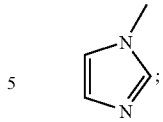

$L_2$ is Cl; c is +2; d is 2; X is Cl—; and L and L' are

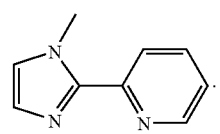

The transition metal complexes of Formula 1 may also include transition metal complexes that are coupled to a polymeric backbone through one or more of L, L', $L_1$, and $L_2$. In some embodiments, the polymeric backbone has at least one functional group that acts as a ligand of the transition metal complex. Such polymeric backbones include, for example, poly(4-vinylpyridine) and poly(N-vinylimidazole) in which the pyridine and imidazole groups, respectively, can act as monodentate ligands of the transition metal complex. In other embodiments, the transition metal complex can be the reaction product between a reactive group on a precursor polymer and a reactive group on a ligand of a precursor transition metal complex (such as complex of Formula 1 where one of L, L', $L_1$, and $L_2$ includes a reactive group, as described above). Suitable precursor polymers include, for example, poly (acrylic acid) (Formula 7), styrene/maleic anhydride copolymer (Formula 8), methylvinylether/maleic anhydride copolymer (GANTREZ polymer) (Formula 9), poly (vinylbenzylchloride) (Formula 10), poly(allylamine) (Formula 11), polylysine (Formula 12), carboxy-poly(vinylpyridine) (Formula 13), and poly(sodium 4-styrene sulfonate) (Formula 14). The numbers n, n' and n" appearing variously in these formulas may vary widely. Merely by way of example, in Formula 13, [n'/(n'+n")]×100% is preferably from about 5% to about 15%.

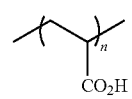

Formula 7

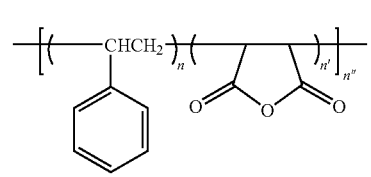

Formula 8

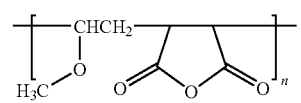

Formula 9

-continued

Formula 10

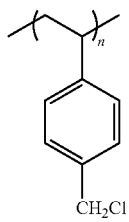

Formula 11

Formula 12

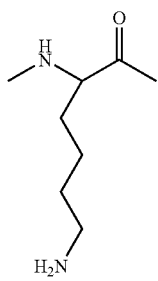

Formula 13

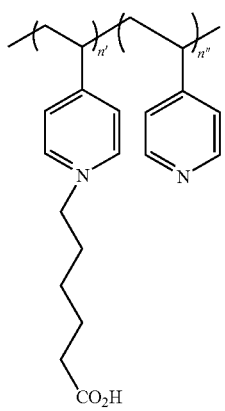

Formula 14

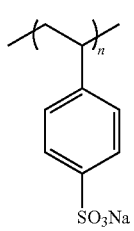

Alternatively, the transition metal complex can have one or more reactive group(s) for immobilization or conjugation of the complexes to other substrates or carriers, examples of which include, but are not limited to, macromolecules (e.g., enzymes) and surfaces (e.g., electrode surfaces).

For reactive attachment to polymers, substrates, or other carriers, the transition metal complex precursor includes at least one reactive group that reacts with a reactive group on the polymer, substrate, or carrier. Typically, covalent bonds are formed between the two reactive groups to generate a linkage. Examples of such reactive groups and resulting linkages are provided below. Generally, one of the reactive groups is an electrophile and the other reactive group is a nucleophile.

Examples of Reactive Groups and Resulting Linkages

| First Reactive Group | Second Reactive Group | Resulting Linkage |
|---|---|---|
| Activated ester* | Amine | Carboxamide |
| Acrylamide | Thiol | Thioether |
| Acyl azide | Amine | Carboxamide |
| Acyl halide | Amine | Carboxamide |
| Carboxylic acid | Amine | Carboxamide |
| Aldehyde or ketone | Hydrazine | Hydrazone |
| Aldehyde or ketone | Hydroxyamine | Oxime |
| Alkyl halide | Amine | Alkylamine |
| Alkyl halide | Carboxylic acid | Carboxylic ester |
| Alkyl halide | Imidazole | Imidazolium |
| Alkyl halide | Pyridine | Pyridinium |
| Alkyl halide | Alcohol/phenol | Ether |
| Alkyl halide | Thiol | Thioether |
| Alkyl sulfonate | Thiol | Thioether |
| Alkyl sulfonate | Pyridine | Pyridinium |
| Alkyl sulfonate | Imidazole | Imidazolium |
| Alkyl sulfonate | Alcohol/phenol | Ether |
| Anhydride | Alcohol/phenol | Ester |
| Anhydride | Amine | Carboxamide |
| Aziridine | Thiol | Thioether |
| Aziridine | Amine | Alkylamine |
| Aziridine | Pyridine | Pyridinium |
| Epoxide | Thiol | Thioether |
| Epoxide | Amine | Alkylamine |
| Epoxide | Pyridine | Pyridinium |
| Halotriazine | Amine | Aminotriazine |
| Halotriazine | Alcohol | Triazinyl ether |
| Imido ester | Amine | Amidine |
| Isocyanate | Amine | Urea |
| Isocyanate | Alcohol | Urethane |
| Isothiocyanate | Amine | Thiourea |
| Maleimide | Thiol | Thioether |
| Sulfonyl halide | Amine | Sulfonamide |

*Activated esters, as understood in the art, generally include esters of succinimidyl, benzotriazolyl, or aryl substituted by electron-withdrawing groups such as sulfo, nitro, cyano, or halo; or carboxylic acids activated by carbodiimides.

Transition metal complexes of the present invention can be soluble in water or other aqueous solutions, or in organic solvents. In general, the transition metal complexes can be made soluble in either aqueous or organic solvents by having an appropriate counter ion or ions, X. For example, transition metal complexes with small counter anions, such as $F^-$, $Cl^-$, and $Br^-$, tend to be water soluble. On the other hand, transition metal complexes with bulky counter anions, such as $I^-$, $BF_4^-$ and $PF_6^-$, tend to be soluble in organic solvents. Preferably, the solubility of transition metal complexes of the present invention is greater than about 0.1 M (moles/liter) at 25° C. for a desired solvent.

The transition metal complexes discussed above are useful as redox mediators in electrochemical sensors for the detection of analytes in biofluids. The use of transition metal complexes as redox mediators is described, for example, in U.S. Pat. Nos. 5,262,035, 5,320,725, 5,365,786, 5,593,852, 5,665, 222, 5,972,199, 6,134,161, 6,143,164, 6,175,752 and 6,338, 790 and U.S. patent application Ser. No. 09/434,026, all of which are incorporated herein by reference. The transition metal complexes described herein can typically be used in place of those discussed in the references listed above, although the results of such use will be significantly enhanced given the particular properties of the transition metal complexes of the present invention, as further described herein.

In general, the redox mediators of the present invention are disposed on or in proximity to (e.g., in a solution surrounding) a working electrode. The redox mediator transfers electrons between an analyte and a working electrode. In some preferred embodiments, an enzyme is also included to facilitate the transfer. For example, the redox mediator transfers electrons between glucose and the working electrode (typically via an enzyme) in an enzyme-catalyzed reaction of glucose. Redox polymers are also be particularly useful for forming non-leachable coatings on the working electrode. These can be formed, for example, by crosslinking the redox polymer on the working electrode, or by crosslinking the redox polymer and the enzyme on the working electrode.

Transition metal complexes can enable accurate, reproducible and quick or continuous assays. Transition metal complex redox mediators accept electrons from, or transfer electrons to, enzymes or analytes at a high rate and also exchange electrons rapidly with an electrode. Typically, the rate of self exchange, the process in which a reduced redox mediator transfers an electron to an oxidized redox mediator, is rapid. At a defined redox mediator concentration, this provides for more rapid transport of electrons between the enzyme (or analyte) and electrode, and thereby shortens the response time of the sensor. Additionally, the novel transition metal complex redox mediators are typically stable under ambient light and at the temperatures encountered in use, storage and transportation. Preferably, the transition metal complex redox mediators do not undergo chemical change, other than oxidation and reduction, in the period of use or under the conditions of storage, though the redox mediators can be designed to be activated by reacting, for example, with water or the analyte.

The transition metal complexes can be used as redox mediators in combination with redox enzymes to electrooxidize or electroreduce the analyte or a compound derived of the analyte, for example by hydrolysis of the analyte. The redox potentials of the redox mediators are generally more positive (i.e. more oxidizing) than the redox potentials of the redox enzymes when the analyte is electrooxidized and more negative when the analyte is electroreduced. For example, the redox potentials of the preferred transition metal complex redox mediators used for electrooxidizing glucose with glucose oxidase, FAD-glucose dehydrogenase or PQQ-glucose dehydrogenase as the enzyme is between about −200 mV and +200 mV versus a Ag/AgCl reference electrode, and the most preferred mediators have redox potentials between about −200 mV and about +100 mV versus a Ag/AgCl reference electrode.

EXAMPLES

General Fabrication Method and Testing of Hand-Coated Gold Electrodes

A gold electrode (about 5.5 mm×about 35 mm) was prepared by deposition of gold onto a web of polyethylene terephthalate (PET) substrate, followed by laser ablation of gold to create distinct electrodes. The distance between the gold electrodes was approximately 0.5 mm. Reagent formulations containing [Ni(PQ)$_3$]Cl$_2$, KOLLICOAT PROTECT®, MgCl$_2$, trehalose, NAD sodium salt and NAD-GDH (activity=114 U/mg) percent w/v as described in Table 2 were prepared. Reagent solutions were dispensed as a drop from an automatic pipette, equipped with plastic tip, onto the sample area of an individual gold electrode. The drop of reagent solution was then spread manually with the pipette tip over the full electrode width (5.5 mm) and partial length (6 mm) of the sample end of the electrode. Gold electrodes coated with reagent solution were dried in a fan-assisted oven at 75° C. for 3 min. The final electrode was obtained by applying a preformed die-cut capillary cell with a pinhole over the dried reagent layer and then trimming to size with scissors. The die-cut capillary cell comprises an opaque double-sided spacing layer (of defined thickness, usually approx. 100 μm) coated with pressure-sensitive adhesive (PSA) surmounted with a transparent hydrophilic polymer film. An oblique scissor cut was used to expose a small area of reagent layer as a sample application area at the end of the strip. This facilitated filling of the strip with test sample.

TABLE 2

Formulations for hand-coated gold electrodes of Examples 1-7 (% w/v).

| Material | Ex 1 | Ex 2 | Ex 3 | Ex 4 | Ex 5 | Ex 6 | Ex 7 |
|---|---|---|---|---|---|---|---|
| [Ni(PQ)$_3$]Cl$_2$ | 2.0 | 4.0 | 5.0 | 5.0 | 4.2 | 3.3 | 3.4 |
| KOLLICOAT PROTECT® | 1.0 | 2.0 | 3.0 | 3.0 | 2.5 | 2.0 | 2.0 |
| MgCl$_2$ | 1.0 | 2.0 | 1.0 | 1.0 | 0.8 | 0.7 | 0.7 |
| trehalose | *N/A | N/A | N/A | 7.0 | 5.8 | 4.7 | 4.7 |
| NAD, sodium salt | N/A | N/A | N/A | 1.0 | 0.8 | 0.7 | 0.7 |
| NAD-GDH | N/A | N/A | N/A | N/A | N/A | N/A | 0.7 |
| Total % solids | 4.0 | 8.0 | 9.0 | 17.0 | 14.1 | 11.4 | 12.2 |

*N/A indicates no additive

Example 8

Figure 4:
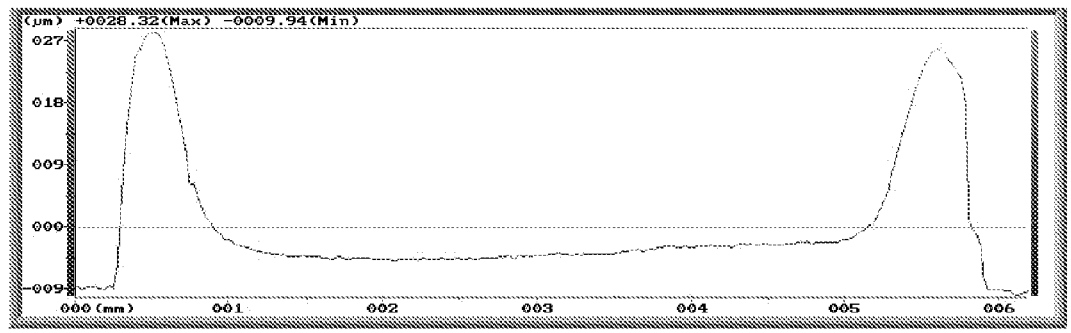
FIG. 4 is a graph of a cross-sectional profile of a reagent film hand-coated of Example 8 on a gold electrode substrate in accordance to the embodiments.

Using the General Fabrication Method described above, 12.0 μl of the reagent solution of Example 1 was dispensed onto the gold electrode. A laser profilometer (SCANTRON PROSCAN 2000®; available from Scantron Industrial Products Ltd, England) was used to obtain cross-sectional profiles (FIG. 4) of dried reagent films on gold electrodes.

Example 9

Figure 5:
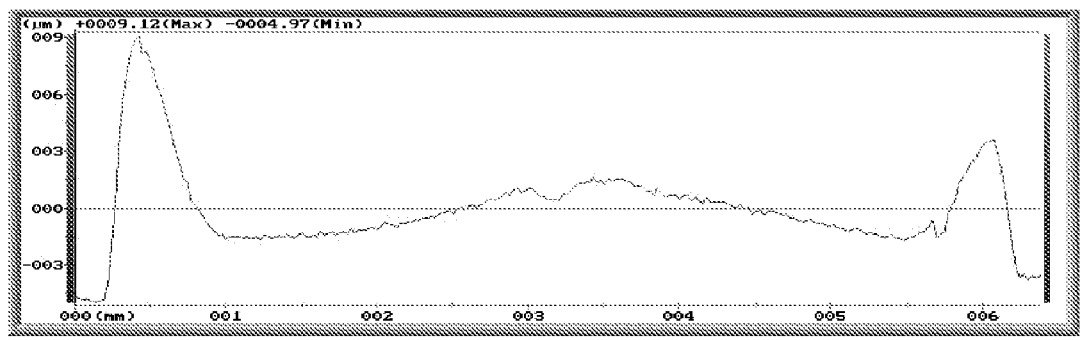
FIG. 5 is a graph of a cross-sectional profile of a reagent film hand-coated of Example 9 on a gold electrode substrate in accordance to the embodiments.

Using the General Fabrication Method described above, 6.0 μl of the reagent solution of Example 1 was dispensed onto the gold electrode. A laser profilometer (SCANTRON PROSCAN 2000®; available from Scantron Industrial Products Ltd, England) was used to obtain cross-sectional profiles (FIG. 5) of dried reagent films on gold electrodes.

Example 10

Figure 6:
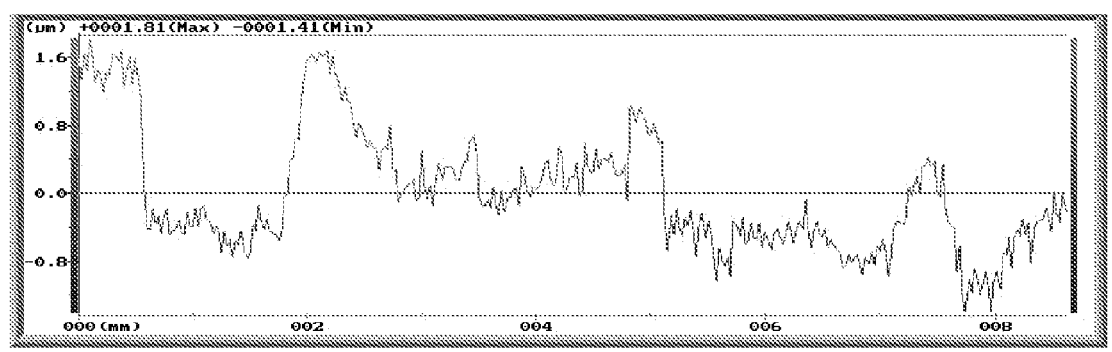
FIG. 6 is a graph of a cross-sectional profile of a reagent film hand-coated of Example 10 on a gold electrode substrate in accordance to the embodiments.

Using the General Fabrication Method described above, 3.0 μl of the reagent solution of Example 1 was dispensed onto the gold electrode. A laser profilometer (SCANTRON PROSCAN 2000®; available from Scantron Industrial Products Ltd, England) was used to obtain cross-sectional profiles (FIG. 6) of dried reagent films on gold electrodes.

Example 11

Figure 7:
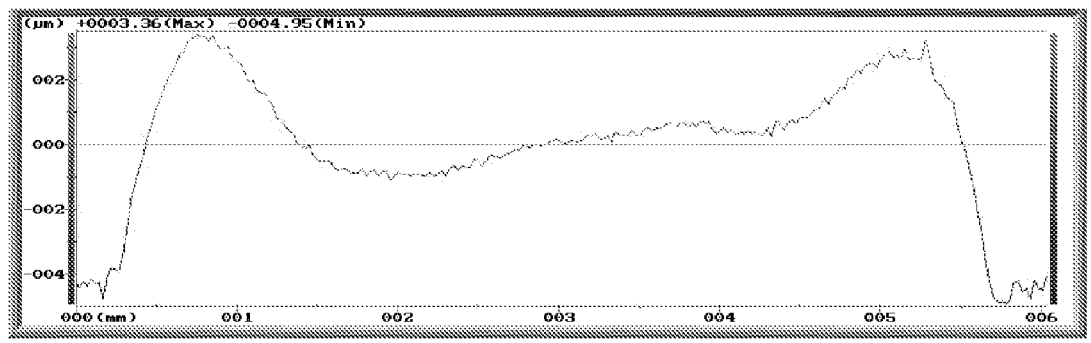
FIG. 7 is a graph of a cross-sectional profile of a reagent film hand-coated of Example 11 on a gold electrode substrate in accordance to the embodiments.

Using the General Fabrication Method described above, 3.0 μl of the reagent solution of Example 2 was dispensed onto the gold electrode. A laser profilometer (SCANTRON PROSCAN 2000®; available from Scantron Industrial Products Ltd, England) was used to obtain cross-sectional profiles (FIG. 7) of dried reagent films on gold electrodes.

Example 12

Figure 8:
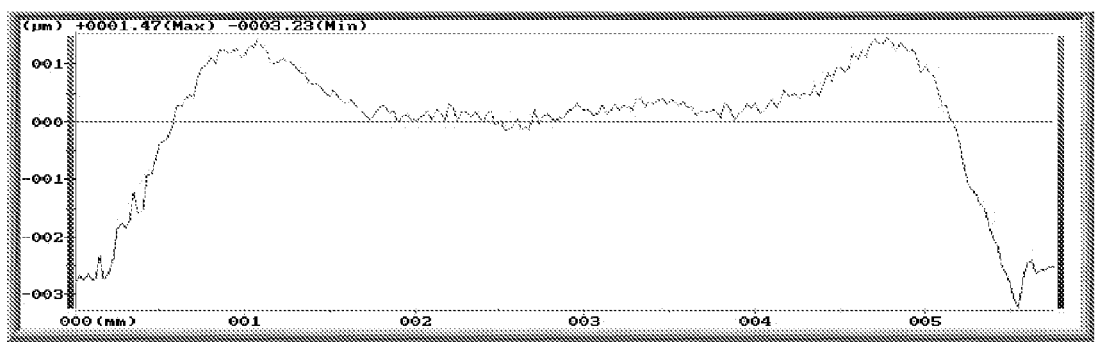
FIG. 8 is a graph of a cross-sectional profile of a reagent film hand-coated of Example 12 on a gold electrode substrate in accordance to the embodiments.

Using the General Fabrication Method described above, 2.5 μl of the reagent solution of Example 2 was dispensed onto the gold electrode. A laser profilometer (SCANTRON PROSCAN 2000®; available from Scantron Industrial Products Ltd, England) was used to obtain cross-sectional profiles (FIG. 8) of dried reagent films on gold electrodes.

Example 13

Figure 9:
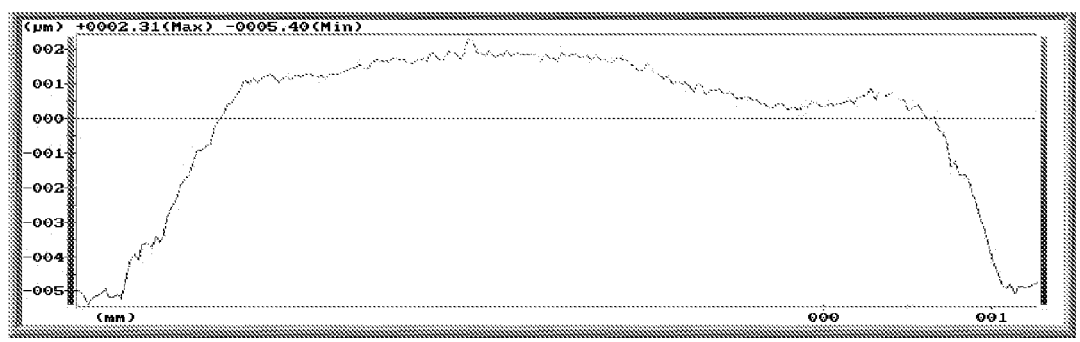
FIG. 9 is a graph of a cross-sectional profile of a reagent film hand-coated of Example 13 on a gold electrode substrate in accordance to the embodiments.

Using the General Fabrication Method described above, 2.0 μl of the reagent solution of Example 2 was dispensed onto the gold electrode. A laser profilometer (SCANTRON PROSCAN 2000®; available from Scantron Industrial Products Ltd, England) was used to obtain cross-sectional profiles (FIG. 9) of dried reagent films on gold electrodes.

Example 14

Figure 10:
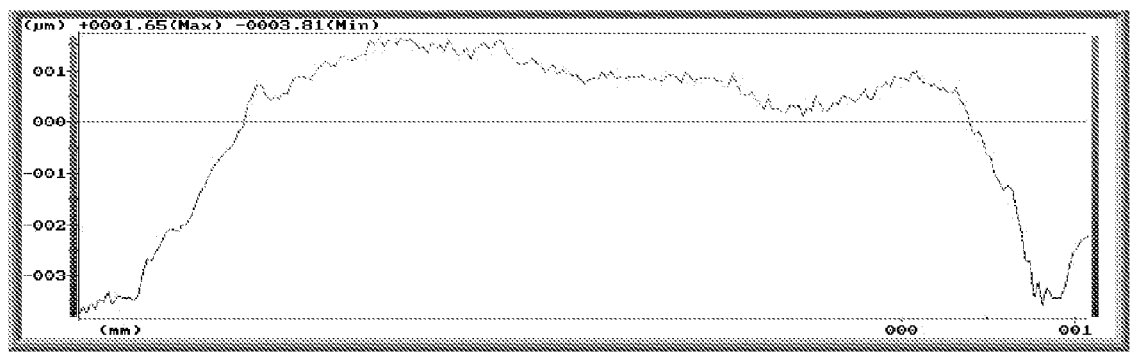
FIG. 10 is a graph of a cross-sectional profile of a reagent film hand-coated of Example 14 on a gold electrode substrate in accordance to the embodiments.

Using the General Fabrication Method described above, 1.5 μl of the reagent solution of Example 2 was dispensed onto the gold electrode. A laser profilometer (SCANTRON PROSCAN 2000®; available from Scantron Industrial Products Ltd, England) was used to obtain cross-sectional profiles (FIG. 10) of dried reagent films on gold electrodes.

Example 15

Figure 11:
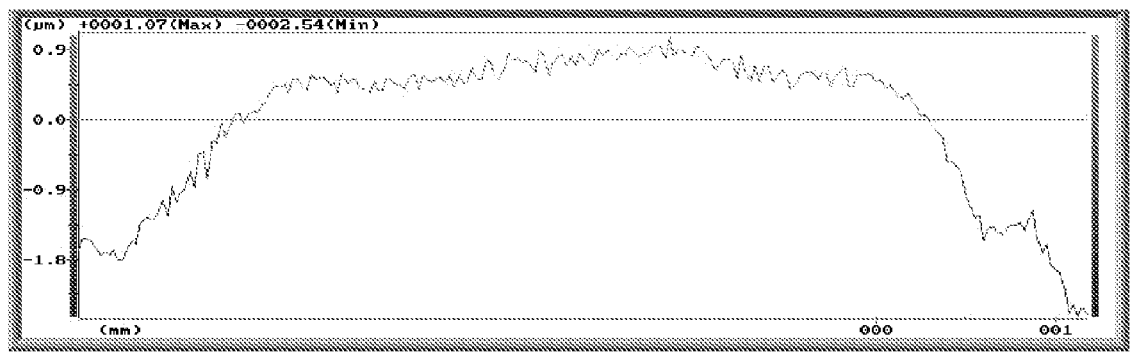
FIG. 11 is a graph of a cross-sectional profile of a reagent film hand-coated of Example 15 on a gold electrode substrate in accordance to the embodiments.

Using the General Fabrication Method described above, 1 μl of the reagent solution of Example 2 was dispensed onto the gold electrode. A laser profilometer (SCANTRON PROSCAN 2000®; available from Scantron Industrial Products Ltd, England) was used to obtain cross-sectional profiles (FIG. 11) of dried reagent films on gold electrodes.

Example 16

Figure 12:
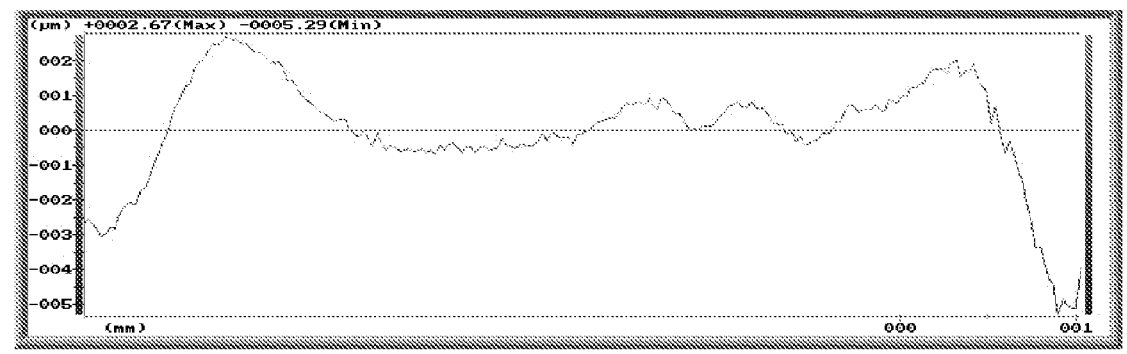
FIG. 12 is a graph of a cross-sectional profile of a reagent film hand-coated of Example 16 on a gold electrode substrate in accordance to the embodiments.

Using the General Fabrication Method described above, 3.0 μl of the reagent solution of Example 3 was dispensed onto the gold electrode. A laser profilometer (SCANTRON PROSCAN 2000®; available from Scantron Industrial Products Ltd, England) was used to obtain cross-sectional profiles (FIG. 12) of dried reagent films on gold electrodes.

Example 17

Figure 13:
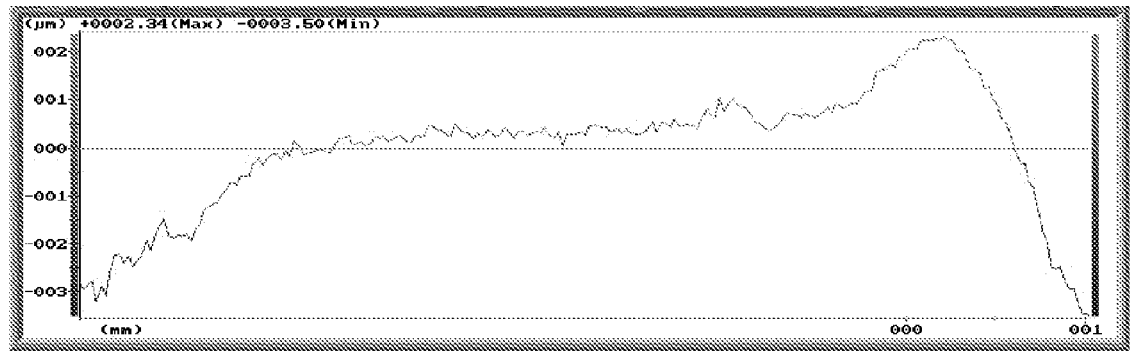
FIG. 13 is a graph of a cross-sectional profile of a reagent film hand-coated of Example 17 on a gold electrode substrate in accordance to the embodiments.

Using the General Fabrication Method described above, 2.5 μl of the reagent solution of Example 3 was dispensed onto the gold electrode. A laser profilometer (SCANTRON PROSCAN 2000®; available from Scantron Industrial Products Ltd, England) was used to obtain cross-sectional profiles (FIG. 13) of dried reagent films on gold electrodes.

Example 18

Figure 14:
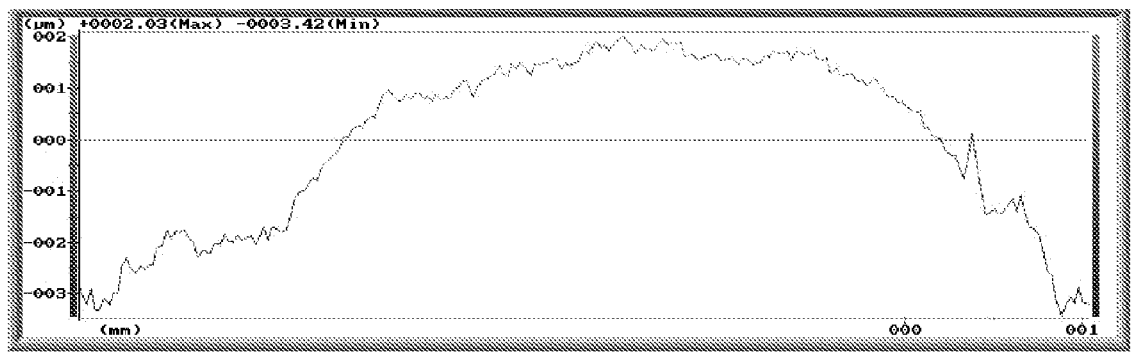
FIG. 14 is a graph of a cross-sectional profile of a reagent film hand-coated of Example 18 on a gold electrode substrate in accordance to the embodiments.

Using the General Fabrication Method described above, 2.0 μl of the reagent solution of Example 3 was dispensed onto the gold electrode. A laser profilometer (SCANTRON PROSCAN 2000®; available from Scantron Industrial Products Ltd, England) was used to obtain cross-sectional profiles (FIG. 14) of dried reagent films on gold electrodes.

Example 19

Figure 15:
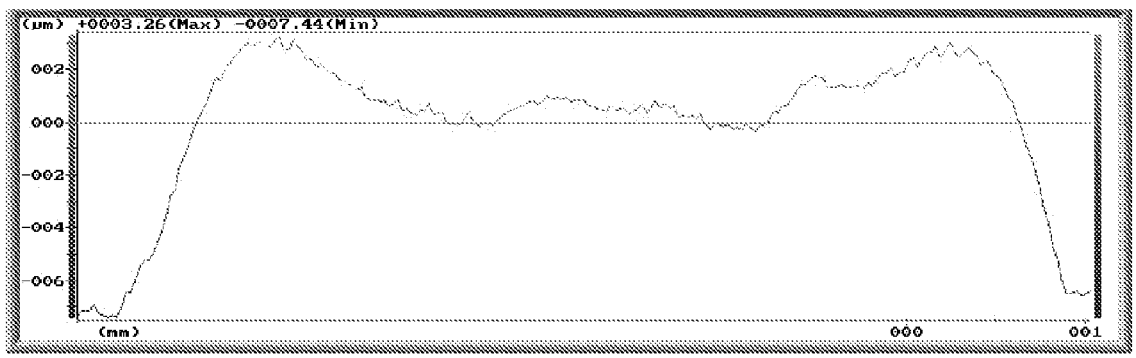
FIG. 15 is a graph of a cross-sectional profile of a reagent film hand-coated of Example 19 on a gold electrode substrate in accordance to the embodiments.

Using the General Fabrication Method described above, 2.5 μl of the reagent solution of Example 4 was dispensed onto the gold electrode. A laser profilometer (SCANTRON PROSCAN 2000®; available from Scantron Industrial Products Ltd, England) was used to obtain cross-sectional profiles (FIG. 15) of dried reagent films on gold electrodes.

Example 20

Figure 16:
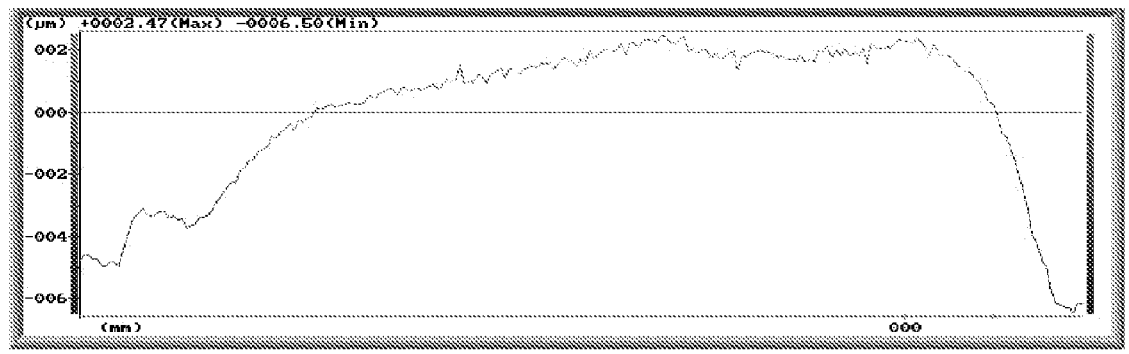
FIG. 16 is a graph of a cross-sectional profile of a reagent film hand-coated of Example 20 on a gold electrode substrate in accordance to the embodiments.

Using the General Fabrication Method described above, 2.0 μl of the reagent solution of Example 4 was dispensed onto the gold electrode. A laser profilometer (SCANTRON PROSCAN 2000®; available from Scantron Industrial Products Ltd, England) was used to obtain cross-sectional profiles (FIG. 16) of dried reagent films on gold electrodes.

Example 21

Figure 17:
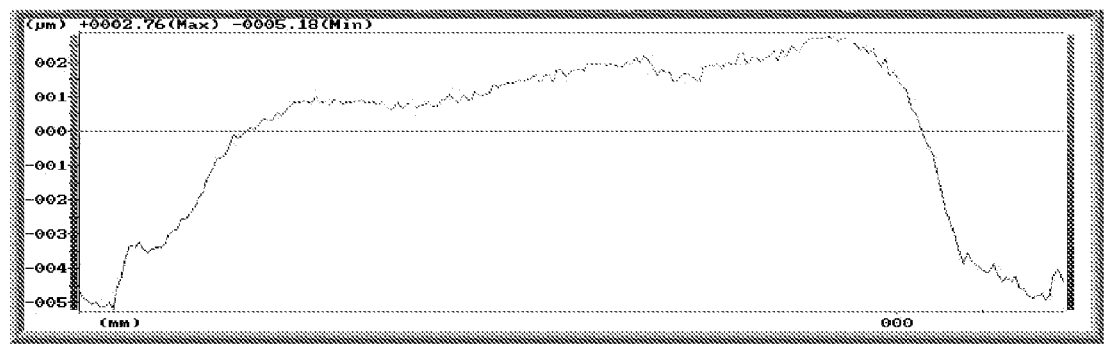
FIG. 17 is a graph of a cross-sectional profile of a reagent film hand-coated of Example 21 on a gold electrode substrate in accordance to the embodiments.

Using the General Fabrication Method described above, 2.0 μl of the reagent solution of Example 5 was dispensed onto the gold electrode. A laser profilometer (SCANTRON PROSCAN 2000®; available from Scantron Industrial Products Ltd, England) was used to obtain cross-sectional profiles (FIG. 17) of dried reagent films on gold electrodes.

Example 22

Figure 18:
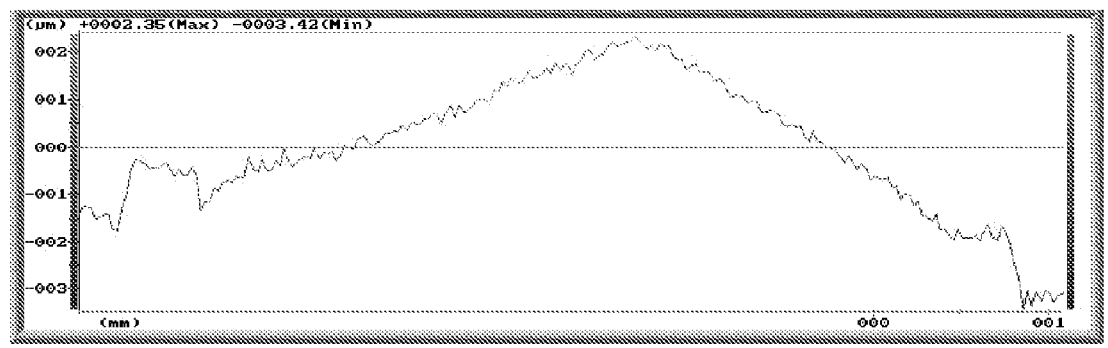
FIG. 18 is a graph of a cross-sectional profile of a reagent film hand-coated of Example 22 on a gold electrode substrate in accordance to the embodiments.

Using the General Fabrication Method described above, 1.5 μl of the reagent solution of Example 5 was dispensed onto the gold electrode. A laser profilometer (SCANTRON PROSCAN 2000®; available from Scantron Industrial Products Ltd, England) was used to obtain cross-sectional profiles (FIG. 18) of dried reagent films on gold electrodes.

Example 23

Figure 19:
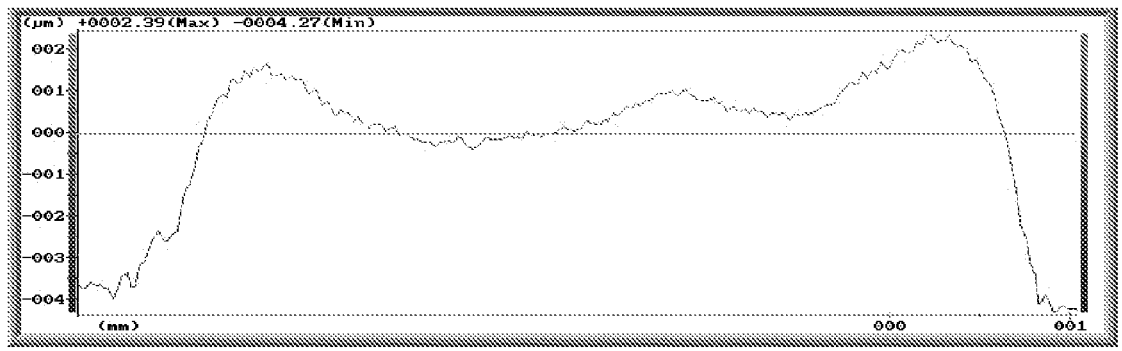
FIG. 19 is a graph of a cross-sectional profile of a reagent film hand-coated of Example 23 on a gold electrode substrate in accordance to the embodiments.

Using the General Fabrication Method described above, 2.0 μl of the reagent solution of Example 6 was dispensed onto the gold electrode. A laser profilometer (SCANTRON PROSCAN 2000®; available from Scantron Industrial Products Ltd, England) was used to obtain cross-sectional profiles (FIG. 19) of dried reagent films on gold electrodes.

Example 24

Figure 20:
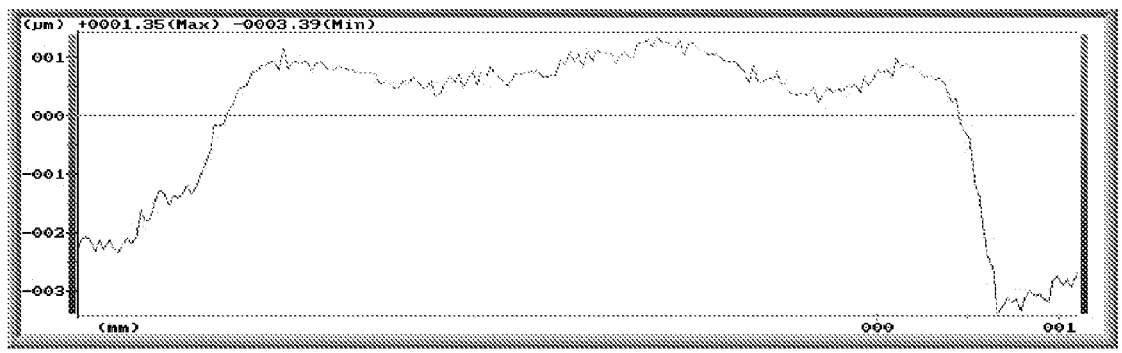
FIG. 20 is a graph of a cross-sectional profile of a reagent film hand-coated of Example 24 on a gold electrode substrate in accordance to the embodiments.

Using the General Fabrication Method described above, 1.8 μl of the reagent solution of Example 6 was dispensed onto the gold electrode. A laser profilometer (SCANTRON PROSCAN 2000®; available from Scantron Industrial Products Ltd, England) was used to obtain cross-sectional profiles (FIG. 20) of dried reagent films on gold electrodes.

Example 25

Figure 21:
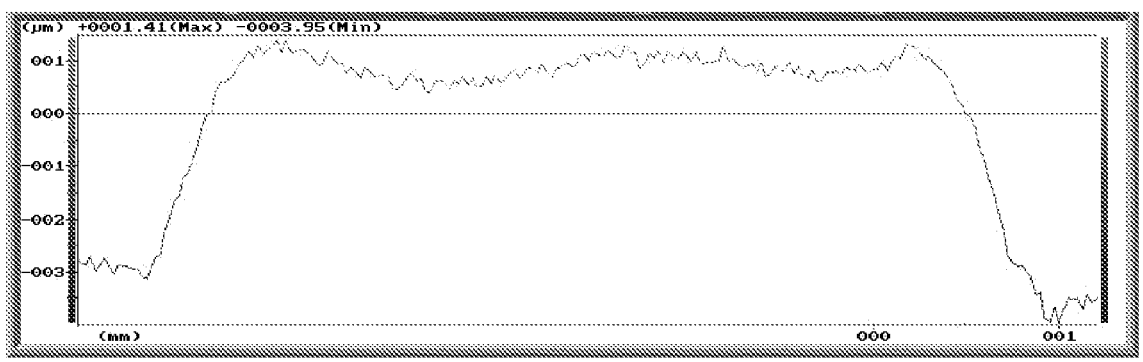
FIG. 21 is a graph of a cross-sectional profile of a reagent film hand-coated of Example 25 on a gold electrode substrate in accordance to the embodiments.

Using the General Fabrication Method described above, 1.8 μl of the reagent solution of Example 7 was dispensed onto the gold electrode. A laser profilometer (SCANTRON PROSCAN 2000®; available from Scantron Industrial Products Ltd, England) was used to obtain cross-sectional profiles (FIG. 21) of dried reagent films on gold electrodes.

Figure 22:
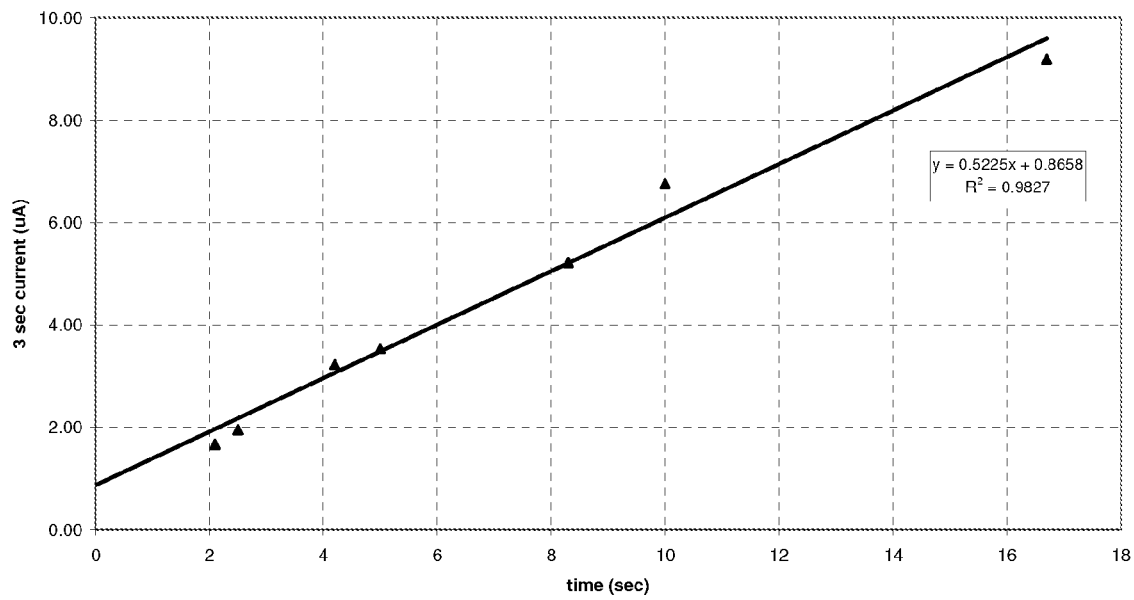
FIG. 22 is a graph of 3 sec current v. time for test results of Example 25.

The coated electrodes of Example 25 were tested with the glucose in phosphate-buffered saline (PBS). Tests were conducted with parameters of 0 sec delay, +200 mV applied potential (vs. mediator redox couple—biamperometry), 3 sec assay, 100 Hz sampling time and manual assay start. Results are presented in a graph of 3 sec current v. time (FIG. 22).

An aging study was conducted on two formulations, Example 26 and 27, as described in Table 3. Example 26 was prepared and a short section (about 5.5 cm) of web comprising ten (10) electrodes was coated using the General Fabrication Method of hand-coated gold electrodes as described above. Example 27 was prepared and a web was coated using the slot die method as described for Examples 41-46. After coating, about 80 meters of Examples 27 were wound up and stored for several months at ambient conditions (ranging from about 15-25° C. and 30-70% relative humidity). Upon visual examination, the coated webs made from Example 26 and 27 both exhibited reagent films that adhered well to the patterned gold-PET substrate with no occurrences of flaking or peeling. Additionally, no cracking of the film coatings was visually observed. Furthermore, upon unwinding the reel of Example 27, no evidence of the reagent film sticking to the underside of the web in a wound reel was observed. The visual observations of the aging study confirm the flexibility and non-tackiness of the coated films.

TABLE 3

Formulations for aging studies of Examples 26 and 27 and rheology studies of Examples 30 and 31 (% w/v).

| Material | Example 26 (% w/v) | Example 27 (% w/v) | Example 30 (% w/v) | Example 31 (% w/v) |
|---|---|---|---|---|
| [Ni(PQ)$_3$]Cl$_2$ | 3.4 | 6.4 | 6.4 | 6.4 |
| KOLLICOAT PROTECT ® | 2.0 | 3.0 | 3.0 | N/A |
| KOLLICOAT SR30D ® (30% solids) | *N/A | N/A | N/A | 16.7 |
| MgCl$_2$ | 0.7 | N/A | N/A | N/A |
| LiCl | N/A | 1.2 | 1.2 | 1.2 |
| trehalose | 5.0 | 7.5 | 7.5 | 7.5 |
| NAD, sodium salt | 0.5 | 1.4 | 1.4 | 1.4 |
| NAD-GDH | 2.0 | 3.7 | 3.7 | 3.7 |
| **FMN | N/A | 1.0 | N/A | N/A |
| Total % solids | 13.6 | 24.2 | 23.2 | 25.2 |

*N/A indicates no additive
**FMN is flavin mononucleotide

Examples 30 and 31

Rheology of Solutions

Figure 23:
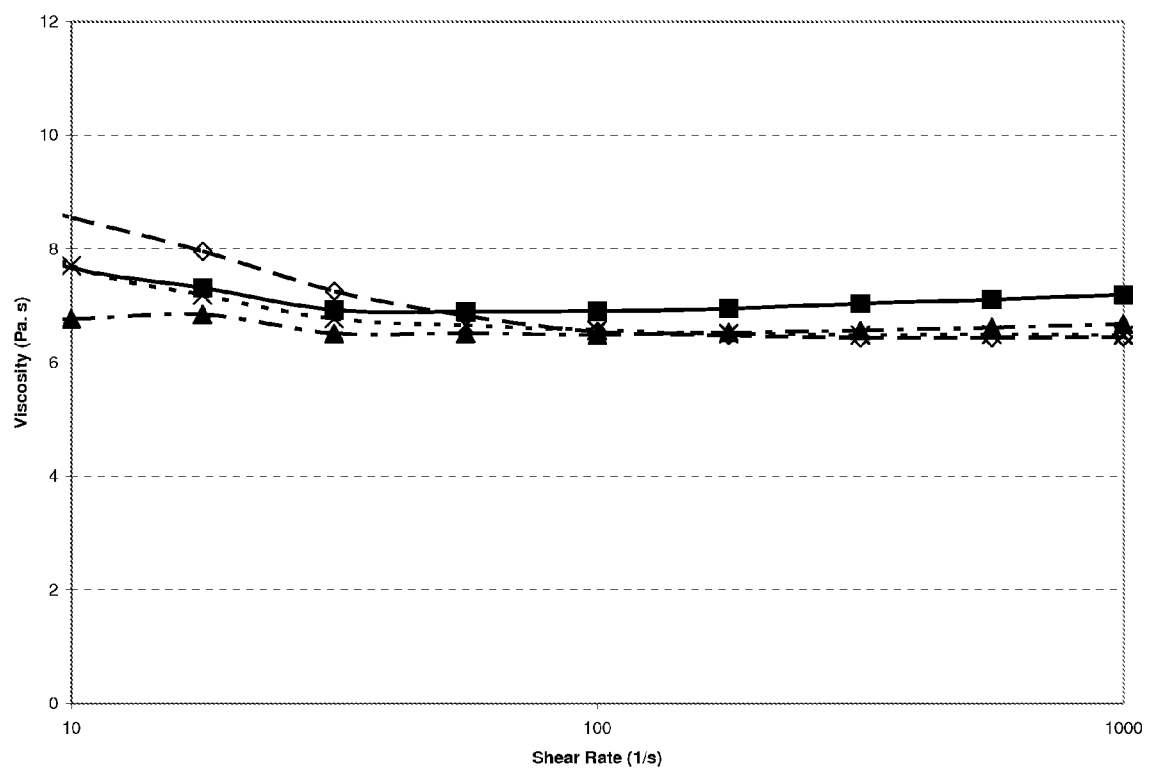
FIG. 23 is a graph of viscosity v. shear rate for test results of Example 30.

The rheologies of slot coating formulations of Example 30 and Example 31 (Table 3 above) were studied using a cone and plate rheometer (available from TA Instruments, New Castle, Del.). The rheological behavior of both solutions was found to be essentially Newtonian, i.e., the viscosity was independent of shear rate, in the range 10-1000 s$^{-1}$. FIG. 23 is a graph of viscosity (s) v shear rate (s$^{-1}$) of four measurements on the same solution of Example 30. The graph shows that Example 30 was essentially Newtonian. The Newtonian aspect of the solution can be important when it is desired to maintain coating consistency over a wide range of web speeds.

The viscosity of Example 30 and Example 31 was found to be 6.6 and 3.3 mPa s respectively at 25° C.

Viscosity measurements were made on Examples 32-40 described in Table 4. The viscosity values are reported in Table 5.

TABLE 4

Formulations for Examples 32-40.

| Material | Ex 32 | Ex 33 | Ex 34 | Ex 35 | Ex 36 | Ex 37 | Ex 38 | Ex 39 | Ex 40 |
|---|---|---|---|---|---|---|---|---|---|
| Water | 63.45 | 72.95 | 68.15 | 69.65 | 62.1 | 72.1 | 64.2 | 59.5 | 75.4 |
| Trehalose | 7.5 | 7.5 | 7.5 | 7.5 | 7.5 | 7.5 | 7.5 | 7.5 | 7.5 |
| LiCl | 0.75 | 0.75 | 0.75 | 0.75 | 1.2 | 1.5 | 1.5 | 1.5 | 1.5 |
| NaNAD | 1.4 | 1.4 | 0.7 | 0.7 | 1.4 | 0.7 | 0.7 | 1.4 | 1.4 |
| [Ni(PQ)$_3$]Cl$_2$ | 3.2 | 6.4 | 3.2 | 6.4 | 6.4 | 3.2 | 6.4 | 6.4 | 3.2 |
| GDH | 6.0 | 2.0 | 2.0 | 6.0 | 3.7 | 6.0 | 2.0 | 6.0 | 2.0 |
| KOLLICOAT SR30D ® (30% solids) | 16.7 | 8.0 | 16.7 | 8.0 | 16.7 | 8.0 | 16.7 | 16.7 | 8.0 |
| *FMN | 1.0 | 1.0 | 1.0 | 1.0 | 1.0 | 1.0 | 1.0 | 1.0 | 1.0 |
| Total % solids | 24.85 | 21.45 | 20.15 | 24.75 | 26.2 | 22.3 | 24.1 | 28.8 | 19.0 |

*FMN is flavin mononucleotide

TABLE 5

Viscosities of Examples 32-40 in mPa s.

| Example | Viscosity (mPa·s) |
|---|---|
| 32 | 2.89 |
| 33 | 2.01 |
| 34 | 2.38 |
| 35 | 2.47 |
| 36 | 2.92 |
| 37 | 2.13 |
| 38 | 2.46 |
| 39 | 3.41 |
| 40 | 1.85 |

Figure 24:
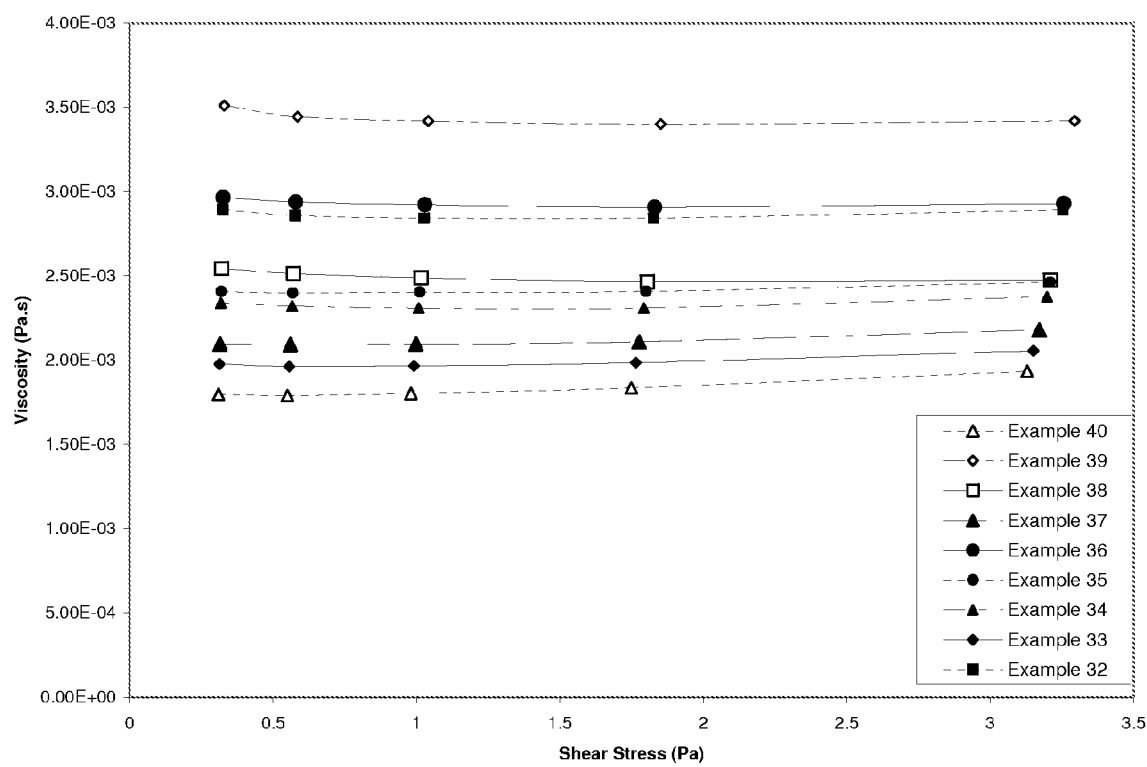
FIG. 24 is a graph of viscosity v. shear stress for Examples 32-40.
Figure 25:
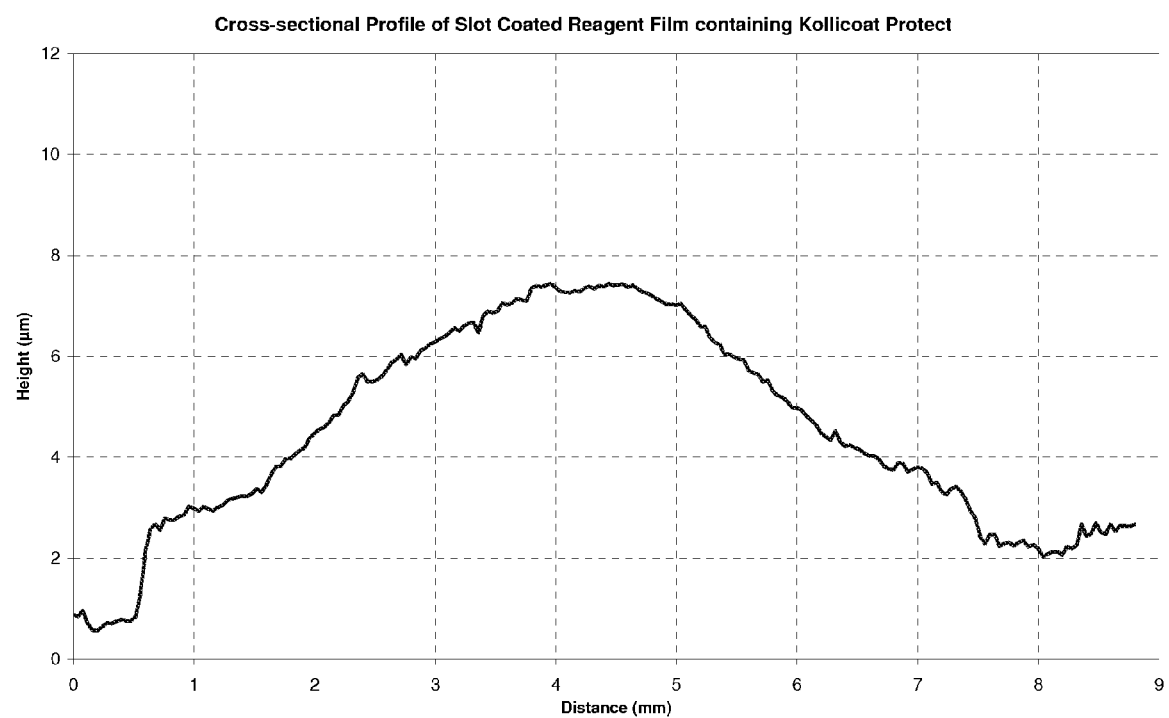
FIG. 25 is a graph of a cross-sectional profile of a reagent film coated with a slot die of Example 41 in accordance to the embodiments.
Figure 26:
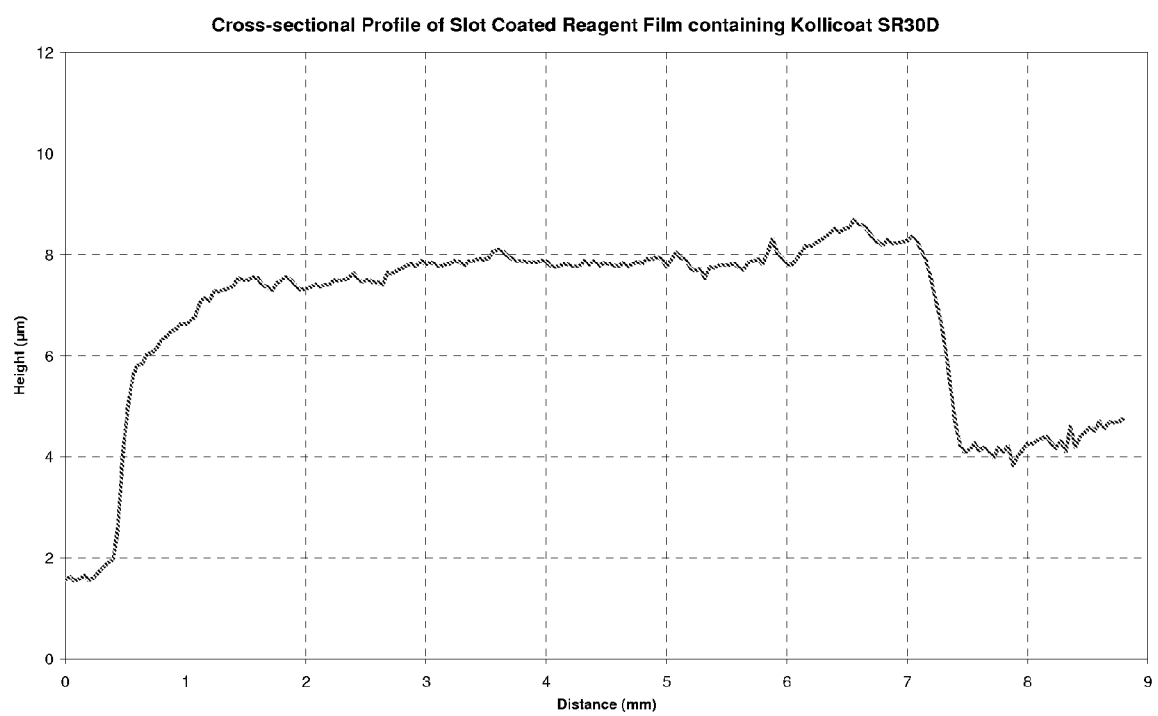
FIG. 26 is a graph of a cross-sectional profile of a reagent film coated with a slot die of Example 42 in accordance to the embodiments.
Figure 27:
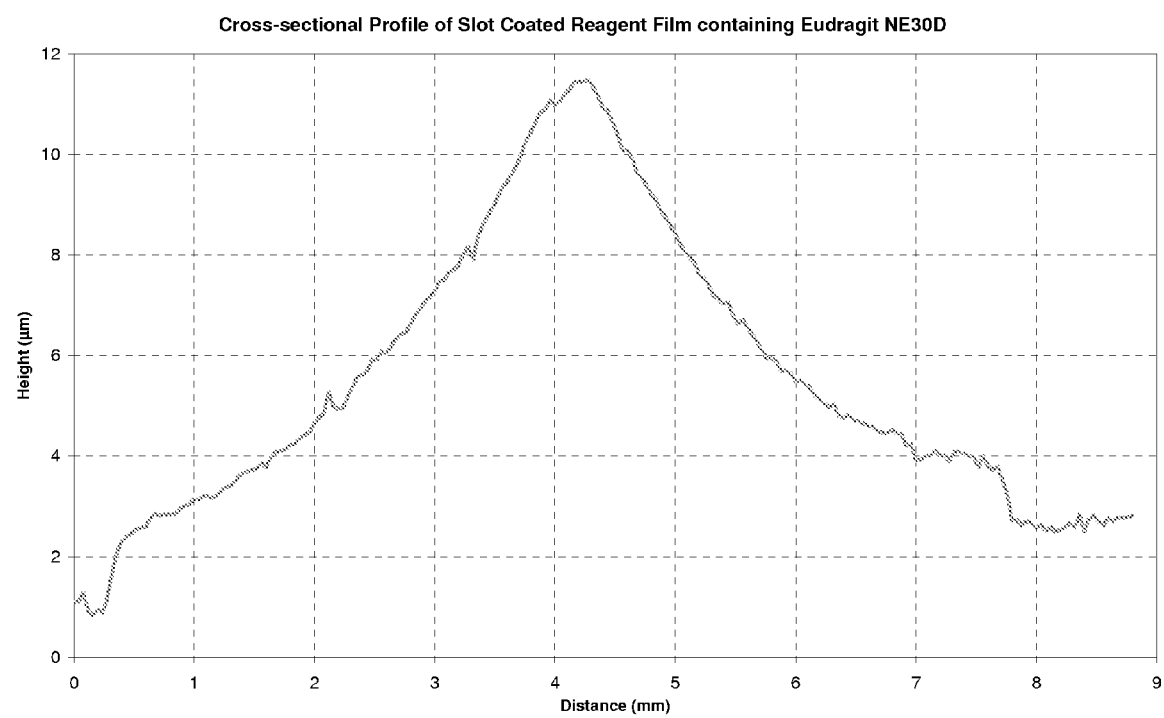
FIG. 27 is a graph of a cross-sectional profile of a reagent film coated with a slot die of Example 43 in accordance to the embodiments.
Figure 28:
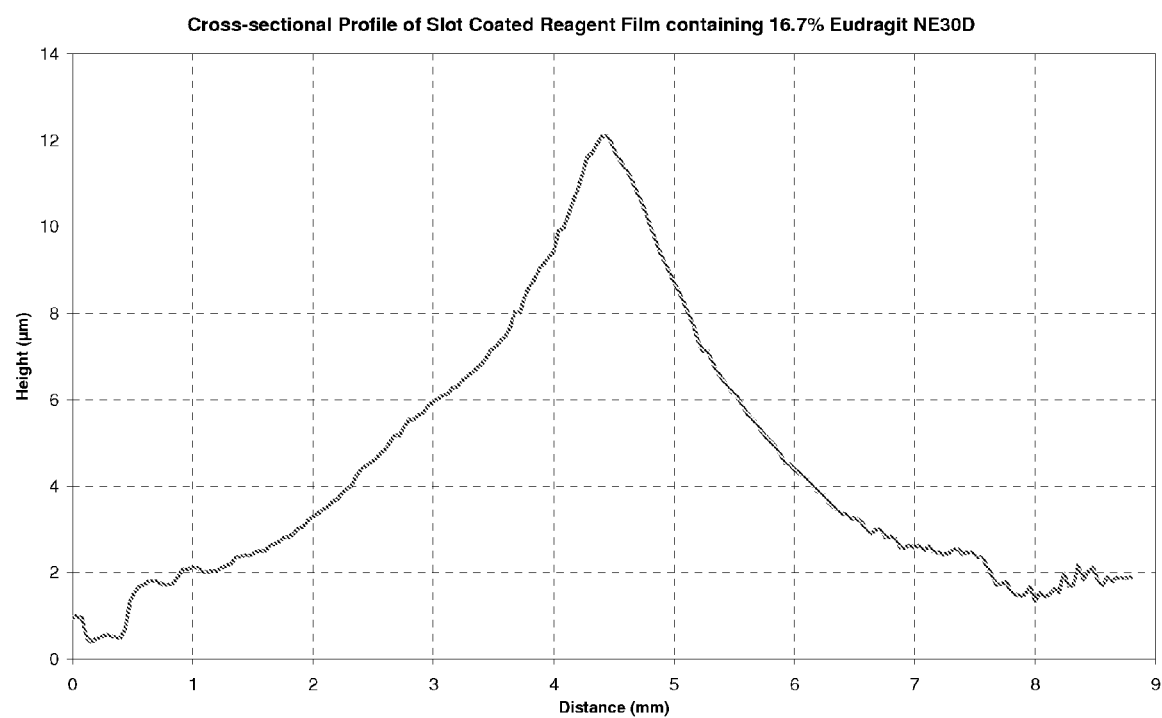
FIG. 28 is a graph of a cross-sectional profile of a reagent film coated with a slot die of Example 44 in accordance to the embodiments.
Figure 29:
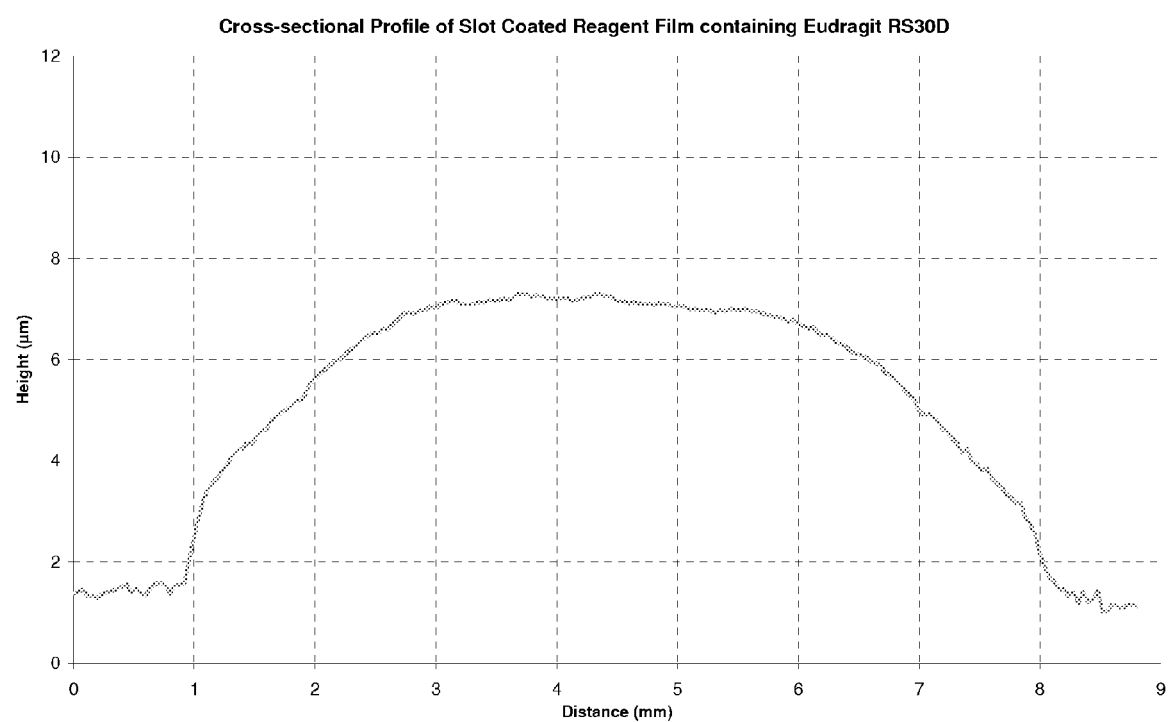
FIG. 29 is a graph of a cross-sectional profile of a reagent film coated with a slot die of Example 45 in accordance to the embodiments.
Figure 30:
FIG. 30 is a graph of a cross-sectional profile of a reagent film coated with a slot die of Example 46 in accordance to the embodiments.

FIG. 24 is a graph of viscosity (Pa·s) v shear stress (Pa) for Examples 32-40. All Examples exhibit essentially Newtonian behavior.

The reagent solutions (Example 41-46; Table 6) were deposited as a continuous stripe on moving gold patterned PET substrate in the form of a 40 mm wide web. Delivery of solutions was controlled by a syringe pump at 0.6 mL/min at a web speed of about 4 m/min. The slot die slot-to-web gap was 30 μm with a slot height of 105 μm, slot width of 6 mm and a drying temperature of 75° C. over a 2 m length drying oven.

The resulting wet coat weight for the reagent solution was calculated according to the following equation:

Wet coat weight (g/m$^2$)=reagent flow rate/[web speed×(slot width/1000)].

Applying this equation resulted in a wet coat weight of reagent solution of 25 g/m$^2$. Dry, non-tacky reagent films were obtained for Examples 32-40 under these slot die coating conditions.

TABLE 6

Formulations for Examples 41-46 (wt %).

| Material | Ex 41 | Ex 42 | Ex 43 | Ex 44 | Ex 45 | Ex 46 |
|---|---|---|---|---|---|---|
| Water | 79.6 | 63.4 | 63.4 | 63.4 | 63.4 | 73.9 |
| Trehalose | 7.5 | 7.5 | 7.5 | 7.5 | 7.5 | 7.4 |
| LiCl | 1.2 | 1.2 | 1.2 | 1.2 | 1.2 | 1.2 |
| NAD | 1.4 | 1.3 | 1.3 | 1.3 | 1.3 | 1.2 |
| [Ni(PQ)$_3$]Cl$_2$ | 6.4 | 6.4 | 6.4 | 6.4 | 6.4 | 6.4 |
| NAD-GDH | 3.7 | 3.7 | 3.7 | 3.7 | 3.7 | 3.7 |
| KOLLICOAT PROTECT ® | 0.2 | *N/A | N/A | N/A | N/A | N/A |

TABLE 6-continued

Formulations for Examples 41-46 (wt %).

| Material | Ex 41 | Ex 42 | Ex 43 | Ex 44 | Ex 45 | Ex 46 |
|---|---|---|---|---|---|---|
| KOLLICOAT SR30D ® (30% solids) | N/A | 16.7 | N/A | N/A | N/A | N/A |
| EUDRAGIT NE30D ® (30% solids) | N/A | N/A | 16.7 | N/A | N/A | N/A |
| EUDRAGIT RL30D ® (30% solids) | N/A | N/A | N/A | 16.7 | N/A | N/A |
| EUDRAGIT RS30D ® (30% solids) | N/A | N/A | N/A | N/A | 16.7 | N/A |
| EUDRAGIT NE30D ® (30% solids) | N/A | N/A | N/A | N/A | N/A | 6.7 |
| Total % solids | 20.4 | 25.1 | 25.1 | 25.1 | 25.1 | 25.1 |

*N/A indicates no additive

Laser profilometry (using a Mitutoyo Quick Vision PRO, available from Mitutoyo America Corporation, Aurora, Ill.) was performed on slot-die coated Examples 41-46. FIGS. 25-30 show the laser profilometry results for Examples 41-46 respectively.

Mixed Fast Release/Sustained Release Polymers

TABLE 7

Materials and concentrations (w/v %) of the aqueous preparation of Example 47.

| Material | Concentration (% w/v) |
|---|---|
| [Ni(PQ)$_3$]Cl$_2$ | 3.4 |
| KOLLICOAT PROTECT ® | 0.05 |
| MgCl$_2$ | 0.7 |
| Trehalose | 5.0 |
| Erioglaucine (blue dye) | 0.2 |
| Total % solids | 9.35 |

Example 48

Example 48 was prepared using a 5:1 volume ratio of Example 47: EUDRAGIT RL30D®.

Example 49

Example 49 was prepared using a 5:1 volume ratio of Example 47: EUDRAGIT NE30D®.

Example 50

Example 50 was prepared using a 5:1 volume ratio of Example 47: KOLLICOAT SR30D®.

Example 51

Example 51 was prepared using a 5:1 volume ratio of Example 47: KOLLICOAT MAE30DP®.

Examples 47-51 were coated onto separate biosensors by depositing solutions into embossed channels using the squeegee method disclosed in U.S. Pat. No. 7,312,042 (Petyt et al.), which is incorporated by reference in its entirety. The resulting embossed electrodes were tested using a +200 mV operating potential, 1 sec poise delay, and 2 sec assay delay with NADH/PBS solutions (2.6, 5.2 and 10.4 mM). Table 8 lists the results of the electrode testing.

TABLE 8

Test results for Examples 47-51.

| Material | NADH response slope at 2 sec (µA/mM) | NADH response intercept at 2 sec (µA) | Correlation coefficient R$^2$ |
|---|---|---|---|
| Example 47 | 0.22 | 1.01 | 0.710 |
| Example 48 | 0.06 | 1.42 | 0.664 |
| Example 49 | 0.25 | 0.60 | 0.886 |
| Example 50 | 0.34 | 0.43 | 0.933 |
| Example 51 | 0.08 | 1.57 | 0.629 |

Example 49 and Example 50 gave values of NADH response slopes at 2 sec which were higher than that of Example 47; this was an indicator of a reduced amount of reagent "wash-through." Low intercepts and improved linearity were also seen for Examples 49 and 50 compared to Example 47, which contained only fast release polymer. A minor amount of visible "wash-through" of the blue dye to the rear of the embossed cell was apparent.

Examples 52-61 were prepared using materials and concentrations (w/v %) listed in Tables 9 and 10 below and coated as described for Examples 47-51 above. The resulting embossed electrodes were tested using a +200 mV operating potential, no poise delay, and 1 sec assay delay with glucose/PBS solutions (5, 10 and 20 mM). Table 11 lists the results of the electrode testing for Examples 52-61.

TABLE 9

Formulations containing [Ni(PQ)$_3$]Cl$_2$; Examples 52-56 (% w/v).

| Material | Ex 52 | Ex 53 | Ex 54 | Ex 55 | Ex 56 |
|---|---|---|---|---|---|
| [Ni(PQ)$_3$]Cl$_2$ | 3.4 | 3.4 | 3.4 | 3.4 | 3.4 |
| KOLLICOAT PROTECT ® | 0.05 | 0.05 | 0.05 | 0.05 | 0.05 |
| LiCl | 0.7 | 0.7 | 0.7 | 0.7 | 0.7 |
| Trehalose | 5.0 | 5.0 | 5.0 | 5.0 | 5.0 |
| NAD-GDH | 1.0 | 1.0 | 1.0 | 1.0 | 1.0 |
| NAD | 0.5 | 0.5 | 0.5 | 0.5 | 0.5 |
| KOLLICOAT SR30D ® (30% solids) | *N/A | 16.7 | N/A | 33.3 | N/A |
| EUDRAGIT NE30D ® (30% solids) | N/A | N/A | 16.7 | N/A | 33.3 |
| Total % solids | 10.65 | 15.65 | 15.65 | 20.65 | 20.65 |

*N/A indicates no additive

TABLE 10

Formulations containing Ni(PQ)$_3$Br$_2$; Examples 57-62 (% w/v).

| Material | Ex 57 | Ex 58 | Ex 59 | Ex 60 | Ex 61 | Ex 62 |
|---|---|---|---|---|---|---|
| [Ni(PQ)$_3$]Br$_2$ | 2.0 | 2.0 | 2.0 | 2.0 | 2.0 | 6.4 |
| KOLLICOAT PROTECT ® | 0.05 | 0.05 | 0.05 | 0.05 | 0.05 | N/A |
| LiCl | 0.7 | 0.7 | 0.7 | 0.7 | 0.7 | 1.2 |
| Trehalose | 5.0 | 5.0 | 5.0 | 5.0 | 5.0 | 7.5 |
| NAD-GDH | 1.0 | 1.0 | 1.0 | 1.0 | 1.0 | 3.7 |
| NAD | 0.5 | 0.5 | 0.5 | 0.5 | 0.5 | 1.4 |
| KOLLICOAT SR30D ® (30% solids) | *N/A | 16.7 | N/A | 33.3 | N/A | 33.3 |

TABLE 10-continued

Formulations containing Ni(PQ)₃Br₂; Examples 57-62 (% w/v).

| Material | Ex 57 | Ex 58 | Ex 59 | Ex 60 | Ex 61 | Ex 62 |
|---|---|---|---|---|---|---|
| EUDRAGIT NE30D ® (30% solids) | N/A | N/A | 16.7 | N/A | 33.3 | N/A |
| Total % solids | 9.25 | 14.25 | 14.25 | 19.25 | 19.25 | 30.2 |

*N/A indicates no additive

TABLE 11

Test results for Examples 52-61.

| Example | Glucose response slope at 1 sec (μA/mM) | Correlation coefficient $R^2$ |
|---|---|---|
| 52 | 0.22 | 0.724 |
| 53 | 0.41 | 0.950 |
| 54 | 0.39 | 0.817 |
| 55 | 0.31 | 0.805 |
| 56 | 0.26 | 0.80 |
| 57 | 0.22 | −0.657 |
| 58 | 0.33 | 0.496 |
| 59 | 0.35 | 0.948 |
| 60 | 0.29 | 0.735 |
| 61 | 0.22 | 0.670 |

Example 62

Figure 31:
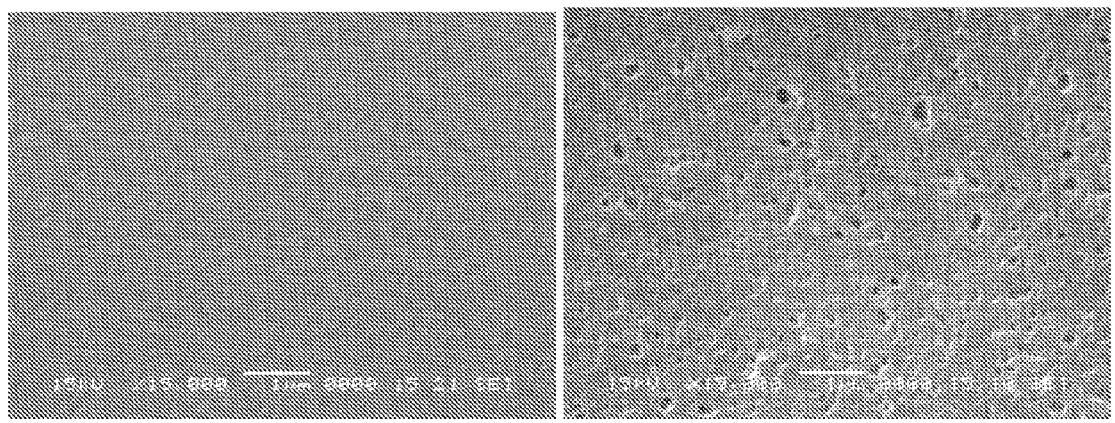
FIG. 31 is Scanning Electron Micrographs (SEMs) of a coated and a washed reagent film composition in accordance to the embodiments.

Example 62 was prepared using a slot die coating method described above and the formulation listed in Table 10. After drying the coated sample, an SEM of the coated sample was taken (FIG. 31; left side). The surface of the coated sample was found to be substantially featureless at the resolution provided. After briefly immersing the coated sample in water for a few seconds and then gently drying with a tissue, another SEM of the washed sample was taken (FIG. 31; right side). The sample immersed in water revealed sub-micron pores. These pores are of sufficiently small size to exclude red blood cells.

Examples of Syntheses of Transition Metal Complexes

Examples showing the syntheses of various transition metal complexes that are useful as redox mediators are provided below. Unless indicated otherwise, all of the chemical reagents are available from Aldrich Chemical Co. (Milwaukee, Wis.) or other sources. Numerical figures provided are approximate.

Example 63

Synthesis of $[Os(Py-MIM)_2(X)Cl]^{2+}2Cl^-$ Complexes

By way of illustration, examples of the syntheses of $[Os(Py-MIM)_2(MAP)Cl]^{2+}2Cl^-$ ("MAP") and $[Os(Py-MIM)_2(MIM)Cl]^{2+}2Cl^-$ ("MIM") as illustrated below, are now provided. As described herein, $[Os(Py-MIM)_2(MAP)Cl]^{2+}2Cl^-$ is a transition metal complex that is particularly useful as a redox mediator.

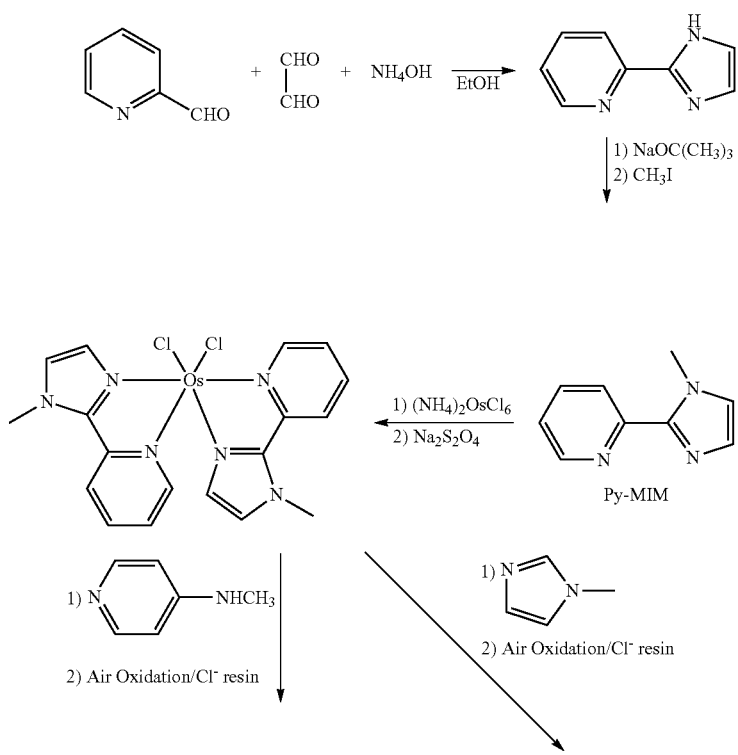

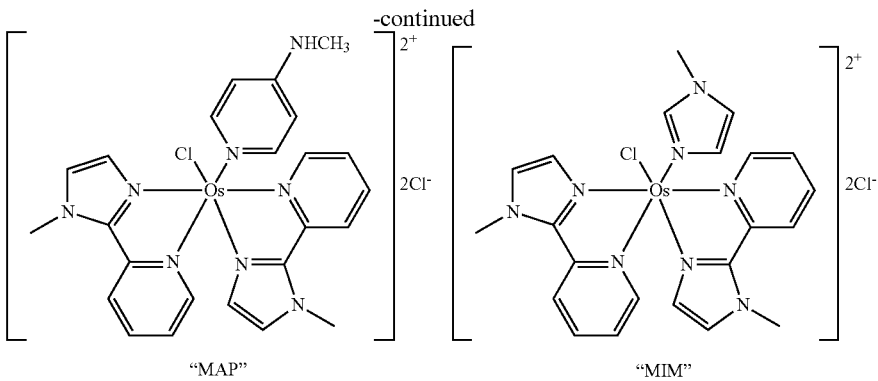

"MAP"          "MIM"

Synthesis of 2-(1H-imidazol-2-yl)pyridine (=pyridyl-imidazole)

A solution of pyridine-2-carboxaldehyde (151.4 g, 1.41 mol) and glyoxal (40% in $H_2O$, 205 mL, 1.79 mol) in 300 mL of ethanol (EtOH) in a three-neck 1 L round-bottom flask fitted with a thermometer and an addition funnel was stirred in an ice bath. When the solution was cooled to below 5° C., concentrated $NH_4OH$ (28-30%, 482 mL, 3.93 mol) was added dropwise through the addition funnel. The rate of the addition was controlled so that the temperature of the solution was maintained at below 5° C. After the addition, the stirring of the solution was continued in the ice bath for one hour and then at room temperature overnight. During the stirring process, the solution changed from light yellow to dark brown.

The solution was transferred to a 2 L round bottom flask and the EtOH solvent was removed by rotary evaporation. The resulting dark viscous material was transferred to a 4 L beaker with 700 mL of EtOAc. Saturated NaCl (500 mL) was added and the mixture was stirred for 2 hours. The solution was poured into a 2 L separation funnel and a dark tarry material was discarded. The organic layer was separated from the solution and the aqueous layer was extracted several times with EtOAc (500 mL EtOAc per extraction). The organic layer was then dried with anhydrous $Na_2SO_4$ overnight, whereupon the resulting mixture was gravity filtered, the $Na_2SO_4$ was washed with EtOAc (4×50 mL), and the solution was concentrated to about 300-400 mL by rotary evaporation. The concentrated solution was transferred to a 1 L Erlenmeyer flask and the volume was adjusted with more EtOAc to about 400-500 mL, as necessary. The solution stood at 4° C. for 1-2 days to form large amber crystals. The crystals were collected by suction filtration and washed with cold EtOAc (20-30 mL). The filtrate contained a large amount of product, so further concentration and crystallization procedures were performed. The crystals were combined and dried at 40-45° C. under high vacuum for 2 days. The yield of 2-(1H-imidazol-2-yl)pyridine was about 75 g (33%).

Synthesis of 2-(1-methyl-1H-imidazol-2-yl)pyridine (=Py-MIM)

Pyridine-2-carboxaldehyde (50.5 g, 0.47 mol) and glyoxal (40% in $H_2O$, 68.3 mL, 0.60 mol) in 100-150 mL of ethanol (EtOH) in a three-neck 1 L round-bottom flask fitted with a thermometer and an addition funnel were stirred in an ice bath. When the solution was cooled to below 5° C., concentrated $NH_4OH$ (28-30%, 161 mL, 1.31 mol) was added dropwise through the addition funnel. The rate of the addition was controlled so that the temperature of the solution was maintained at below 5° C. After the addition, the stirring of the solution was continued in the ice bath for one hour and then at room temperature overnight. During the stirring process, the solution changed from light yellow to dark brown.

The solution was transferred to a 1 L round bottom flask and the EtOH and $H_2O$ solvents were removed by rotary evaporation at 50° C. The resulting material was dried further at about 50° C. under high vacuum for 24 hours and then dissolved in anhydrous dimethylformamide (DMF), whereupon the solution was transferred with further DMF (total DMF 450-500 mL) to a three-neck 1 L round bottom flask equipped with a reflux condenser, and then stirred. Sodium t-butoxide (48.9 g, 0.51 mol) was added quickly via funnel to obtain, with continued stirring for about 1 hour, a dark brown homogeneous solution. Methyl iodide (34.5 mL, 0.56 mol) was then added dropwise via addition funnel over 1.5-2 hours, resulting in a white precipitate of NaI. The mixture was stirred at room temperature overnight, its color changing from dark brown to light brown. The mixture was then poured into a beaker containing 1.5 mL of EtOAc and suction-filtered using a Buchner funnel to remove the NaI precipitate. The precipitate was washed with additional EtOAc (3×100 mL). The filtrate was transferred to a 2 L round bottom flask and concentrated by rotary evaporation to remove the EtOAc.

The resulting viscous material was transferred to a 1 L beaker with a minimum amount of EtOAc, which was then removed by rotary evaporation. The remaining DMF was removed by vacuum distillation using a low vacuum diaphragm pump and an oil bath. Upon complete removal of the DMF, the product was distilled at 100-110° C. under high vacuum. The yield of 2-(1-methyl-1H-imidazol-2-yl)pyridine was about 36 g (48%).

Synthesis of Os(Py-MIM)$_2$Cl$_2$ 2-(1-methyl-1H-imidazol-2-yl)pyridine (3.4 g, 21.4 mmol) and ammonium hexachloroosmiate (IV) (4.7 g, 10.7 mmol) were combined with anhydrous ethylene glycol (86 mL) in a three-neck 250 mL round-bottom flask, fitted with a reflux condenser, immersed in a temperature-controlled oil bath. The reaction mixture was degassed with $N_2$ for about 15 minutes. The mixture was stirred under $N_2$ while the heater was turned on to heat the oil bath, and the reaction proceeded at 130° C. for 2 hours and subsequently at 140° C. for about 28 hours until an intermediate that was formed in the reaction was completely converted to the final product. The solution was cooled to room temperature and then suction-filtered through a fritted funnel into a three-neck 250 mL round bottom flask, whereupon a small amount of orange precipitate left in the funnel was discarded. The solution (solution A) was then degassed with $N_2$ for 15 minutes and kept under $N_2$.

Deionized H$_2$O (320 mL) was then degassed with N$_2$ in a three-neck 500 mL round bottom flask cooled in an ice/water bath and equipped with a thermometer. After 15 minutes of degassing, sodium hydrosulfite (85%, 9.31 g, 53.5 mmol) under N$_2$ was added immediately and degassing continued for another 10-15 minutes. The temperature of the solution (solution B) was below 5° C. Solution A was then added via canula to solution B under rapid stirring for about 0.5 hour to form a fine dark purple precipitate of Os(Py-MIM)$_2$Cl$_2$. Stirring continued under N$_2$ for another 0.5 hour. The resulting suspension was suction-filtered through a 0.4 or 0.3 micron Nylon membrane. The suspension was transferred to the suction funnel via canula under nitrogen to minimize air exposure. The dark purple precipitate was then washed with a minimum of ice cold water (2×5 mL). The precipitate was immediately dried by lyophilization for at least 24 hours. The yield of Os(Py-MIM)$_2$Cl$_2$ was about 5.6 g (crude).

Synthesis of [Os(PY-MIM)$_2$(MAP)Cl]$^{2+}$2Cl$^-$

To Os(Py-MIM)$_2$Cl$_2$ (10 g, 17.3 mmol), in a 2-L three-neck round bottom flask fitted with a reflux condenser, was added, under a positive pressure of Ar, anhydrous ethanol (0.9 L), 4-(methylamino)pyridine (3.72 g, 34.4 mmol), and activated 4 Å molecular sieves (30 g). The mixture was heated to reflux and stirred magnetically for 17 h and then filtered hot through Whatman #1 on a Büchner funnel. The filtrate was concentrated by rotary evaporation down to about 20 mL, then diluted with anh. EtOH to 25 mL. This solution was then added via syringe pump over 1 h to vigorously stirring MTBE (0.7 L). The mixture was stirred a further 1 h after the addition was complete, and then filtered on a Büchner funnel. The collected ppt was suctioned dry for 15 min, and then transferred to a beaker, redissolving in a total of 500 mL deionized water. Chloride resin (BioRad AG1-X4, c. 40 mL, prerinsed with 200 mL deionized water), was added and the mixture stirred overnight in air to oxidize the product. The mixture was again filtered and the filtrate lyophilized to yield 10.3 g crude [Os(Py-MIM)$_2$(MAP)Cl]$^{2+}$2Cl$^-$.

The crude material was then purified by LH-20 chromatography as follows: A solution of 1 g crude [Os(Py-MIM)$_2$(MAP)Cl]$^{2+}$2Cl$^-$ in 6.5 mL column solvent was loaded onto an 800 mL (5×40 cm) LH-20 column packed in [EtOH:0.1M NH$_4$OH (1:1)] and eluted at 2.5 mL/min. Product elutes as a dark red band (0.64 g after lyophilization, 35% overall yield from the hexachloroosmiate).

As described herein, [Os(Py-MIM)$_2$(MAP)Cl]$^{2+}$2Cl$^-$ is a transition metal complex that is particularly useful as a redox mediator.

Synthesis of [Os(Py-MIM)$_2$(MIM)Cl]$^{2+}$2Cl$^-$

Anhydrous ethanol (1 L) in a 2-L three-neck round bottom flask fitted with a reflux condenser was degassed with N$_2$ for 15 minutes. Os(Py-MIM)$_2$Cl$_2$ (3.1 g, 5.35 mmol) was added quickly under N$_2$ via a funnel. The suspension was stirred and heated to reflux. 1-Methyl-1H-imidazole (0.43 mL, 5.35 mmol) was then added at once via syringe. Reflux continued until the reaction was completed. During the reaction, the solution changed from dark brown to purple-brown. The solution was cooled to room temperature and then suction-filtered through a fritted funnel. The solvent was then removed by rotary evaporation to give the crude product in its reduced form.

The product was transferred with 30-50 mL H$_2$O to a 400 mL beaker containing about 40 mL AG1-X4 chloride resin from Bio-Rad, or preferably, 80 mL Dowex-1-chloride from Aldrich. The mixture was stirred in open air for about 24 hours to convert Os(II) to Os(III). The mixture was then suction-filtered and the resin was washed with H$_2$O (5×30 mL). The combined filtrate was concentrated to about 50 mL by rotary evaporation at 35° C. under vacuum.

The solution was loaded onto a LH-20 column (2"×22"), which was eluted with H$_2$O. 50 mL fractions were collected and analyzed by CV to find the major purple-brown band associated with the product. Fractions containing pure product were collected and concentrated by rotary evaporation to about 150 mL. The solution was then freeze-dried to give the product. The yield of [Os(Py-MIM)$_2$(MIM)Cl]$^{2+}$2Cl$^-$ was about 2.4 g (58% from the hexachloroosmiate).

As described herein, [Os(Py-MIM)$_2$(MIM)Cl]$^{2+}$2Cl$^-$ is a transition metal complex that is particularly useful as a redox mediator.

Example 64

Synthesis of [Os(pMOP-IM)$_2$(biMIM)]$^{3+}$3Cl$^-$

By way of further illustration, an example of the synthesis of [Os(pMOP-IM)2(biMIM)]$^{3+}$3Cl$^-$ ("Dimethoxy"), as illustrated below, is now provided. This example demonstrates how a substitution can be introduced into the Py-MIM ligand as a means of generating mediators that work with FAD-GDH.

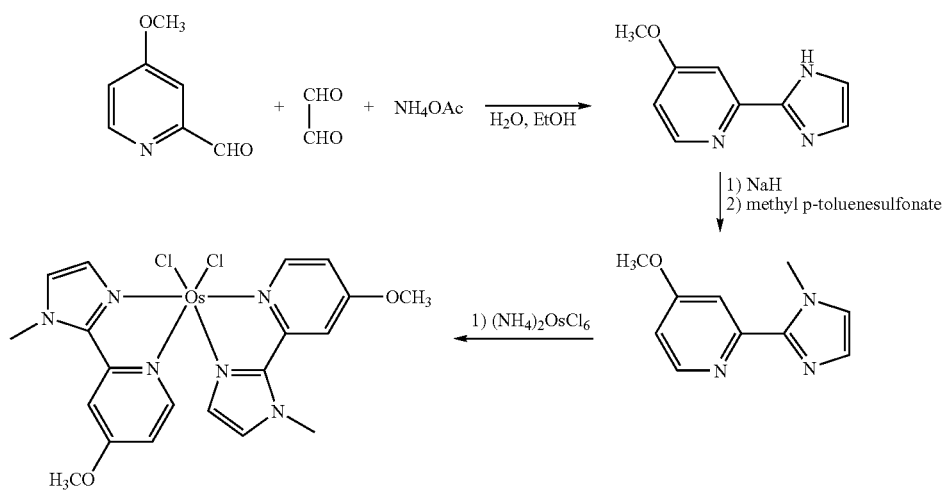

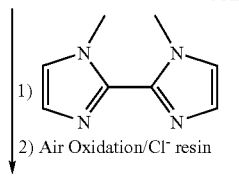

2) Air Oxidation/Cl⁻ resin

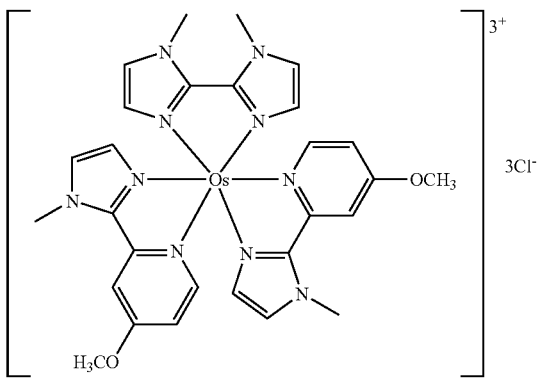

Synthesis of 4-methoxy-2-(1H-imidazol-2-yl)pyridine

To a suspension of ammonium acetate (1.13 g, 14.6 mmol) in 0.2 mL water at 45° C. with mechanical stirring in air, was added a suspension of 4-methoxypyridine carboxaldehyde (Milestone, 0.50 g, 3.65 mmol), glyoxal (40%, 0.50 mL, 4.38 mmol), and 0.87 mL ethanol portionwise over 2.5 h. Rinsed with 0.15 mL ethanol to complete the addition, and stirred a further 30 min at 45° C., then at room temperature overnight. Added 8 mL water, then filtered through Celite. To the filtrate was added dropwise with stirring, 1.4 mL 10% NaOH, then 0.43 g $Na_2CO_3$. Extracted with chloroform (3×10 mL), and washed the combined organic layers with 5 mL brine. Dried over $Na_2SO_4$, and concentrated by rotary evaporation followed by high vacuum overnight, to yield 0.42 g crude 4-methoxy-2-(1H-imidazol-2-yl)pyridine as a brown oil.

Synthesis of 4-methoxy-2-(1-methyl-1H-imidazol-2-yl)pyridine (pMOP-MIM)

To crude 4-methoxy-2-(1H-imidazol-2-yl)pyridine (0.40 g, 2.28 mmol) in 7.5 mL anhydrous DMF with magnetic stirring under Ar at 0° C., NaH (60% in oil, 91 mg, 2.28 mmol) was added portionwise. Stirred at 0-5° C. for 1 h, then added a solution of methyl-p-toluenesulfonate (0.344 mL, 2.28 mmol) in 0.75 mL anh. DMF dropwise with stirring. After 15 min, the ice bath was removed and the reaction mixture stirred for 2 h at room temp. Cooled back to 0° C. and quenched by very carefully adding 10% aq. $Na_2CO_3$ dropwise (about 10 mL total). Extracted 2×30 mL chloroform. Combined organic layers were washed with brine (5 mL), dried over $Na_2SO_4$ and concentrated to give 0.73 g as a dual-phase oil. Chromatographed on 18 g silica gel in 0-2% MeOH/$CHCl_3$+0.5% TEA to yield 0.20 g (45%) of 4-methoxy-2-(1-methyl-1H-imidazol-2-yl)pyridine.

Synthesis of [Os(pMOP-MIM)$_2$(biMIM)]$^{3+}$3Cl$^-$

In a 25-mL one-neck pear flask, 4-methoxy-2-(1-methyl-1H-imidazol-2-yl)pyridine (75 mg, 0.40 mmol), was dried by azeotrope with toluene, then dissolved in anhydrous ethylene glycol under Ar, and added ammonium hexachloroosmiate (IV) (87 mg, 0.20 mmol), degassing by iteratively evacuating and backfilling with Ar. Under a positive pressure of Ar, the reaction mixture was heated to 130° C. for 2 h, then at 140° C. for 28 h. The reaction was cooled to room temp, still under positive Ar pressure, and 1,1'-dimethyl bi-1H-imidazole (prepared via literature methods, 32 mg, 0.20 mmol), was added as a solid. Heated again to 140° C. for 26 h, and cooled to room temp. The crude reaction mixture was diluted with 57 mL water and loaded atop a 25-mL presoaked column of HP-20 resin. Loaded over 2 h, and eluted with water. Combined first few fractions (product) and stirred overnight in open air. Filtered via Büchner and added the appr. 45 mL without further dilution, dropwise over 3 h to a stirring solution of $NH_4PF_6$ (7.5 g in 27 mL $H_2O$). After stirring for 5 days, the ppt was filtered off using Whatman #1 on a Büchner funnel. The brown ppt was suctioned dry for 10 min, then redissolved in 5 mL $CH_3CN$, filtering out the residual clear salt. The filtrate was transferred to a 100 mL beaker, c. 5 mL of prewashed AG1-X4 chloride resin (BioRad) was added, and stirred for 15 min. Deionized water (20 mL) was added over 30 min, and the mixture was stirred overnight. Filtered and lyophilized to yield 51 mg (30%) of [Os(pMOP-MIM)$_2$(biMIM)]$^{3+}$3Cl$^-$ as a dark brown solid.

Example 65

Synthesis of 2-(1-phenyl-1H-imidazol-2-yl)pyridine (Py-PIM)

By way of further illustration, an example of the synthesis of 2-(1-phenyl-1H-imidazol-2-yl)pyridine, as illustrated below, is now provided. This example demonstrates how a 1-aryl-substituted 2-(2-pyridyl)imidazole is made from 1-(2-pyridyl)imidazole or its derivative, and an iodobenzene derivative (as illustrated) or a bromobenzene derivative.

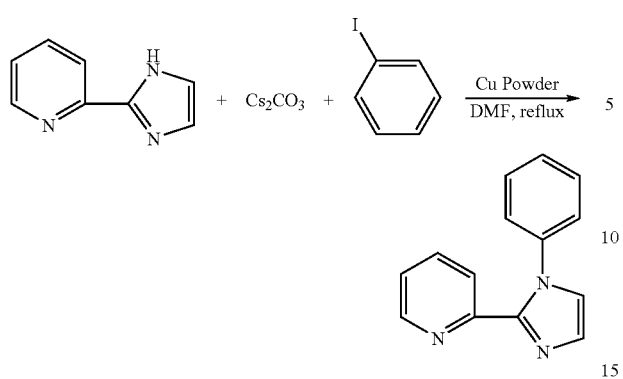

2-(1H-imidazol-2-yl)pyridine (6.91 g), iodobenzene (11.47 g), Cs$_2$CO$_3$ (25 g), and copper powder (15 g) were combined in 60 mL anhydrous DMF in a 250 mL round bottom flask equipped with a magnetic stirrer and a reflux condenser. The mixture was degassed with N$_2$ for 15 minutes at room temperature and then refluxed under N$_2$ in an oil bath for 24 hours. The resulting mixture was cooled to room temperature and suction-filtered to remove the solid byproduct. The filtrate was extracted with EtOAc (3×100 mL). The combined organic layers were washed with H$_2$O (2×100 mL), then with saturated NaCl (2×150 mL), and subsequently dried with anhydrous Na$_2$SO$_4$. Evaporation of the solvent gave crude 2-(1-phenyl-1H-imidazol-2-yl)pyridine. The crude product is generally pure enough to use in making redox mediators, although the crude product may be further purified using a silica gel column and eluting with MeOH/CHCl$_3$.

The 2-(1-phenyl-1H-imidazol-2-yl)pyridine product described above can be used to synthesize transition metal complexes in much the same manner 2-(1-methyl-1H-imidazol-2-yl)pyridine was used in Example 63 above.

Example 66

Comparison of Glucose Oxidation Currents from Different Mediators in PBS

Mediators were first dissolved in PBS at a concentration of 3.0 mg/ml. The solution was subsequently spiked with 1M glucose so that each contained 10 mM glucose. The mediator- and glucose-containing solutions were then fed into FREESTYLE® strips containing FAD-GDH, but no mediators in the strip chemistry. A potential of +100 mV was applied across the carbon and silver electrodes and the resulting current was recorded. The magnitude of the peak currents indicate the rate of the electrocatalytic oxidation of glucose facilitated by different mediators. Two measurements were performed on each solution. Peak currents are tabulated below. Each mediator shows a higher peak current than nPBI.

| | Peak Currents | | |
|---|---|---|---|
| Mediator Name | Ip-1 | Ip-2 | Average Ip |
| Os(bi-pMOP)$_2$(MIM)Cl$_3$ ("DMO") | 52.3 | 56.5 | 54.4 |
| Os(Py-MIM)$_2$(nPBI)Cl$_3$ ("nPBI") | 16.3 | 22.8 | 19.6 |
| Os(Py-MIM)$_2$(MAP)Cl$_3$ ("MAP") | 38.7 | 40.8 | 39.8 |
| Os(Py-MIM)$_2$(DMAP)Cl$_3$ ("DMAP") | 34.2 | 31.5 | 32.9 |
| Os(Py-MIM)$_2$(4-HP)Cl$_3$ ("4-HP") | 28.9 | 29.8 | 29.4 |
| Os(Py-MIM)$_2$(pMOP)Cl$_3$ ("p-MOP") | 37.1 | 32.9 | 35.0 |
| Os(Py-MIM)$_2$(mMOP)Cl$_3$ ("m-MOP") | 34.2 | 35.4 | 34.8 |
| Os(pMOP-MIM)$_2$(biMIM)$_2$Cl$_3$ ("Dimethoxy") | 28.3 | 28.4 | 28.4 |
| Os(MPI)$_2$(AP)Cl$_3$ ("NH$_2$") | — | — | — |

Example 67

Comparison of FAD-GDH FREESTYLE® Strip Performance from Different Mediators in Blood DMO, p-MOP, and MAP were coated with FAD-GDH in FREESTYLE® strips. The strips were tested with 200 mg/dL blood with 8 replicates. A potential of 0 mV was applied to the FREESTYLE® meter. The results are summarized in the following table:

| FAD-026 0 mV | | | | |
|---|---|---|---|---|
| Strip | No. | Glucose reference[1] | Avg (Peak Cur) | Avg (Resp time) |
| DMO | 8 | 199 | 29.3 | 13.1 sec |
| p-MOP | 8 | 199 | 22.6 | 14.7 sec |
| MAP | 8 | 199 | 33.6 | 12.1 sec |

Example 68

Comparison of FAD-GDH FREESTYLE® Strip Performance from Different Mediators in Blood DMO, p-MOP, and MAP were coated with FAD-GDH in FREESTYLE® strips. The strips were tested with 200 mg/dL blood with 6-8 replicates. A potential of 100 mV was applied to the FREESTYLE® meter. The results are summarized in the following table:

| FAD-024 100 mV | | | | |
|---|---|---|---|---|
| Strip | No. | Glucose reference[2] | Avg (Peak Cur) | Avg (Resp time) |
| 1xDMO | 7 | 206 | 31.9 | 7.6 sec |
| 2xDMO | 8 | 206 | 36.2 | 6.8 sec |
| 1xDMAP | 8 | 206 | 30.2 | 9.0 sec |
| 2xDMAP | 8 | 206 | 36.5 | 7.3 sec |
| 1xp-MOP | 8 | 206 | 33.4 | 7.2 sec |
| 2xp-MOP | 8 | 206 | 41.4 | 6.9 sec |

[1]YSI Life Sciences (Yellow Springs, Ohio)
[2]YSI Life Sciences (Yellow Springs, Ohio)

The mediators referred to as "MAP" bis[2-(1-methylimidazol-2-yl-κN$^3$)pyridine-κN]chloro[4-(methylamino)pyridine-κN$^1$)osmium(2+) dichloride and "p-MOP" bis[2-(1-methylimidazol-2-yl-κN$^3$)pyridine-κN]chloro(4-methoxypyridine-κN$^1$)osmium(2+) dichloride perform well as mediators with FAD-GDH. MAP and p-MOP show higher peak currents than the mediator referred to as "nPBI" (Example 66). They also show comparable response times with the mediator referred to as "DMO" (Example 67). They are also known to perform well with the PQQ-GDH enzyme.

Examples of Transition Metal Complexes

Transition metal complexes that serve as redox mediators according to the present invention are provided in Table 12 below, as Mediator Nos. 1-21. The redox potentials ($E_{1/2}$ (mV) relative to a standard Ag/AgCl reference electrode in a pH 7 PBS buffer) associated with these redox mediators are also provided, where available.

Also provided in Tables 13 and 14 are various of these redox mediators and their associated redox potentials and associated slopes, k, of substantially linear plots of collected charge (μC) versus glucose concentration (mg/dL) for a given volume (~315 ηL) of biofluid, such as blood, as further described below. Comparative information for known redox mediators, namely, Comparative Mediator Nos. I, X, XII and XIII is also provided. The slope data in Table 13 and Table 14 concerns redox mediators tested under Condition A and Condition B, respectively, which reflect different ink lots, as now described.

That is, these slope data were obtained from individual tests in which each mediator and an enzyme mixture were coated on a working electrode. The working electrode was made of a conductive ink layered over a plastic substrate. The working electrode was laminated together with a counter/reference electrode, using standard processing known in the art. The counter/reference electrode was made of a Ag/AgCl ink layered over a plastic substrate. Variations are routinely observed in test strip sensors made from different ink lots. Thus, in Table 13, Condition A refers to tests conducted using a series of test strips made from a single lot, and in Table 14, Condition B similarly refers to tests conducted using a series of test strips made from a single lot, different from that associated with Condition A. Thus, comparisons of slope data shown in Table 13 and Table 14 should not be made, while comparisons of slope data shown within either Table 13 or Table 14 are instructive as to mediator performance.

TABLE 12

Examples of Low Potential Mediators of the Present Invention

| Mediator No. | Structure of Mediator | Redox Potential, $E_{1/2}$ (mV) versus Ag/AgCl |
|---|---|---|
| 1 | [structure] | −164 |
| 2 | [structure] | −168 |
| 3 | [structure] | −150 |

TABLE 12-continued

Examples of Low Potential Mediators of the Present Invention

| Mediator No. | Structure of Mediator | Redox Potential, $E_{1/2}$ (mV) versus Ag/AgCl |
|---|---|---|
| 4 | | −172 |
| 5 | | |
| 6 | | |
| 7 | | −154 |

TABLE 12-continued
Examples of Low Potential Mediators of the Present Invention
| Mediator No. | Structure of Mediator | Redox Potential, $E_{1/2}$ (mV) versus Ag/AgCl |
|---|---|---|
| 8 | 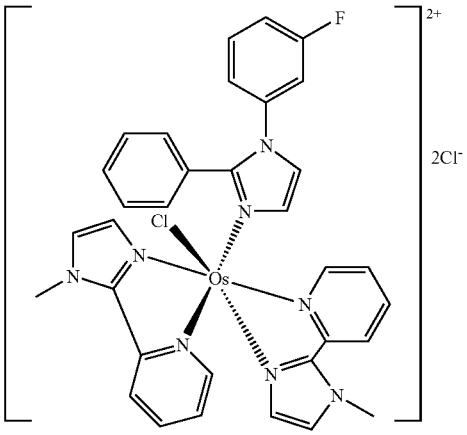 | −139 |
| 9 | 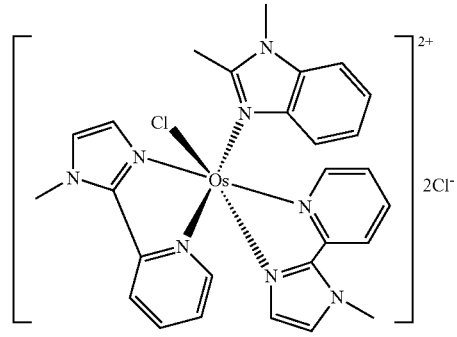 | −124 |
| 10 | 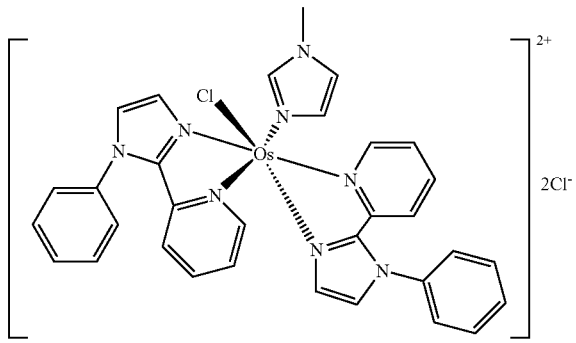 | −117 |
| 11 | 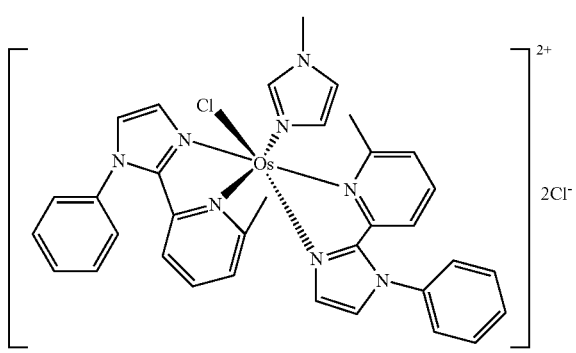 | −130 |

TABLE 12-continued

Examples of Low Potential Mediators of the Present Invention

| Mediator No. | Structure of Mediator | Redox Potential, $E_{1/2}$ (mV) versus Ag/AgCl |
|---|---|---|
| 12 | | −166 |
| 13 | | −88 |
| 14 | Os(MPI)$_2$(m-MOP)Cl$_3$ "m-MOP" bis[2-(1-methylimidazol-2-yl-κN$^3$)pyridine-κN]chloro(3-methoxypyridine-κN$^1$)osmium(2+) dichloride | −30 |
| 15 | Os(MPI)$_2$(p-MOP)Cl$_3$ "p-MOP" bis[2-(1-methylimidazol-2-yl-κN$^3$)pyridine-κN]chloro(4-methoxypyridine-κN$^1$)osmium(2+) dichloride | −90 |

TABLE 12-continued

Examples of Low Potential Mediators of the Present Invention

| Mediator No. | Structure of Mediator | Redox Potential, $E_{1/2}$ (mV) versus Ag/AgCl |
|---|---|---|
| 16 | 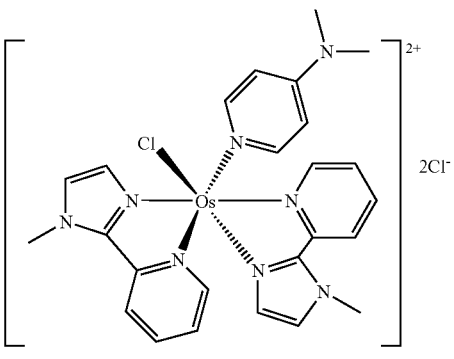<br>Os(MPI)$_2$(DMAP)Cl$_3$ "DMAP"<br>bis[2-(1-methylimidazol-2-yl-$\kappa N^3$)pyridine-$\kappa N$]chloro(4-(dimethylamino)pyridine-$\kappa N^1$)osmium(2+) dichloride | −155 |
| 17 | 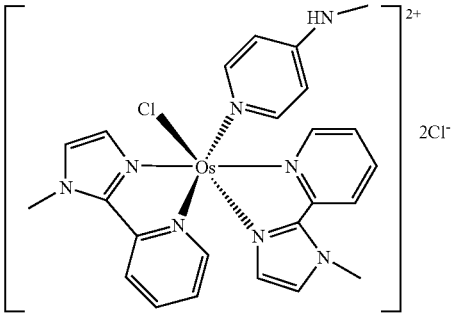<br>Os(MPI)$_2$(MAP)Cl$_3$ "MAP"<br>bis[2-(1-methylimidazol-2-yl-$\kappa N^3$)pyridine-$\kappa N$]chloro[4-(methylamino)pyridine-$\kappa N^1$)osmium(2+) dichloride | −160 |
| 18 | 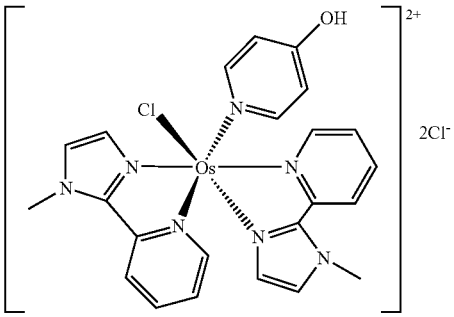<br>Os(MPI)$_2$(4HP)Cl$_3$ "4-HP"<br>bis[2-(1-methylimidazol-2-yl-$\kappa N^3$)pyridine-$\kappa N$]chloro[4-hydroxypyridine-$\kappa N^1$)osmium(2+) dichloride | −185 |

TABLE 12-continued

Examples of Low Potential Mediators of the Present Invention

| Mediator No. | Structure of Mediator | Redox Potential, $E_{1/2}$ (mV) versus Ag/AgCl |
|---|---|---|
| 19 | Os(MIMOP)$_2$(MI)$_2$Cl$_2$ "Dimethoxy" bis[2-(1-methylimidazol-2-yl-κN$^3$)-4-methoxypyridine-κN](1,1'-dimethyl-2,2'-biimidazole κN$^3$,N$^3$)osmium(2+) dichloride | −78 |
| 20 | "nPBI" bis[2-(1-methylimidazol-2-yl-κN$^3$)pyridine-κN]chloro(1-pentylbenzimidazole-κN$^3$)osmium(2+) dichloride) | −125 |
| 21 | "DMO" bis[4,4'-dimethoxy-2,2'-bipyridine-κN,N')]chloro(3-methylimidazole-κN$^3$)osmium(2+) dichloride | −105 |

TABLE 13

Examples of Low Potential Osmium Mediators and
Known Comparative Mediators and Properties Thereof Under Condition A

| Mediator No. Or Comparative Mediator No. | Structure of Mediator or Comparative Mediator | Redox Potential, $E_{1/2}$ (mV) versus Ag/AgCl | Linear Slope, k ($\mu$C/ (mg/dL)) |
|---|---|---|---|
| 1 | | −164 | 1.52 |
| 2 | | −168 | 1.49 |
| 3 | | −150 | 1.46 |
| 4 | | −172 | 1.49 |

TABLE 13-continued

Examples of Low Potential Osmium Mediators and
Known Comparative Mediators and Properties Thereof Under Condition A

| Mediator No. Or Comparative Mediator No. | Structure of Mediator or Comparative Mediator | Redox Potential, $E_{1/2}$ (mV) versus Ag/AgCl | Linear Slope, k (μC/(mg/dL)) |
|---|---|---|---|
| 11 | 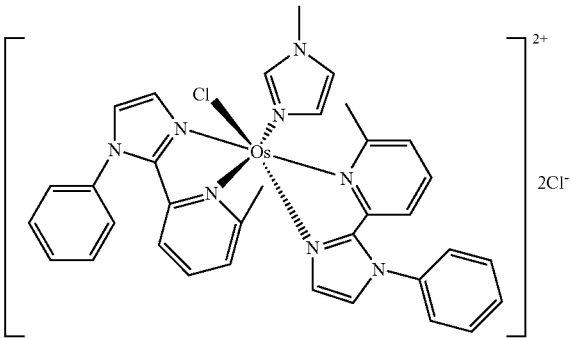 | −130 | 1.55 |
| I* | 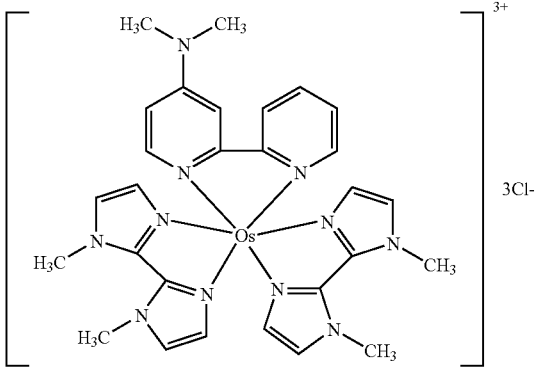 | −110 | 1.14 |
| X* | 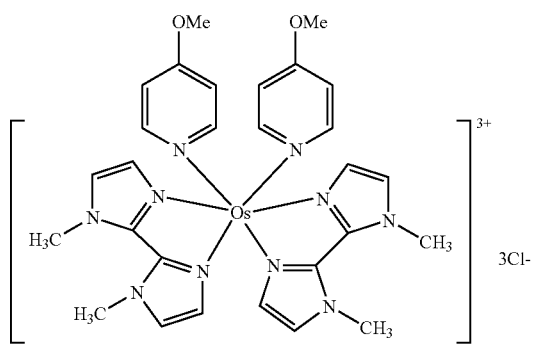 | −125 | 1.05 |

*These known comparative mediators are disclosed in International Publication No. WO 01/36430 A1 and are merely comparative examples herein.

TABLE 14

Examples of Low Potential Osmium Mediators and
Known Comparative Mediators and Properties Thereof Under Condition B

| Mediator No. Or Comparative Mediator No. | Structure of Mediator or Comparative Mediator | Redox Potential, $E_{1/2}$ (mV) versus Ag/AgCl | Linear Slope, k ($\mu$C/(mg/dL)) |
|---|---|---|---|
| 8 | | −139 | 1.73 |
| 9 | | −124 | 1.70 |
| X* | | −125 | 1.48 |
| XII* | | −74 | 1.46 |

TABLE 14-continued

Examples of Low Potential Osmium Mediators and
Known Comparative Mediators and Properties Thereof Under Condition B

| Mediator No. Or Comparative Mediator No. | Structure of Mediator or Comparative Mediator | Redox Potential, $E_{1/2}$ (mV) versus Ag/AgCl | Linear Slope, k (µC/(mg/dL)) |
|---|---|---|---|
| XIII* | 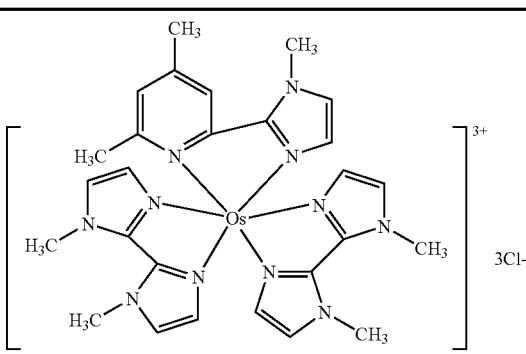 | −97 | 1.52 |

*These known comparative mediators are disclosed in International Publication No. WO 01/36430 A1 and are merely comparative examples herein.

The transition metal complexes of the present invention are well suited for electrochemical sensing applications, given their particular electrochemical properties. For example, as shown above, the redox potentials of the mediators are generally low, such as in a range of from about 0 mV to about −200 mV relative to a Ag/AgCl reference electrode. These redox potentials are particularly desirable for electrochemical sensing applications, being in a range at which the kinetics of the mediators is fast and the electrochemical activity of potentially interfering species is minimized. Mediator Nos. 1-21 thus exemplify electrochemically desirable mediators which are coordination complexes comprising osmium according to the present invention.

The identity of the potentially interfering species just described depends on the particular electrochemical sensing application. Merely by way of example, when the electrochemical sensing application concerns the biofluid, blood, potentially interfering species include ascorbic acid, acetaminophen, and uric acid. Mediator Nos. 1-21 exemplify electrochemically desirable mediators which are coordination complexes comprising osmium that operate at potentials suitable for minimizing the electrochemical activity of such potentially interfering species, while not sacrificing mediator efficiency.

Additionally, the transition metal complexes of the present invention are particularly effective redox mediators in electrochemical sensing applications, given their enhanced ability to collect charge at the working electrode, which in turn enhances the sensitivity of the sensor to the concentration of the analyte being sensed. By way of example, in the general operation of an electrochemical biosensor, such as a glucose sensor, the reduced enzyme, glucose oxidase or glucose dehydrogenase, transfers its electrons to the working electrode via a particular process. In that process, the oxidized form of the redox mediator interacts with the reduced enzyme, thereby receiving an electron and becoming reduced. The reduced mediator travels to the surface of the working electrode, typically by random diffusion, whereupon it transfers the collected electron to the electrode, thereby becoming oxidized.

Ideally, because each glucose molecule loses two electrons in the above-described process, the total amount of electrons or charge collected at the working electrode should be equal to two times the number of glucose molecules oxidized. In practice, however, the total amount of charge collected is almost always less than the ideal or theoretical amount because the electrons may be "lost" during transfer from the enzyme to the electrode. For example, the reduced enzyme may transfer the electrons to oxygen or other chemical species, rather than to the redox mediator. An efficient redox mediator should thus compete favorably for electrons from the enzyme.

Further, ideally, once the redox mediator receives an electron from the enzyme, it should not transfer the electron to another oxidative species, such as oxygen or other chemicals present in the sensor, before being oxidized on the working electrode. A good mediator should thus compete favorably for electrons from the reduced enzyme, as described above, and be substantially chemically inert during its random diffusion to the working electrode whereupon it is oxidized.

An efficient mediator is particularly important in coulometry-based electrochemical biosensing, in which detection of the bioanalyte is based on the total amount of charge collected at the working electrode for a given volume of biofluid. When greater charge is collected at the working electrode, the sensor is advantageously more sensitive. For a coulometry-based glucose sensor, for example, the sensitivity of the sensor may be characterized by the slope value of a linear plot of charge versus glucose concentration as defined by the equation $y=kx+b$, where y is the collected charge in µC for a given volume of biofluid, k is the slope in µC/(mg/dL), x is the glucose concentration in mg/dL, and b is the intercept based on background charge. As demonstrated above, mediators of the present invention that have a negatively charged ligand, such as Mediator Nos. 1-21 that have a chloride ligand, have associated slope values that are significantly higher (for example, about 28% to about 48% higher per Table 13, and about 11% to about 18% higher per Table 14) than those of mediators that have heterocyclic nitrogen-containing ligands surrounding the metal redox center, as exemplified by Comparative Mediator Nos. I, X, XII and XIII.

The above-described data demonstrate favorable properties of transition metal complexes that make these complexes particularly desirable redox mediators. In electrochemical sensing applications, such as the electrochemical sensing of glucose, the transition metal complexes effectively collect electrons from the reduced enzyme and effectively retain the collected electrons prior to delivering them to the working electrode.

As described herein, the transition metal complexes of the present invention are usefully employed as redox mediators in electrochemical sensors. These mediators have very fast kinetics, such that electron exchange between such a mediator and the enzyme and/or the working electrode in the sensor device is rapid, and more particularly, rapid enough to facilitate the transfer of electrons to the working electrode that might otherwise be transferred to another electron scavenger, such as oxygen. The electron-transfer efficiency of a mediator of Formula 1 is enhanced when $L_2$ is a negatively charged ligand, such as a chloride ligand, as demonstrated by the desirable slope values, k, listed above for Mediator Nos. 1-21. By way of comparison, a mediator having a neutral ligand, $L_2$, such as a heterocyclic nitrogen-containing ligand, is less able to transfer electrons from the enzyme to the working electrode, as reflected by the lower slope values listed above for Comparative Mediator Nos. I, X, XII and XIII.

The transition metal complex mediators of the present invention are also quite stable in terms of chemical reactivity with respect to chemical species other than the enzyme and the electrode surface. By way of example, the chemical stability of a mediator of the present invention is such that preferably the predominant, or most preferably the only, reactions in which it participates involves the above-described, electron-transfer reaction between the mediator and the enzyme and the electrochemical redox reaction at the working electrode. This chemical stability may be enhanced when a mediator of Formula 1 wherein $L_2$ is a negatively charged monodentate ligand, has a "bulky" chemical ligand, $L_1$, that spatially or stereochemically shields the redox center, such as Os2+/3+, and thereby, reduces undesirable chemical reactivity beyond the fundamentally desired chemical and electrochemical activity. Mediator Nos. 1-21, above, are particular examples of such "bulked", chemically stable mediators of the present invention.

Further by way of example, the thermal and photochemical stability of a mediator of the present invention is preferably such that the mediator is temperature- and light-stable, respectively, under typical use, storage and transportation conditions. For example, mediators of the present invention may be easily handled under normal lighting conditions and may have a shelf life of at least about 18 months at about room temperature, and at least about 2 weeks at about 57° C. Mediator Nos. 1-21, above, are particular examples of such thermally and photochemically stable mediators of the present invention.

Mediators of the claimed sensors have desirable redox potentials in a range at which the electron-transfer kinetics is optimized, or maximized, and the effect of common interfering species present in biofluid is minimized. Mediator Nos. 1-21, above, are particular examples of mediators of suitable redox potential.

The transition metal complex mediators of the present invention also have desirable solubility properties, generally having a solubility of greater than about 0.1 moles/liter at 25° C. for a desired solvent, which is typically an aqueous or a water-miscible solvent. Advantageously, one need only adjust the counter ion or ions, X, of Formula 1, to obtain a desirable solubility for the solvent of choice, be it aqueous or organic.

In summary, the claimed subject matter is directed to enzyme-based electrochemical sensors comprising transition metal complexes with pyridyl-imidazole ligands, which show improved response times in the detection and quantification of fluid analytes. Said transition metal complexes are particularly useful as redox mediators in electrochemical sensing applications. The preferred redox mediators exchange electrons rapidly with enzymes and working electrodes, are stable, are readily synthesized, and have redox potentials that are tailored for the electrooxidation of a variety of analytes, such as those in various biological fluids within the human body. While mediators of the present invention have been described for the most part in terms of glucose sensing, they are useful for the sensing of other analytes, such as lactic acid for example. Generally, if the redox potential of the enzyme used in a particular analyte-sensing application is negative relative to the redox potential of the mediator, the mediator is suitable for that analyte-sensing application. The advantageous properties and characteristics of the transition metal complexes of the present invention make them ideal candidates for use in the electrochemical sensing of glucose, an application of particular importance in the diagnosis and monitoring of diabetes in human populations.

Various aspects and features of the present invention have been explained or described in relation to beliefs or theories, although it will be understood that the invention is not bound to any belief or theory. Further, various modifications, equivalent processes, as well as numerous structures to which the present invention may be applicable will be readily apparent to those of skill in the art to which the present invention is directed upon review of the instant specification. Although the various aspects and features of the present invention have been described with respect to various embodiments and specific examples herein, it will be understood that the invention is entitled to protection within the full scope of the appended claims.

Various modifications and alterations of the embodiments and examples in accordance to the embodiments will become apparent to those skilled in the art without departing from the scope and spirit of the disclosure, and it should be understood that this disclosure is not to be unduly limited to the illustrative embodiments set forth herein.

What we claim is:

1. A biosensor comprising:
    at least one electrode; and
    a reagent composition associated with the at least one electrode, the reagent composition comprising:
    a polymer mixture comprising polyvinyl alcohol-polyethylene glycol graft copolymer and polyvinyl alcohol or a polymer mixture comprising polyvinyl acetate and polyvinylpyrrolidone and an effective analyte detecting amount of:
    an enzyme;
    an enzyme cofactor; and
    a redox compound capable of acting in a biosensor as
       (i) a redox mediator for a working electrode;
       (ii) a redox couple for a reference electrode; or
       (iii) a redox mediator for a working electrode and the redox couple for a reference electrode.

2. The biosensor of claim 1 wherein the polymer mixture has dispersed within it an effective amount of
    an enzyme;
    an enzyme cofactor; and
    a redox compound capable of acting in a biosensor as
       (i) a redox mediator for a working electrode;
       (ii) a redox couple for a reference electrode; or
       (iii) a redox mediator for a working electrode and the redox couple for a reference electrode.

3. The biosensor of claim 1 wherein the polymer mixture comprises polyvinyl alcohol-polyethylene glycol graft copolymer and polyvinyl alcohol.

4. The biosensor of claim 1 wherein the polymer mixture comprises polyvinyl acetate and polyvinylpyrrolidone.

5. The biosensor of claim 1 wherein the redox compound comprises:

$$[M(PQ)_3]X_2$$

wherein:
M is Ni, Mn, Fe, Co, Os, or Ru;
PQ is

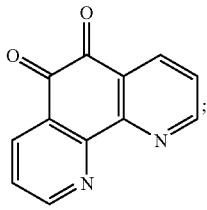

and X is a counter anion.

6. The biosensor of claim 1 wherein the reagent composition further comprises:
the enzyme is a NAD(P)-dependent dehydrogenase;
the enzyme cofactor is NAD sodium salt; and
the redox compound is [Ni(PQ)3]C12, [Ni(PQ)3]Br2 or mixtures thereof;
wherein PQ is

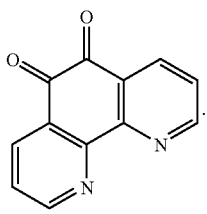

7. The biosensor of claim 1 wherein:
the redox compound is $[M(PQ)_3]X_2$
wherein:
M is Fe or Ru;
PQ is

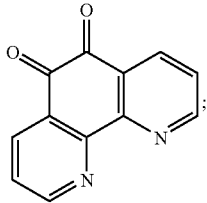

and X is a counter anion.

8. The biosensor of claim 1 wherein:
the redox compound is $[OS(PQ)_3]X_2$
wherein:

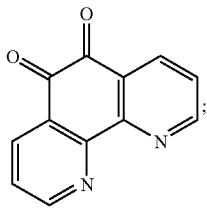

PQ is
and X is a counter anion.

9. The biosensor of claim 1 wherein:
the enzyme is dehydrogenase; and
the enzyme cofactor comprises NAD sodium salt, FAD or PQQ.

10. The biosensor of claim 1 wherein:
the enzyme is NAD(P)-dependent dehydrogenase;
the enzyme cofactor is NAD sodium salt; and
the redox mediator is [Ni(PQ)3]C12, [Ni(PQ)3]Br2 or mixtures thereof
wherein PQ is

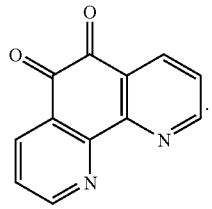

11. A biosensor film comprising
a polymer mixture comprising polyvinyl alcohol-polyethylene glycol graft copolymer and polyvinyl alcohol or a polymer mixture comprising polyvinyl acetate and polyvinylpyrrolidone and an effective analyte detecting amount of:
an enzyme;
an enzyme cofactor; and
a redox compound capable of acting in a biosensor as
    (i) a redox mediator for a working electrode;
    (ii) a redox couple for a reference electrode; or
    (iii) a redox mediator for a working electrode and the redox couple for a reference electrode.

12. The biosensor film of claim 11 wherein the polymer mixture has dispersed within it an effective amount of:
an enzyme;
an enzyme cofactor; and
a redox compound capable of acting in a biosensor as
    (i) a redox mediator for a working electrode;
    (ii) a redox couple for a reference electrode; or
    (iii) a redox mediator for a working electrode and the redox couple for a reference electrode.

13. The biosensor film of claim 11 wherein the redox compound is of the formula:

$[M(PQ)_3]X_2$ wherein:
M is Ni, Mn, Fe, Co, Os, or Ru;
PQ is

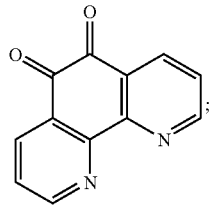

and X is a counter anion.

14. The biosensor film of claim 11 wherein:
the enzyme is dehydrogenase; and
the enzyme cofactor comprises NAD sodium salt, FAD or PQQ.

15. The biosensor film of claim 11 wherein:
the enzyme is a NAD(P)-dependent dehydrogenase;
the enzyme cofactor is NAD sodium salt; and
the redox compound is $[Ni(PQ)_3]Cl_2$, $[Ni(PQ)_3]Br_2$ or mixtures thereof
wherein PQ is

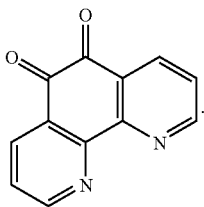

16. The biosensor film of claim 11 wherein:
the redox compound is $[M(PQ)_3]X_2$
wherein:
M is Fe or Ru;
PQ is

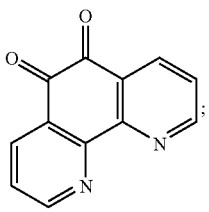

and X is a counter anion.

17. The biosensor film of claim 11 wherein:
the redox compound is $[OS(PQ)_3]X_2$
wherein:
PQ is

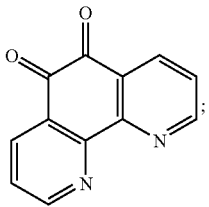

and X is a counter anion.

18. The biosensor film of claim 11 further comprising a colorant.

19. The biosensor film of claim 18 wherein the colorant is a flavin mononucleotide (FMN) of the structure:

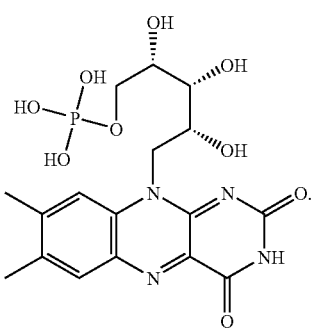

20. The biosensor film of claim 11 wherein the polymer mixture comprises polyvinyl alcohol-polyethylene glycol graft copolymer and polyvinyl alcohol.

21. The biosensor film of claim 20 wherein the number average molecular weight ($M_n$) of the polyvinyl alcohol-polyethylene glycol graft copolymer is from about 30,000 to about 60,000.

22. The biosensor film of claim 11 wherein the polymer mixture comprises polyvinyl acetate and polyvinylpyrrolidone.

23. The biosensor film of claim 22 wherein the number average molecular weight ($M_n$) of the polyvinyl acetate is from about 10,000 to about 2,000,000.

24. A reagent composition comprising:
a polymer mixture comprising polyvinyl alcohol-polyethylene glycol graft copolymer and polyvinyl alcohol or a polymer mixture comprising polyvinyl acetate and polyvinylpyrrolidone and an effective analyte detecting amount of:
an enzyme;
an enzyme cofactor; and
a redox compound capable of acting in a biosensor as
(i) a redox mediator associated with a working electrode;
(ii) a redox couple associated with a reference electrode; or
(iii) the redox mediator associated with the working electrode and the redox couple for the reference electrode.

25. The composition of claim 1 wherein the reagent composition covers at least a portion of the working electrode, at least a portion of the reference electrode or both at least a portion of the working electrode and at least a portion of the reference electrode.

26. The composition of claim 1 wherein the rheology of the reagent composition is substantially Newtonian and is in the range from about 0.5 mPa s to about 25 mPa s.

27. The composition of claim 1 wherein the polymer mixture has dispersed within it an effective amount of:
an enzyme;
an enzyme cofactor; and
a redox compound capable of acting in a biosensor as
(i) a redox mediator for a working electrode;
(ii) a redox couple for a reference electrode; or
(iii) a redox mediator for a working electrode and the redox couple for a reference electrode.

28. The composition of claim 1 wherein the polymer mixture comprises polyvinyl alcohol-polyethylene glycol graft copolymer and polyvinyl alcohol.

29. The composition of claim 1 wherein the polymer mixture comprises polyvinyl acetate and polyvinylpyrrolidone.

30. The composition of claim 1 wherein the number average molecular weight ($M_n$) of the polyvinyl alcohol-polyethylene glycol graft copolymer is from about 30,000 to about 60,000.

31. The composition of claim 1 wherein the number average molecular weight ($M_n$) of the polyvinyl acetate is from about 10,000 to about 2,000,000.

32. The composition of claim 1 wherein the redox compound is of the formula:

$[M(PQ)_3]X_2$ wherein:
M is Ni, Mn, Fe, Co, Os, or Ru;
PQ is

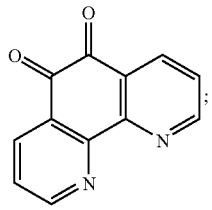

and X is a counter anion.

33. The composition of claim 1 wherein:
the enzyme is cholesterol dehydrogenase; and
the enzyme cofactor comprises NAD sodium salt, FAD or PQQ.

34. The composition of claim 1 wherein:
the enzyme is 3-hydroxybutyrate dehydrogenase; and
the enzyme cofactor comprises NAD sodium salt, FAD or PQQ.

35. The composition of claim 1 further comprising a trigger electrode.

36. The composition of claim 35 wherein the reagent composition covers at least a portion of the trigger electrode.

37. The composition of claim 1 wherein:
the enzyme is dehydrogenase; and
the enzyme cofactor comprises NAD sodium salt, NAD (P), NAD, FAD or PQQ.

38. The composition of claim 37 wherein the enzyme is glucose GDH dependent, cholesterol dependent or ketone dependent.

39. The composition of claim 37 wherein:
the enzyme is a NAD(P)-dependent dehydrogenase;
the enzyme cofactor is NAD sodium salt; and
the redox compound is [Ni(PQ)$_3$]Cl$_2$, [Ni(PQ)$_3$]Br$_2$ or mixtures thereof
wherein PQ is

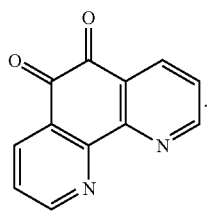

40. The composition of claim 37 wherein:
the redox compound is [M(PQ)$_3$]X$_2$
wherein:
M is Fe or Ru;
PQ is

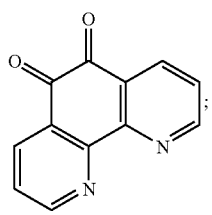

and X is a counter anion.

41. The composition of claim 37 wherein:
the redox compound is [OS(PQ)$_3$]X$_2$
wherein:
PQ is

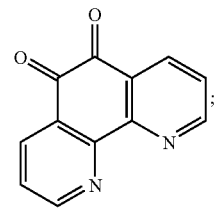

and X is a counter anion.

42. The composition of claim 37 wherein:
the redox compound is independently [Fe(CN)$_6$]$^{3-}$ (ferricyanide), [Ru(NH$_3$)]$^{3+}$(hexaammine ruthenium(III)), 2,6-dichlorophenol indophenol (DCIP), [Os(dmo)$_2$(1-vinyl imidazole)X]X, [Os(dmo)$_2$(1-vinyl imidazole)X]X$_2$, [Os(dmo)$_2$(imidazole)X]X, [Os(dmo)$_2$(imidazole)X]X$_2$, [Os(dmo)$_2$(1-methyl imidazole)X]X$_2$, [Os(dmo)$_2$(methylimidazole)X]X$_2$

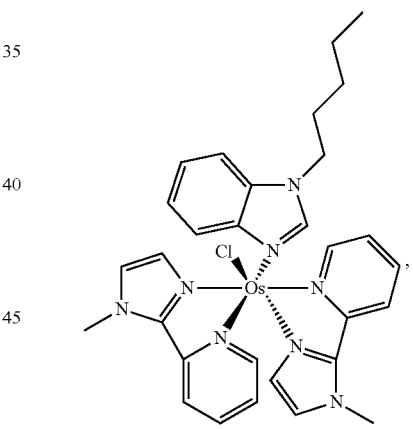

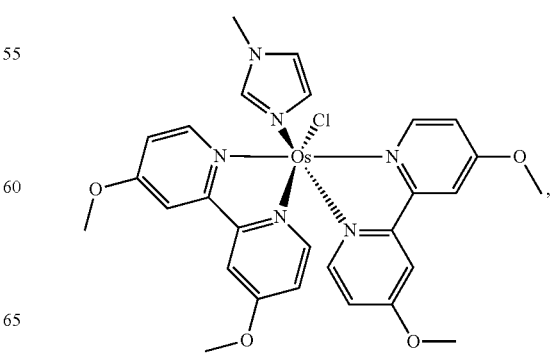

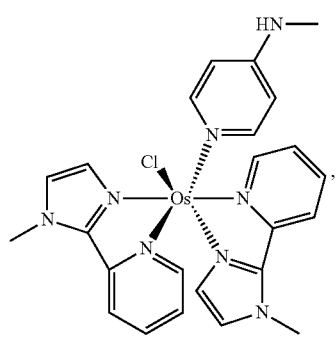
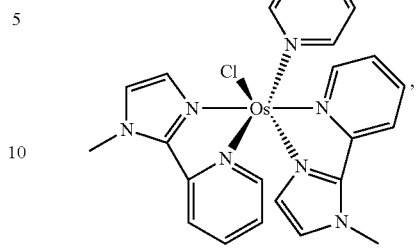
or mixtures thereof,
wherein:
dmo is 4,4'-dimethoxy-2,2'-bipyridine, and X is halogen.
* * * * *